(12) United States Patent
Kayed et al.

(10) Patent No.: US 12,391,657 B2
(45) Date of Patent: Aug. 19, 2025

(54) SMALL MOLECULES THAT BIND AND/OR MODULATE DIFFERENTFORMS OF TAU OLIGOMERS

(71) Applicant: The Board of Regents of the University of Texas System, Austin, TX (US)

(72) Inventors: Rakez Kayed, Galveston, TX (US); Filippa Lo Cascio, Sicily (IT); Antonio Palumbo Piccionello, Sicily (IT); Andrea Pace, Sicily (IT)

(73) Assignees: The Board of Regents of the University of Texas System, Austin, TX (US); UNIVERSITY OF PALERMO, Palermo (IT)

( * ) Notice: Subject to any disclaimer, the term of this patent is extended or adjusted under 35 U.S.C. 154(b) by 902 days.

(21) Appl. No.: 17/606,004

(22) PCT Filed: Apr. 23, 2020

(86) PCT No.: PCT/US2020/029575
§ 371 (c)(1),
(2) Date: Oct. 22, 2021

(87) PCT Pub. No.: WO2020/219714
PCT Pub. Date: Oct. 29, 2020

(65) Prior Publication Data
US 2022/0204462 A1    Jun. 30, 2022

Related U.S. Application Data

(60) Provisional application No. 62/837,709, filed on Apr. 23, 2019.

(51) Int. Cl.
| | |
|---|---|
| *C07D 271/06* | (2006.01) |
| *C07C 49/255* | (2006.01) |
| *C07C 69/734* | (2006.01) |
| *C07C 225/22* | (2006.01) |
| *C07C 255/37* | (2006.01) |
| *C07C 255/42* | (2006.01) |

(52) U.S. Cl.
CPC .......... *C07D 271/06* (2013.01); *C07C 49/255* (2013.01); *C07C 69/734* (2013.01); *C07C 225/22* (2013.01); *C07C 255/37* (2013.01); *C07C 255/42* (2013.01)

(58) Field of Classification Search
CPC .................................................. C07D 271/06
USPC ......................................................... 548/131
See application file for complete search history.

(56) References Cited

PUBLICATIONS

Hollande et al, Int. J. Mol. Sci. (2018) vol. 19(11): 3358/1-3358/13.*

Obregon-Mendoza et al, Int. J. Org Chem. (2018) vol. 8(4): 359-377.*

Bhattacharya et al, Royal Soc, Open Sci. (2017) vol. 4(10): 170748/1-170748/10.*

\* cited by examiner

*Primary Examiner* — Taofiq A Solola
(74) *Attorney, Agent, or Firm* — HYLTON-RODIC LAW PLLC

(57) ABSTRACT

The present invention relates to novel small molecules of Formulas I, II, III, Ilia, Illb, and IV and pharmaceutically acceptable salts thereof, as well as the preparation and the use thereof.

4 Claims, 36 Drawing Sheets

CURCUMIN

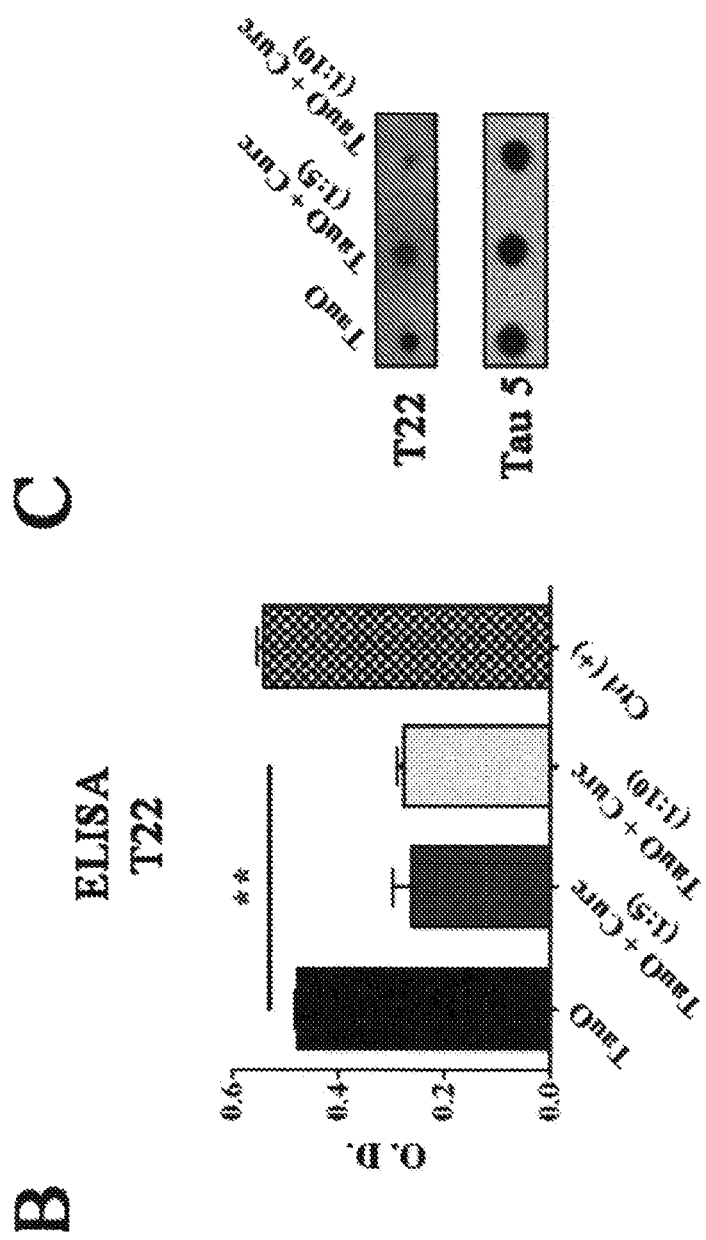
FIG. 2B-C b. Curcumin-like (CL 1-12)

Cal 1-9

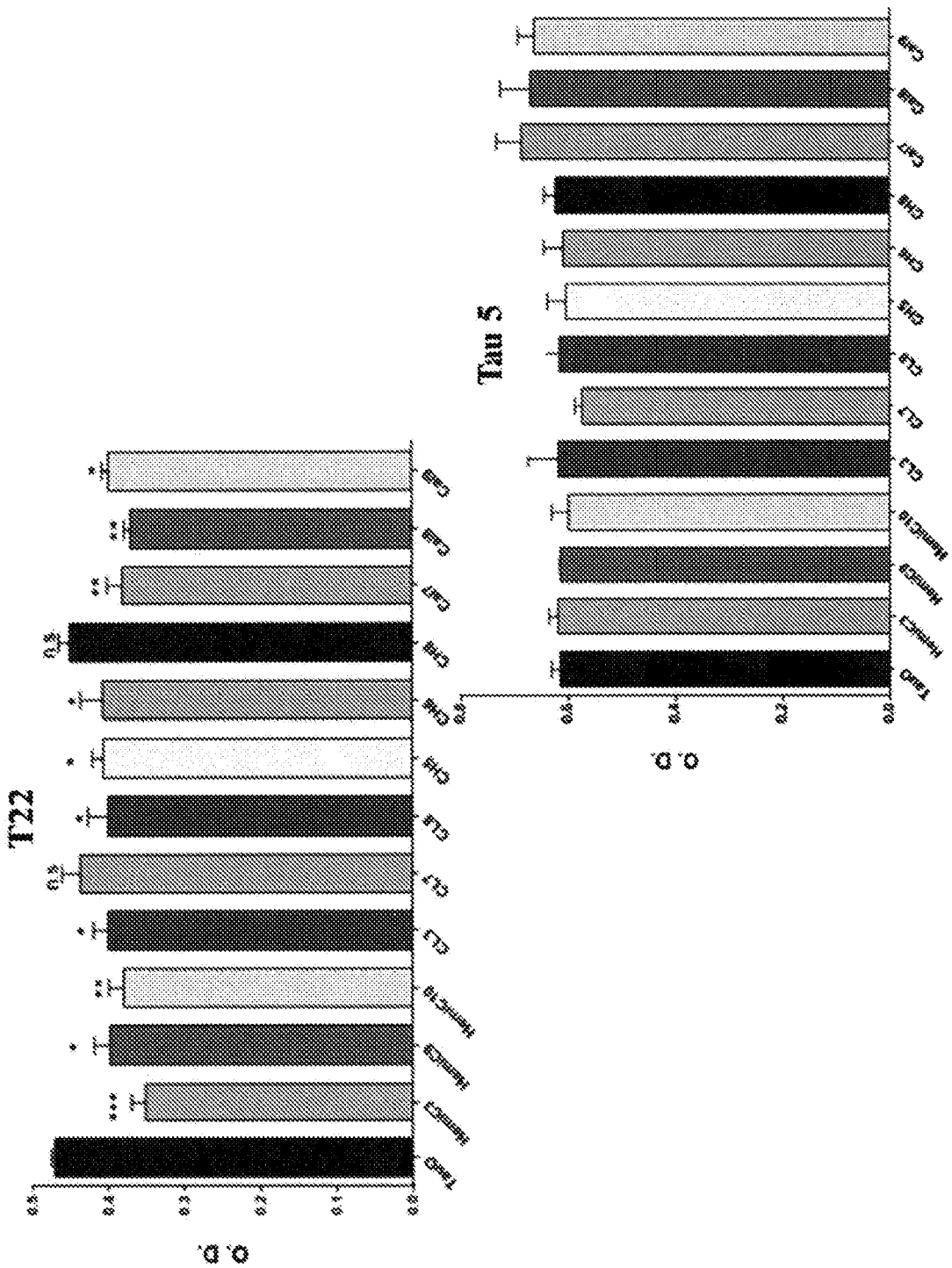

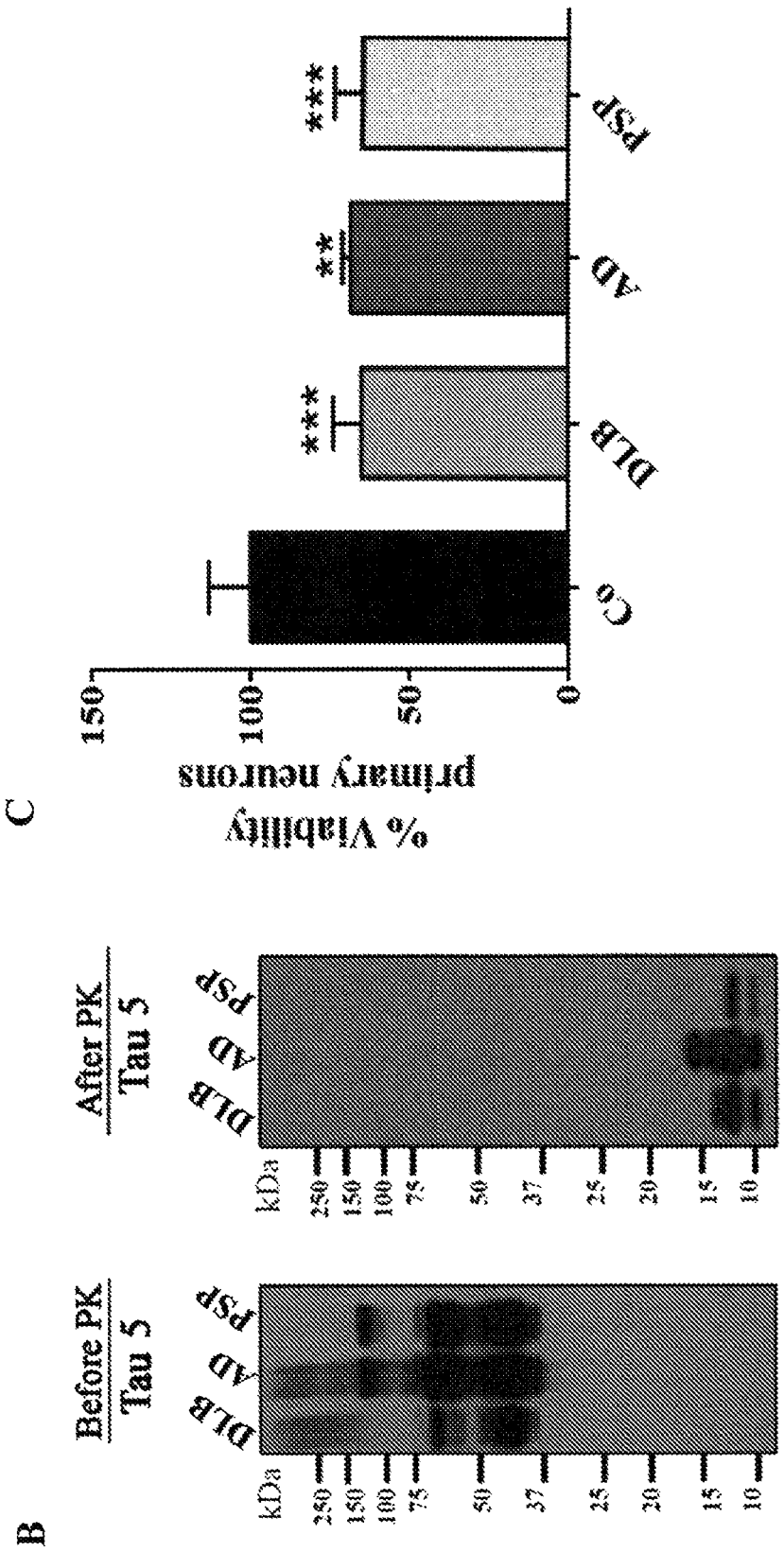
FIG. 12B-C

FIG. 14B-D
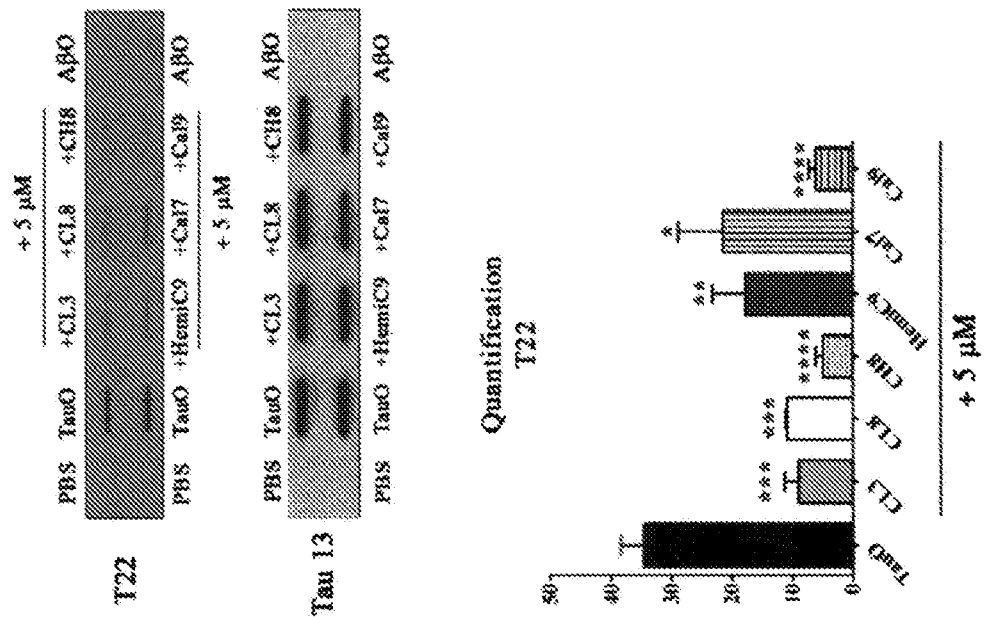

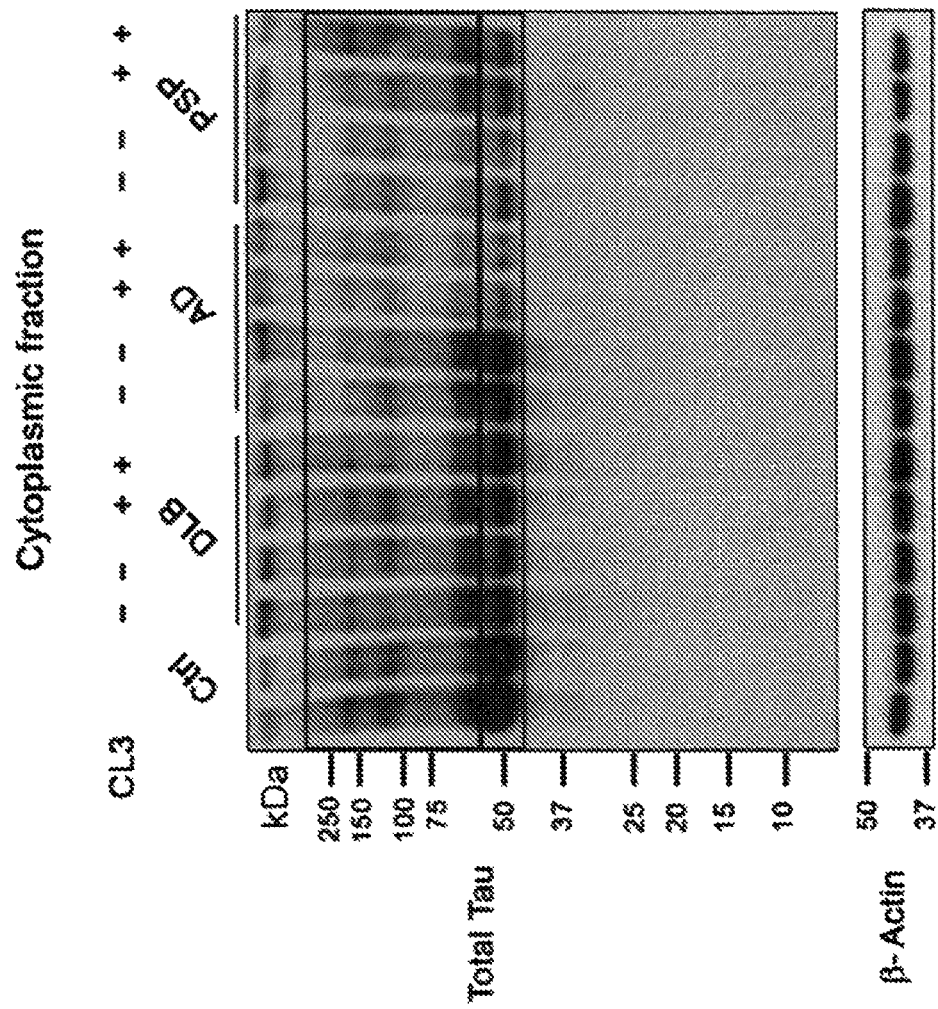

SMALL MOLECULES THAT BIND AND/OR MODULATE DIFFERENTFORMS OF TAU OLIGOMERS

CROSS REFERENCE TO RELATED APPLICATIONS

This application is a U.S. national stage application of International Application No. PCT/US20/29575, filed 2020 Apr. 24, which claims the benefit of the filing date of European Application 62/837,709 filed 2019 Apr. 23, the contents of which are hereby incorporated by reference in their entirety.

FIELD OF THE INVENTION

The field of the invention relates generally to novel small molecules that bind and/or modulate different forms of tau oligomers (TauO) as well as the preparation and the use thereof.

BACKGROUND

Curcumin, a polyphenol extracted from the plant Curcuma longa, has several broad biological activities such as antioxidant and anti-inflammatory effects with a low-toxicity profile. Indeed, it plays an important role in the prevention and treatment of many diseases including neurodegenerative disorders. Curcumin is a high lipophilic molecule with low molecular weight which can easily cross the BBB. Moreover, it is capable of binding and inhibiting the aggregation and deposition of insoluble amyloid aggregates. Therefore, it has been shown to alter the misfolding of many amyloid proteins through the disruption of π-stacking due to the presence of conjugated phenol residues. Curcumin significantly reduces β-amyloid and tau pathology in transgenic AD mouse models. Studies have shown that curcumin is capable of labelling amyloid deposits both ex vivo and in vivo, disrupting existing plaques and partially restoring distorted neurites in transgenic AD mice. In addition, curcumin can decrease levels of tau hyperphosphorylation in cells and mice and can also bind to fibrillar tau (Park, Kim et al. 2008). Recently, curcumin was also found to be able to selectively suppress soluble tau dimers in aged Htau mice. In addition, curcumin was also found to improve tau-mediated neuronal dysfunction and neuritic abnormalities in *C. Elegans*.

Therefore, extensive preclinical studies have proposed curcumin as a potential therapeutic approach against AD and related neurodegenerative disease. Many human clinical trials have been performed but none of them have been successful and their failures may be due to curcumin's poor solubility in aqueous buffers and low brain bioavailability following oral administration. Indeed, curcumin is metabolized very rapidly via glucuronidation, primarily in the liver and intestine, before reaching the systemic circulation and the BBB. Hence, its use as a potential therapeutic for AD and other neurodegenerative diseases has been a challenge. Therefore, alternative formulations and drug delivery systems, including liposomes and nanoparticles, have been formulated to boost its bioavailability. Furthermore, curcumin analogs were created to improve its well-established shortcomings.

The inventors synthesized novel curcumin derivatives to overcome one of the major curcumin drawbacks, its low cerebral bioavailability, which hampers its use as a potential therapeutic agent for AD and related diseases. The invention encompasses curcumin derivatives encompasses four different classes: Hemi-curcuminoids (HemiC 1-10), Curcumin-like (CL 1-12), Heterocyclic curcumin-like (CH 1-11) and Calebin-A analogs (Cal 1-9) (FIG. 4.1).

These novel compounds were synthesized to easily cross the BBB, target and modulate tau oligomers aggregation state, neutralizing their toxicity and internalization in an effort to prevent or slow the spread of tau pathology.

This background information is provided for the purpose of making information believed by the applicant to be of possible relevance to the present invention. No admission is necessarily intended, nor should it be construed, that any of the preceding information constitutes prior art against the present invention.

(A) Western blot analysis of tau oligomers probed with the oligomeric tau antibody T22 and total tau antibodies, Tau 5 and Tau 13. Curcumin interacts and alters the aggregation states of preformed tau oligomers as compared to the untreated control, TauO. (B) ELISA analysis of oligomeric tau treated with increased concentration of curcumin showing a significant decrease in T22 immunoreactivity as compared to tau oligomers alone. Data were compared by one-way analysis of variance (ANOVA) followed by Dunnett's multiple comparison test: $p<0.01$ (C) Dot blot analysis show decreased levels of oligomeric tau in the presence of curcumin. (D) Viability percentage of cultured SH-SY5Y human neuroblastoma cells exposed to 2 μM of tau oligomers, 2 μM of tau oligomers pre-incubated with curcumin and controls. SH-SY5Y cells given TauO pretreated with curcumin had significantly higher cells viability when compared to TauO alone and Ctrl. Data were compared by one-way analysis of variance (ANOVA) followed by Dunnett's multiple comparison test: Co vs TauO, TauO+Curc, Fibrils: **$p<0.001$; TauO vs TauO+Curc: $<0.001$. Bars and errors represent the mean and standard deviation.

Figure 3:
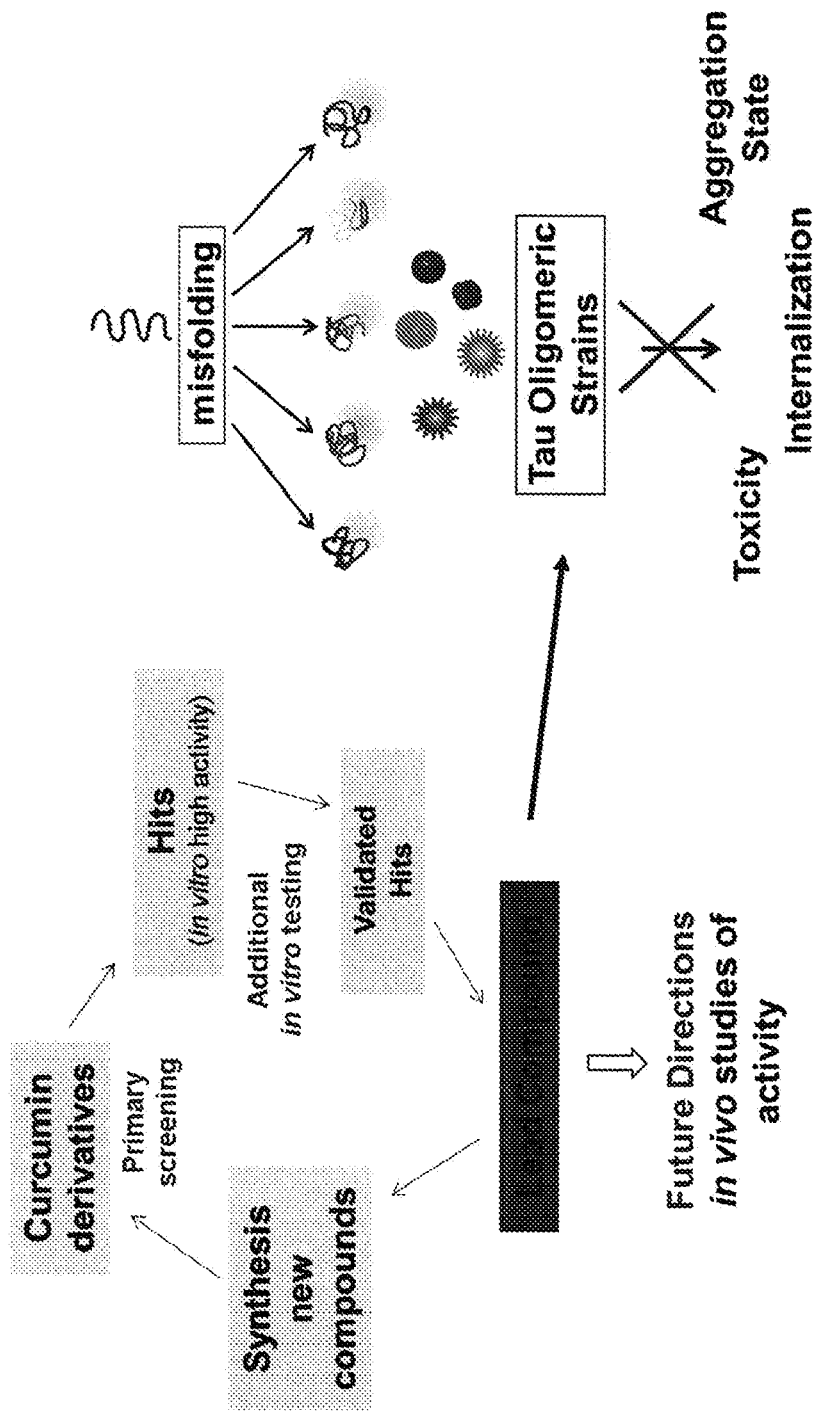

FIG. 3. Flowchart describing the approach used to screen and develop biologically active curcumin derivatives.

Schematic representing the hypothetical model for the formation of tau oligomeric strains and the steps for developing active curcumin derivatives from initial in vitro screening using recombinant tau to the validation of the hits in disease-relevant tau oligomeric strains. Tau monomer misfolding leads to the formation of conformationally distinct misfolded monomers that aggregate into different oligomers. Toxic tau oligomeric strains can be targeted and modulated by active compounds inhibiting oligomers toxicity and internalization thus preventing further aggregation of tau and progression of tau pathology.

Figure 4A:
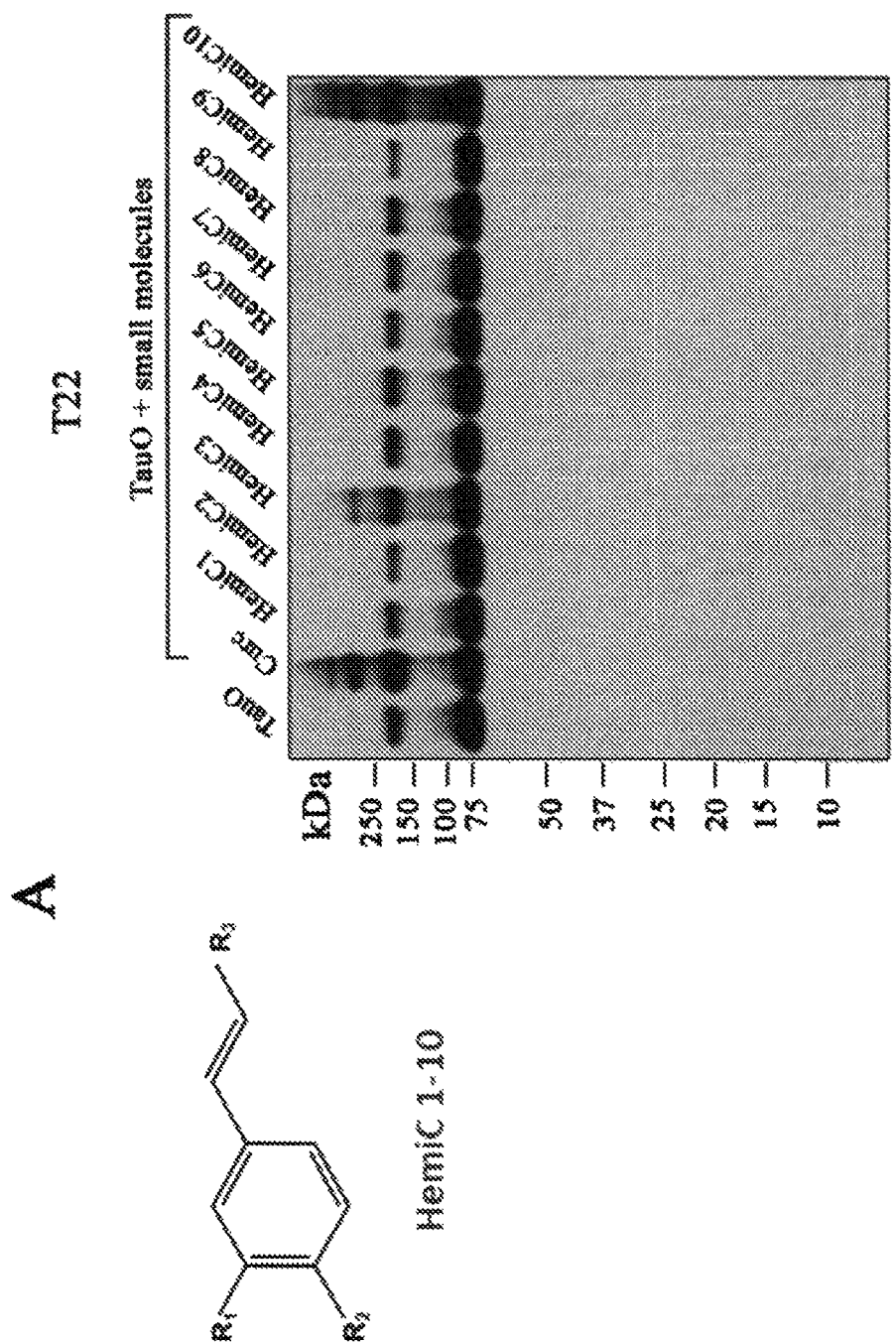
Figure 4B:
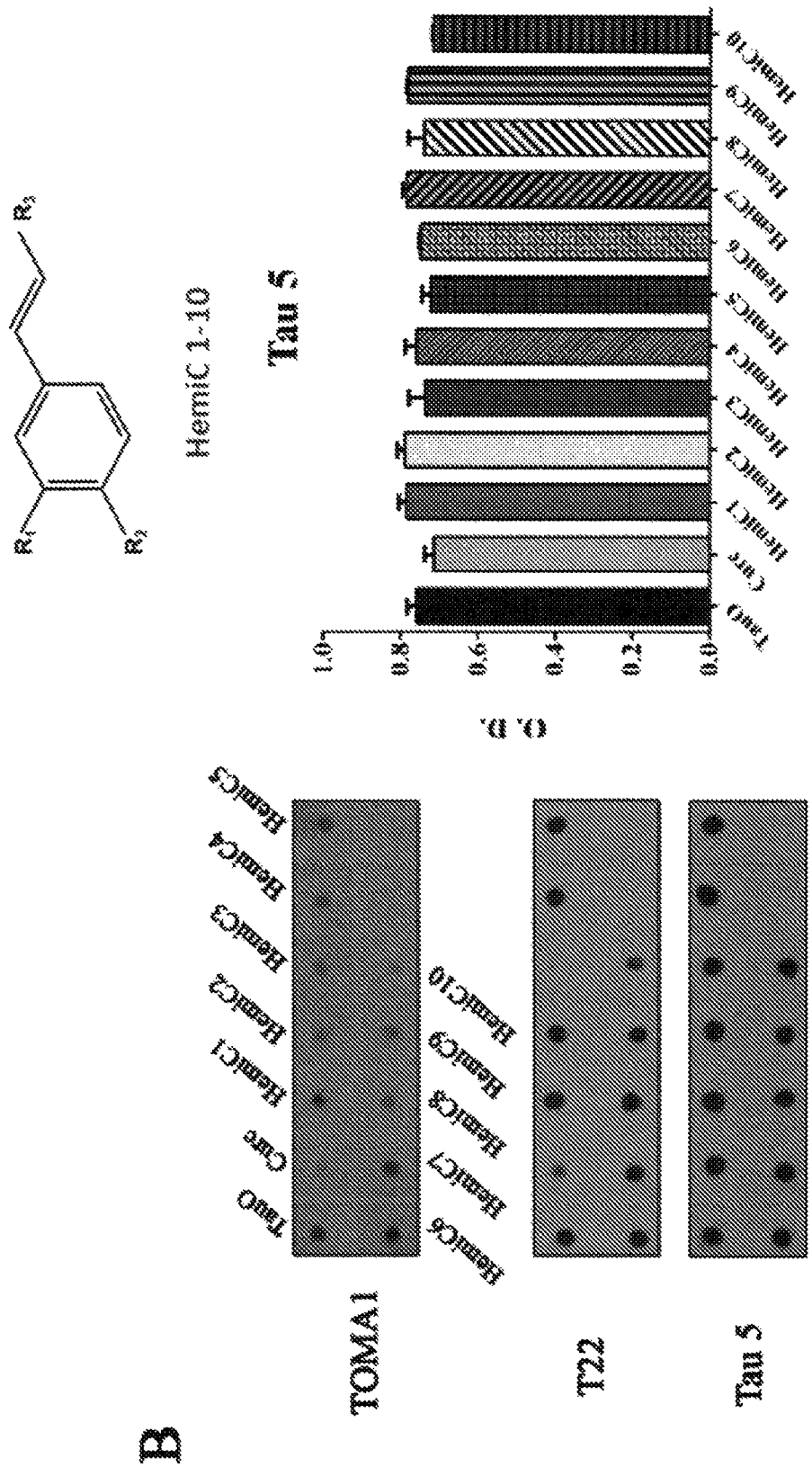
Figure 4C:
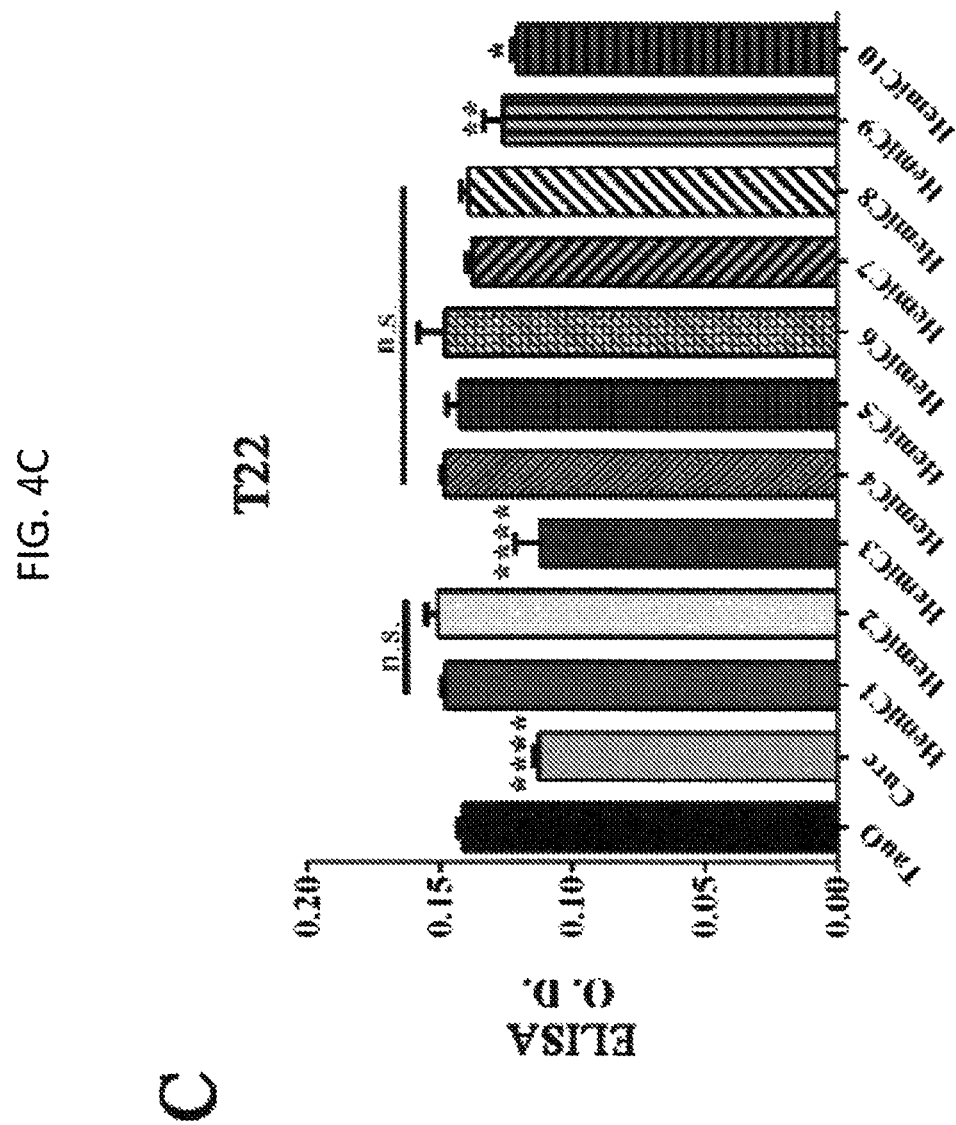

FIGS. 4A-C. Biochemical analysis of oligomeric Tau treated with compound HemiC derivatives and untreated control.

(A) Western blot analysis of 3 μg/μl of tau oligomers alone and pretreated with curcumin and Hemi-curcuminoid analogs probed with T22, shows that some of the compounds are able to alter the aggregation states of preformed tau oligomers. (B) Dot Blots analysis of oligomeric tau alone and in the presence of HemiC, probed with TOMA1, T22 and Tau5, shows that some of the HemiC compounds are able to decrease tau oligomer levels as compared to the untreated control. (C) ELISA analysis of oligomeric tau with and without HemiC analogs shows that some HemiC are able to affect tau aggregation pathways reducing tau oligomer levels as compared to the untreated control while there is no change in total tau protein using Tau5. Data were compared by one-way analysis of variance (ANOVA) followed by Dunnett's multiple comparison test: (*p<0.05; p<0.01**p<0.0001) Bars and errors represent the mean and standard deviation.

Figure 5A:
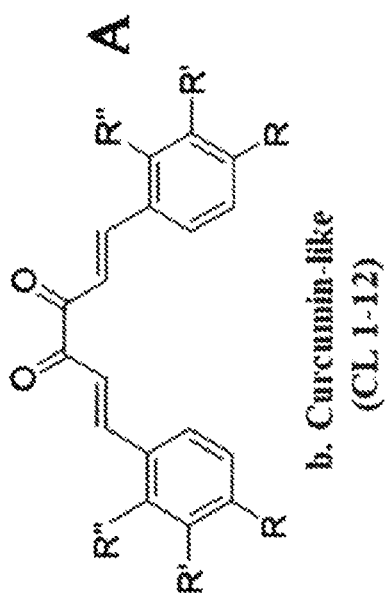
Figure 5A:
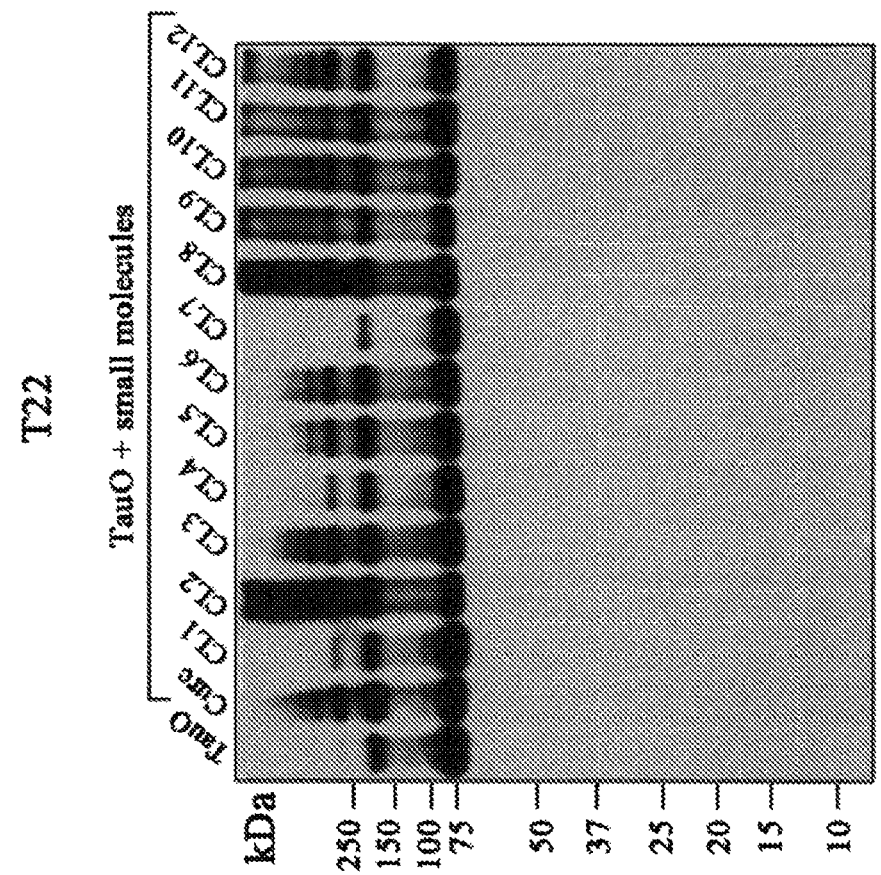
Figure 5B:
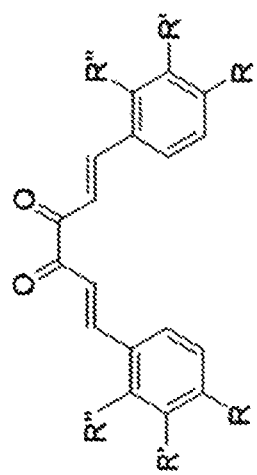
Figure 5B:
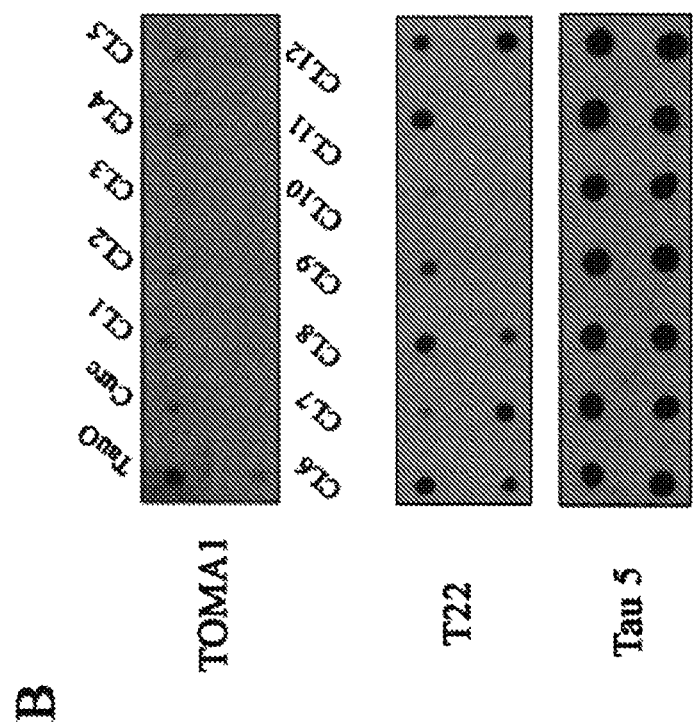
Figure 5C:
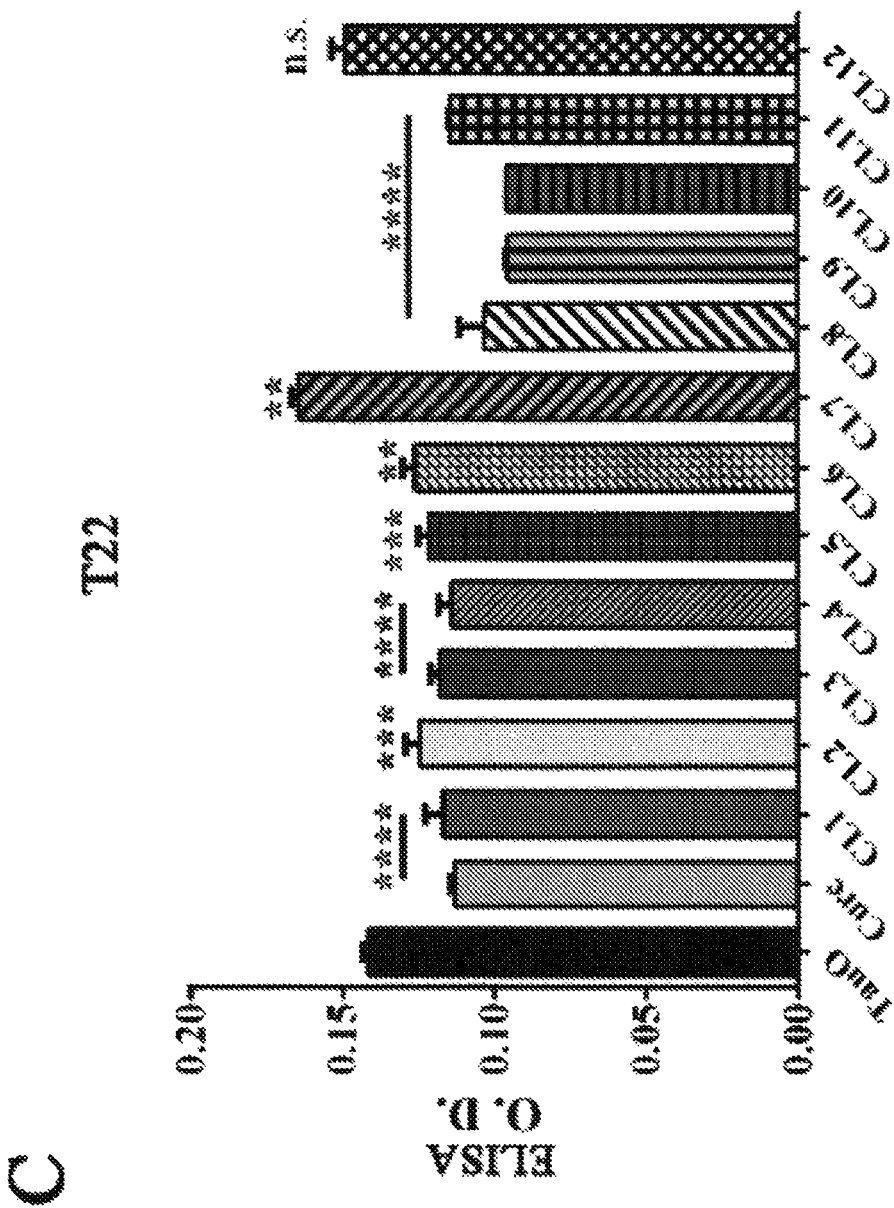

FIGS. 5A-C Biochemical analysis of oligomeric Tau treated with Curcumin-like (CL) derivatives and untreated control.

(A) Western blot analysis of 3 µg/µl of tau oligomers alone and pretreated with curcumin and CL analogs, probed with T22, shows that the compounds are able to alter the aggregation states of preformed tau oligomers. (B) Dot blot analysis probed with anti-oligomeric monoclonal and polyclonal tau antibodies, respectively TOMA1 and T22, and total tau antibody, Tau 5. (C) ELISA analysis of oligomeric tau shows a significant decrease in the tau oligomer levels in the presence of the CL compounds as compared to the untreated control, TauO. Data were compared by one-way analysis of variance (ANOVA) followed by Dunnett's multiple comparison test: (p<0.01; *p<0.001****p<0.0001). Bars and errors represent the mean and standard deviation.

Figure 6A:
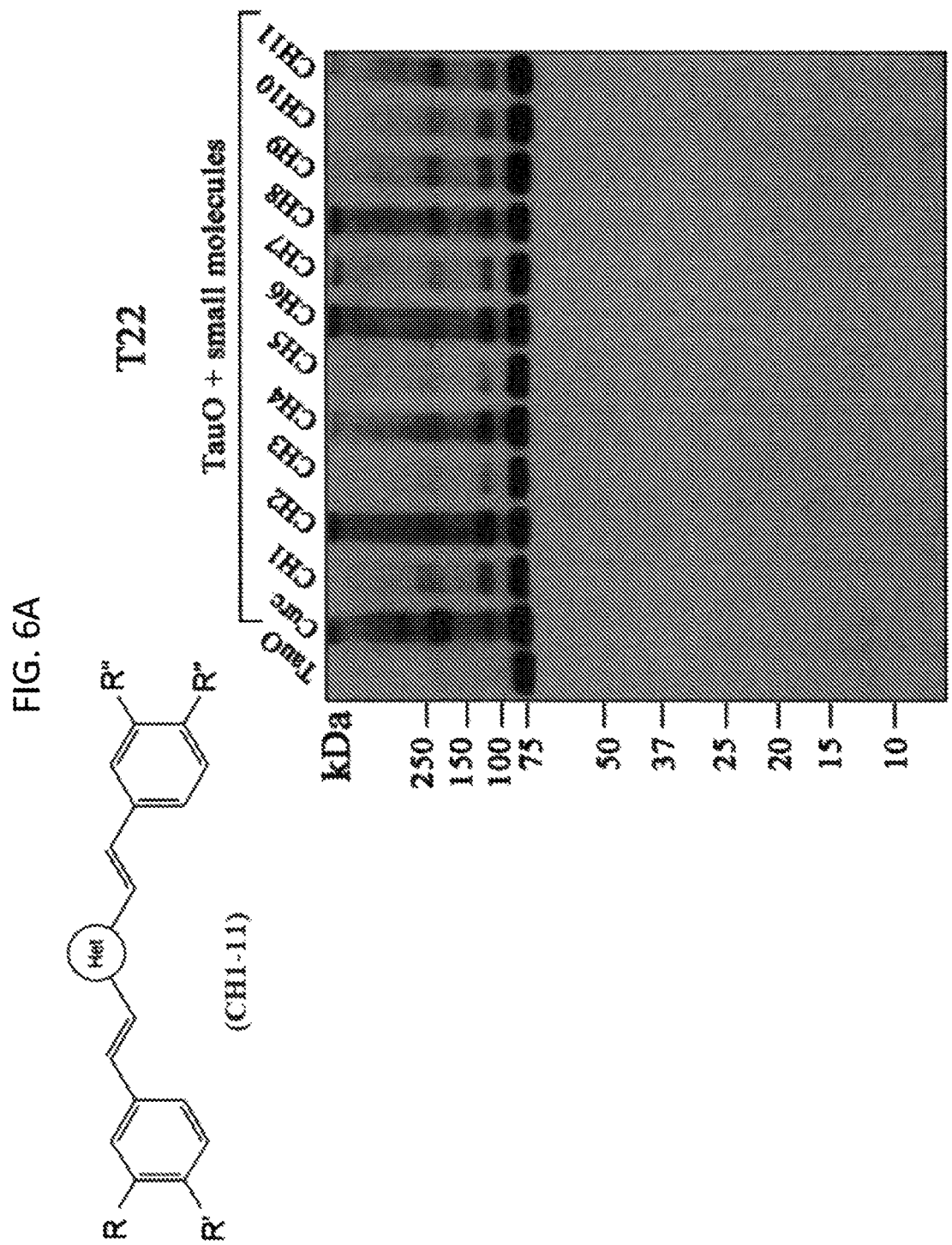
Figure 6B:
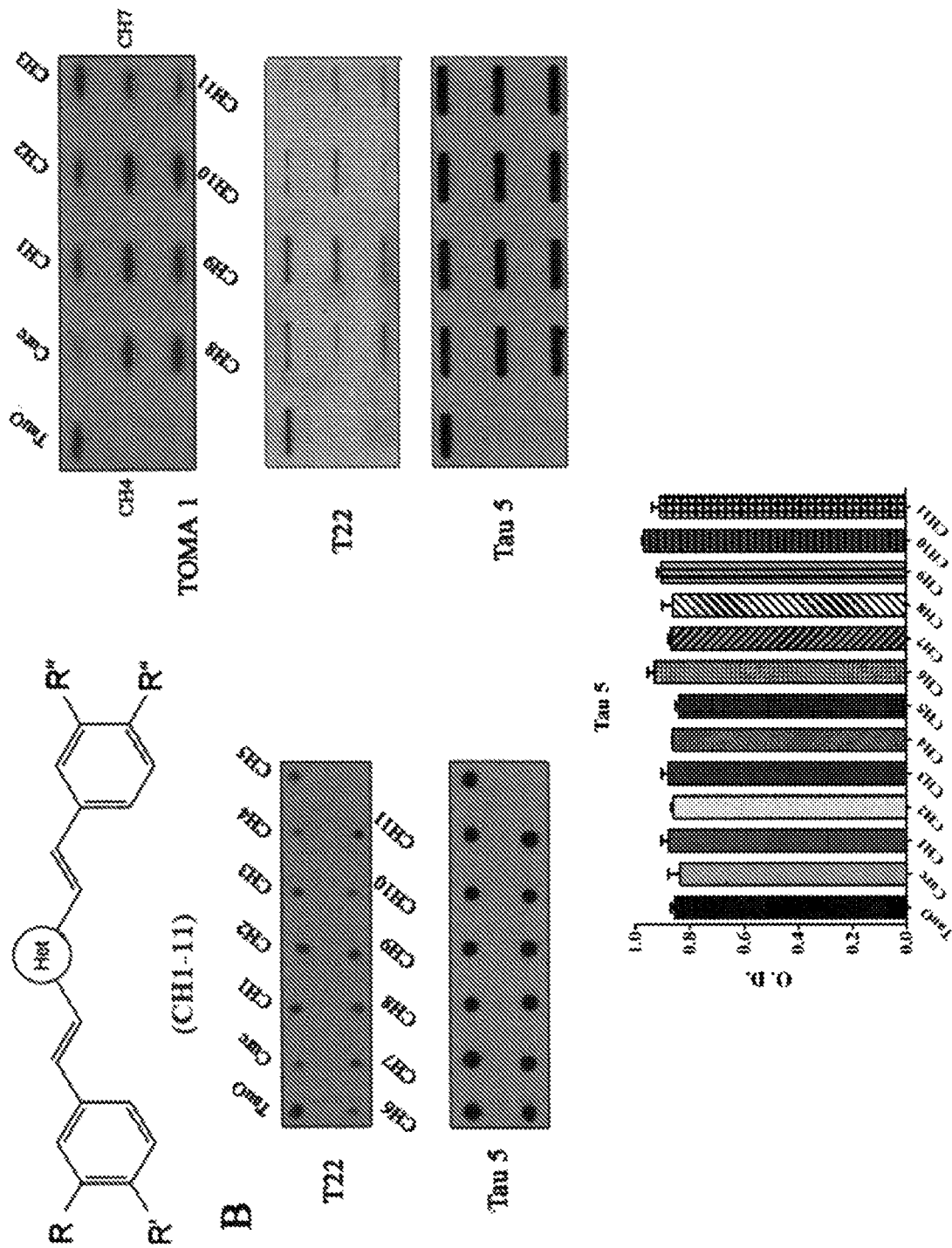
Figure 6C:
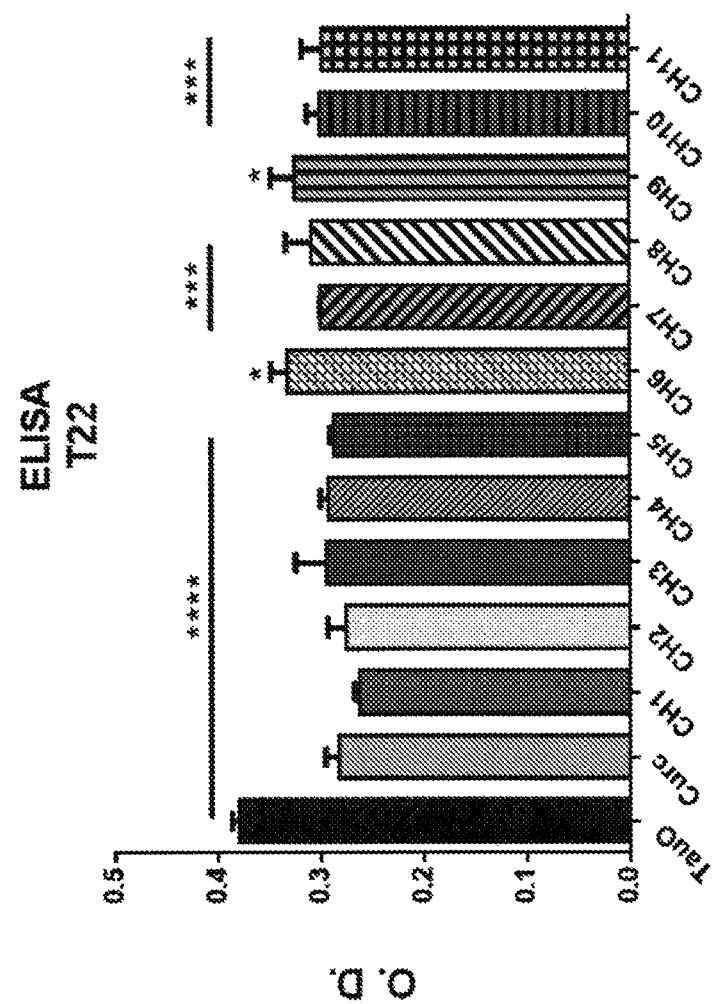

FIGS. 6A-C Biochemical analysis of oligomeric Tau with and without Heterocyclic curcumin (CH) derivatives treatment.

(A) Western blot analysis of 3 µg/µl of tau oligomers alone and pre-treated with curcumin and Heterocyclic curcumin analogs probed with T22, shows that the incubation with the compounds modulates the aggregation states of preformed tau oligomers as compared to the untreated TauO. (B) Filter Trap and Dot blot analyses of tau oligomers alone and pre-treated with curcumin and CH analogs probed with T22 and Tau 5. Some of the compounds are able to alter the aggregation states of preformed tau oligomers resulting in decreased tau oligomer levels as compared to tau oligomers alone. CH analogs are able to reduce the Tau Oligomer Monoclonal Antibody TOMA1 immunoreactivity. (B) ELISA analysis of oligomeric tau with and without CH derivatives show no changes in total tau protein using Tau 5 antibody, (C) ELISA probed with the anti-oligomeric specific tau antibody, T22, show decreased immunoreactivity after treatment with the compounds. Data were compared by one-way analysis of variance (ANOVA) followed by Dunnett's multiple comparison test: (*p<0.05; *p<0.001**p<0.0001) Bars and errors represent the mean and standard deviation.

Figure 7A:
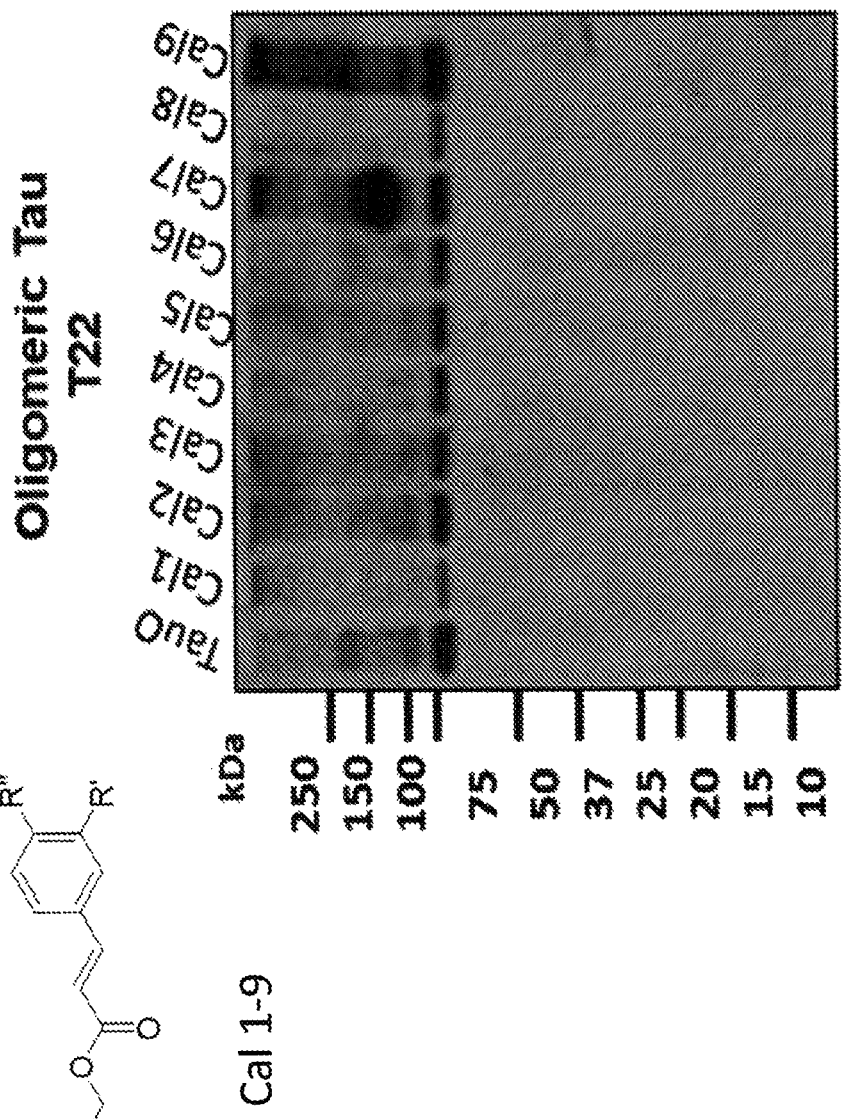
Figure 7A:
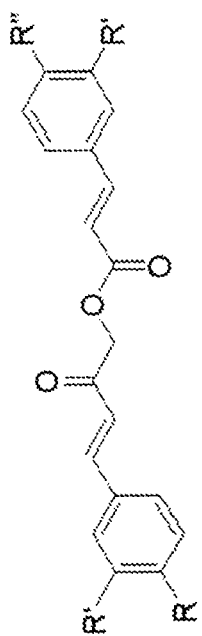
Figure 7B:
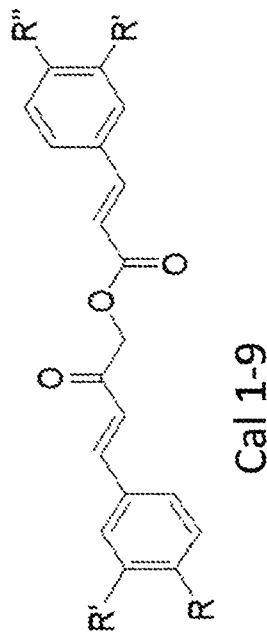
Figure 7B:
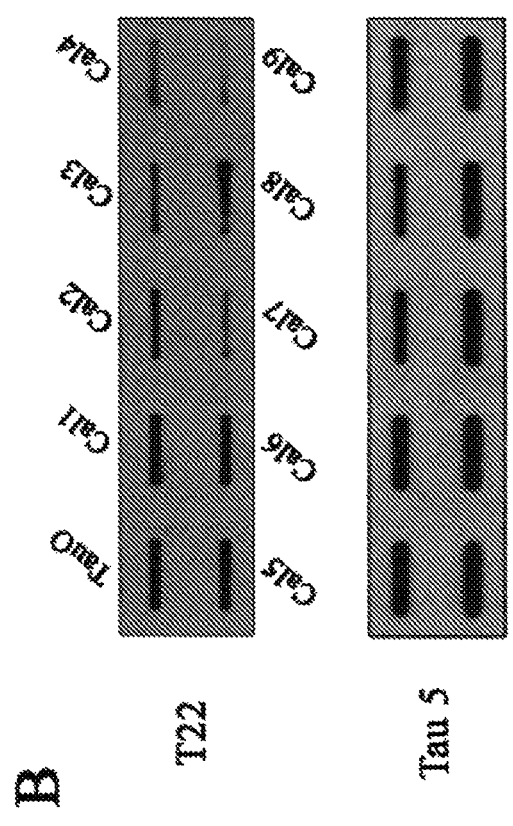
Figure 7B:
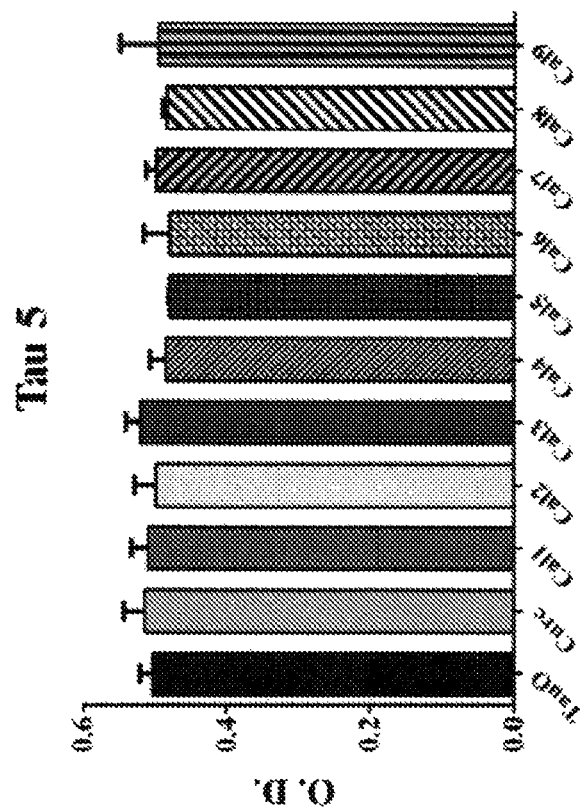
Figure 7C:
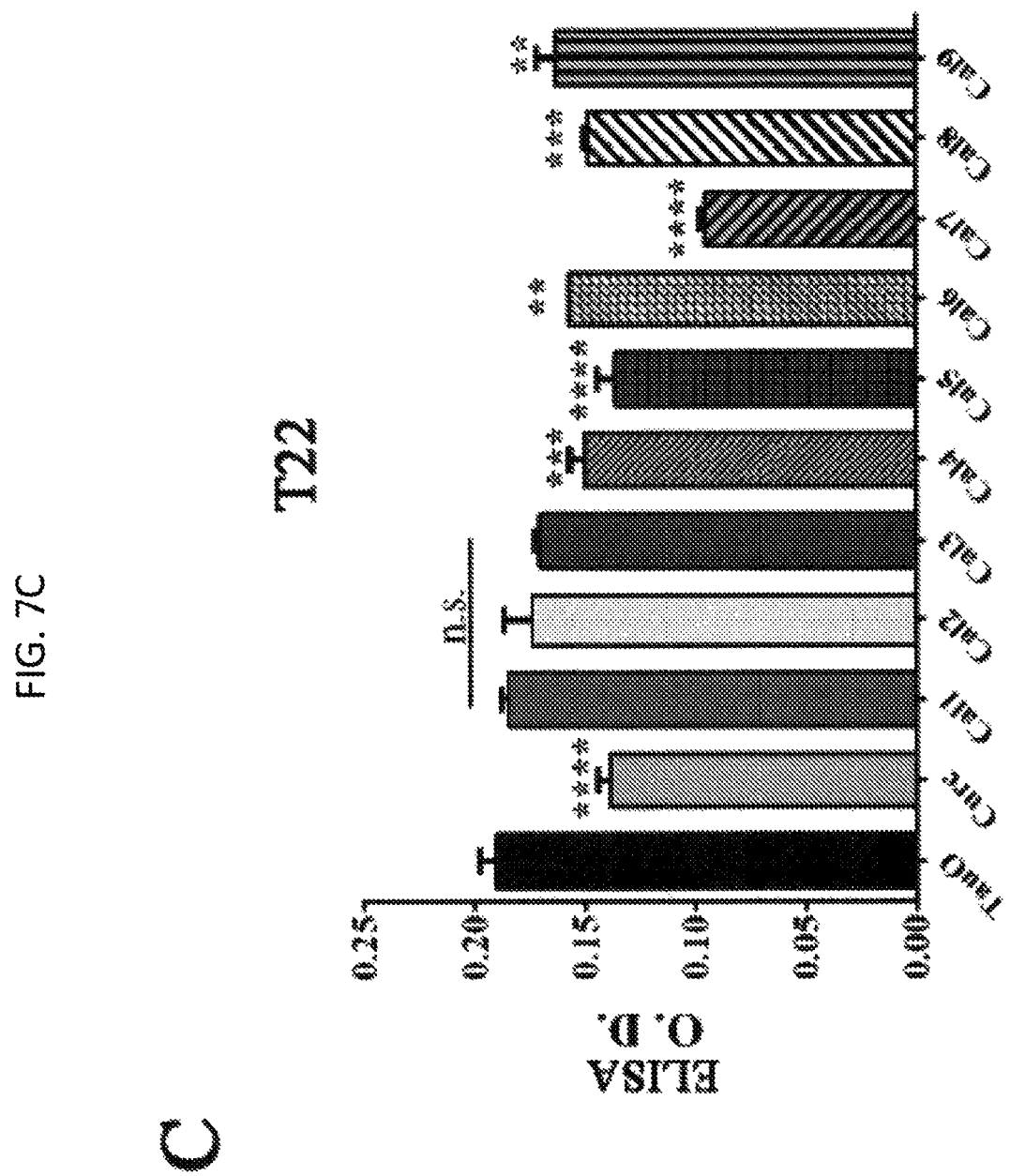

FIGS. 7A-C. Biochemical analysis of oligomeric Tau with and without Calebin-A (Cal) derivatives treatment.

(A) Western blot analysis of 3 µg/µl of tau oligomers alone and pre-treated with curcumin and Calebin-A analogs probed with T22, shows that the incubation with the compounds modulates the aggregation states of tau oligomers as compared to the untreated TauO. (B) Filter Trap assay, probed with T22 and Tau 5, show that some of the compounds are able to decrease T22 immunoreactivity as compared to the untreated TauO. (C) ELISA analysis of oligomeric tau after treatment with Cal derivatives shows that some of the compounds decrease tau oligomer levels as seen by the reduced T22 immunoreactivity and no changes in total tau protein using Tau 5. Data were compared by one-way analysis of variance (ANOVA) followed by Dunnett's multiple comparison test: (p<0.01; *p<0.001****p<0.0001) Bars and errors represent the mean and standard deviation.

Figure 8A:
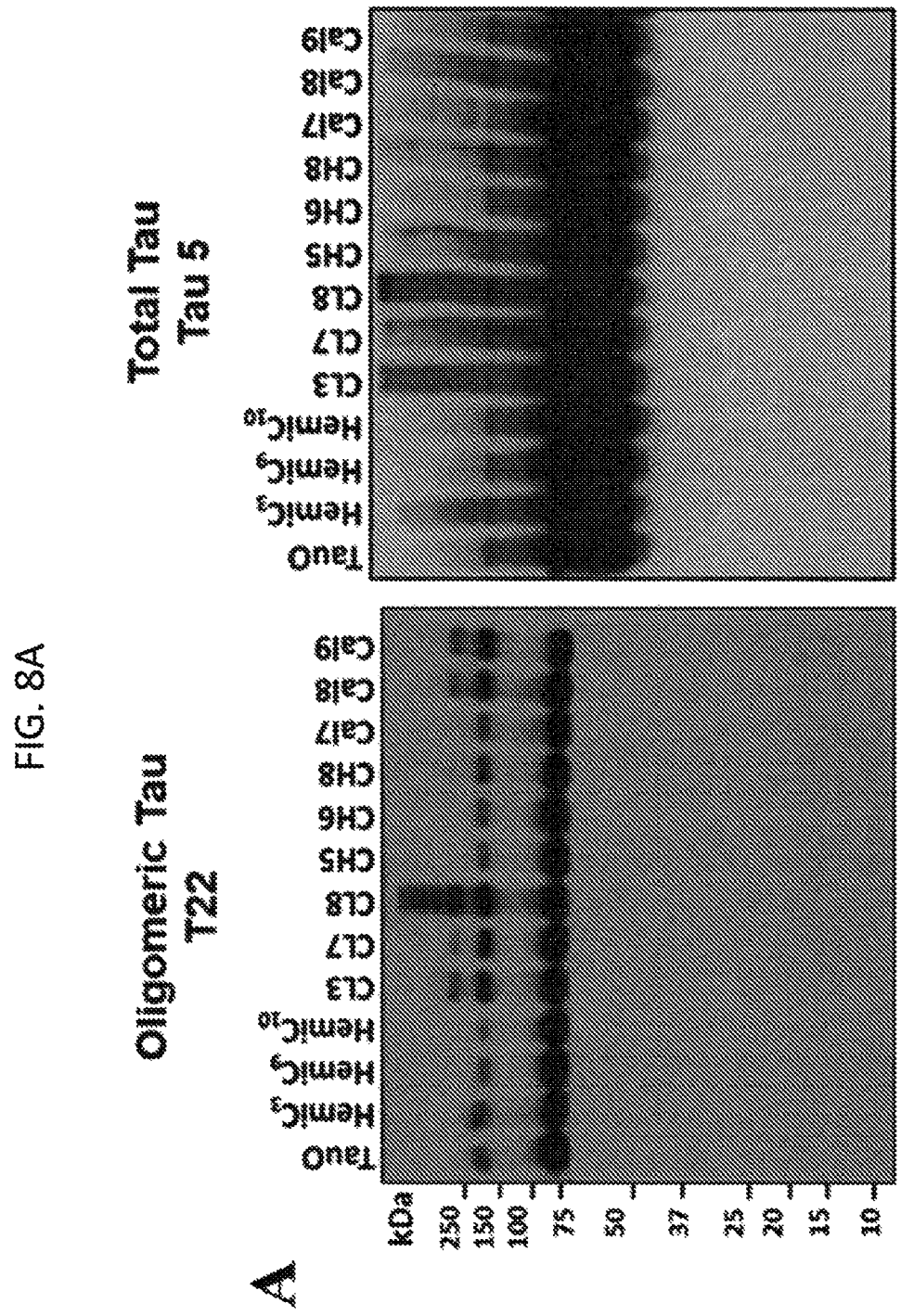
Figure 8B:
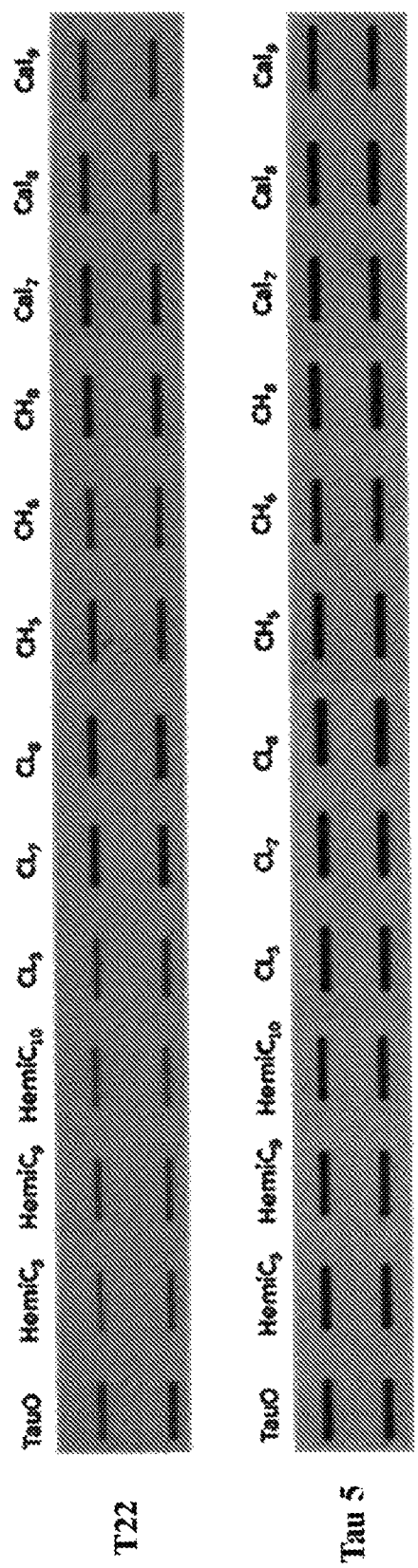

FIGS. 8A-C. Biochemical analysis of oligomeric tau with and without curcumin derivatives treatment.

(A) Western blot analysis of 3 µg/µl of tau oligomers alone and pre-treated with curcumin analogs probed with T22, shows that the incubation with the compounds modulates the aggregation states of preformed tau oligomers as compared to the untreated TauO. (B) Filter Trap assay of tau oligomers alone and pre-treated with curcumin derivatives probed with T22 and Tau 5. Some of the compounds are able to alter the aggregation state of preformed tau oligomers resulting in decreased T22 immunoreactivity as compared to the untreated TauO. (C) ELISA analysis of oligomeric tau after treatment with curcumin derivatives show that the selected compounds decrease tau oligomer levels as seen by the reduced T22 immunoreactivity and no changes in total tau protein by using Tau 5. Data were compared by one-way analysis of variance (ANOVA) followed by Dunnett's multiple comparison test: (*p<0.05; p<0.01; *p<0.001) Bars and errors represent the mean and standard deviation.

Figure 9A:
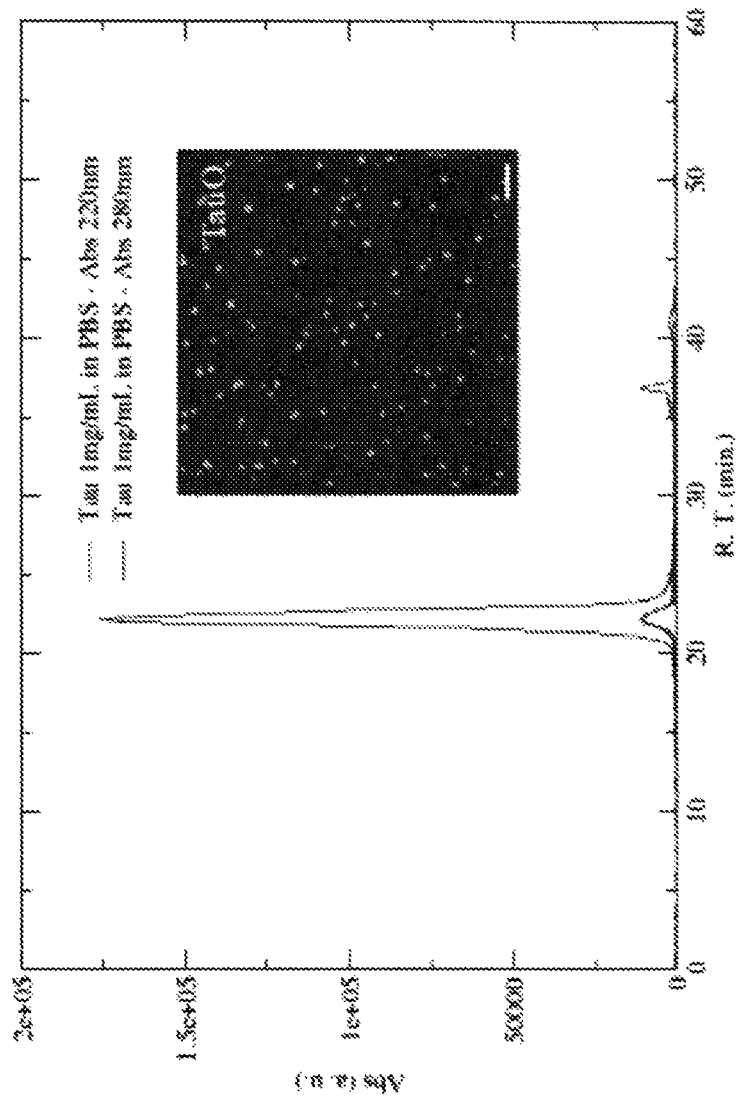
Figure 9B:
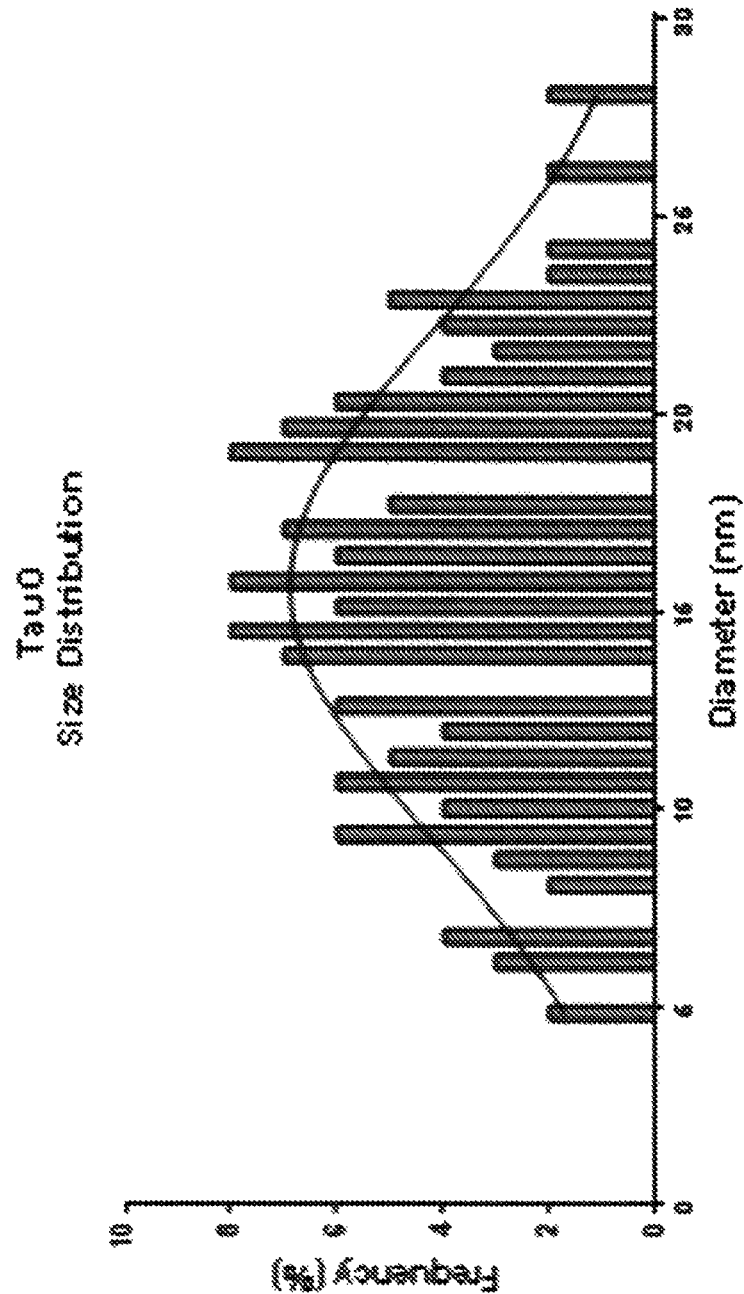
Figure 9C:
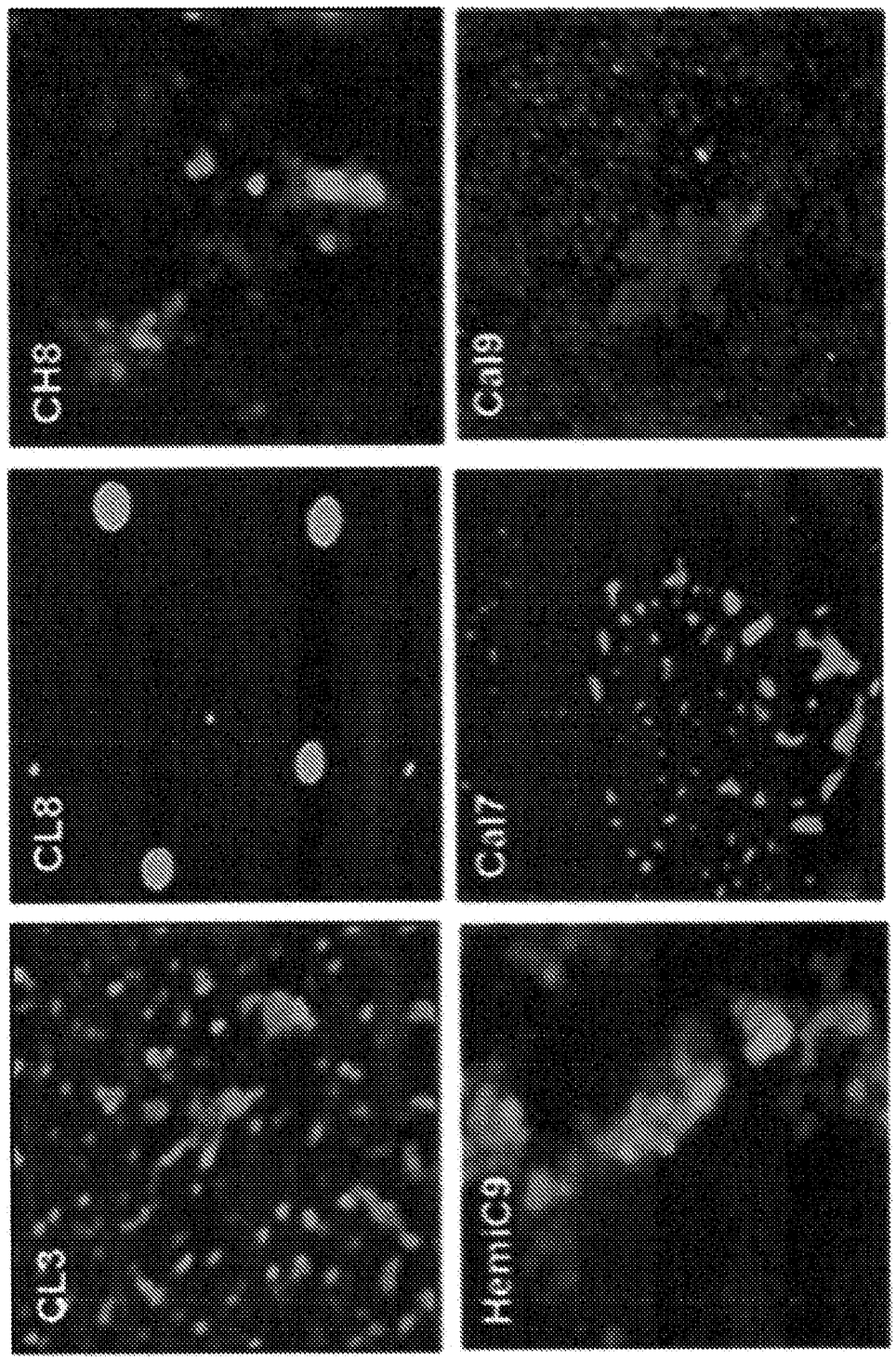

FIGS. 9A-C. Biophysical characterization of tau oligomers.

(A) FPLC chromatogram of tau oligomers; the main peak is ~120-150 kDa (tau dimer/trimer). (B) Size distribution histogram of TauO shows that the average diameter of the oligomers is 15.6±0.87. (C) Atomic Force Microscopy images of TauO after treatment with 5 µM of curcumin derivatives for CL3, CL8, CH8, HemiC9, Cal7 and Cal9. AFM analysis show the ability of the compounds to modulate TauO aggregation states converting TauO into much larger aggregates. Scale bars=100 nm.

Figure 10A:
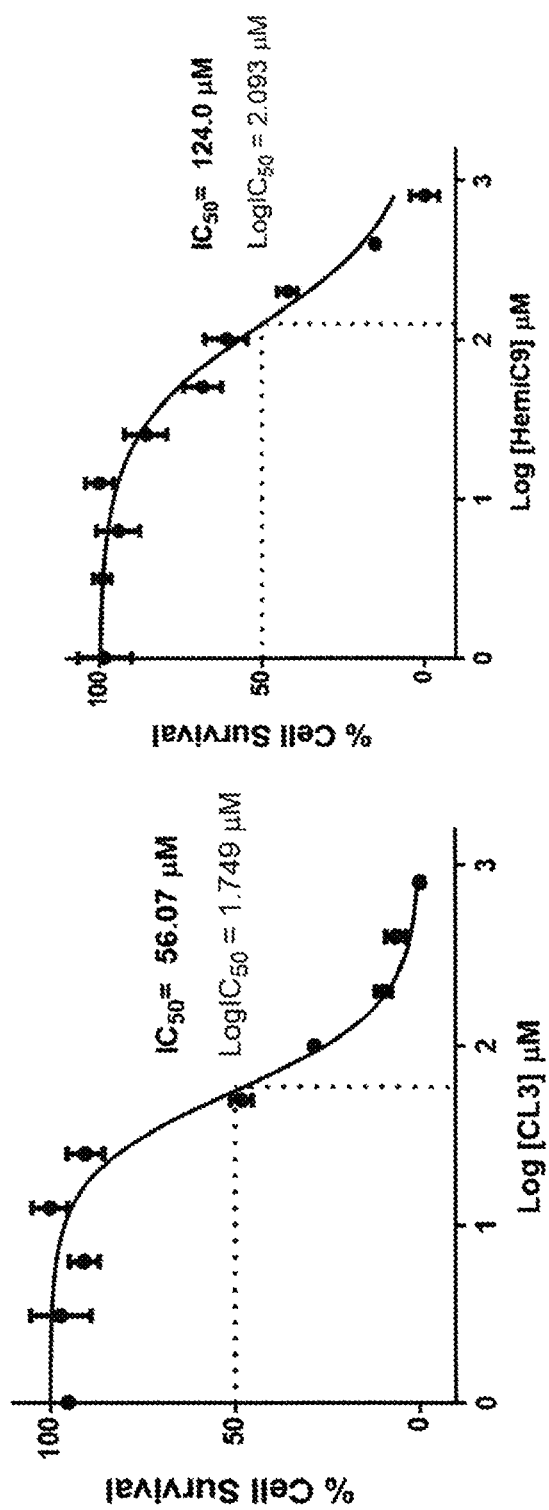
Figure 10B:
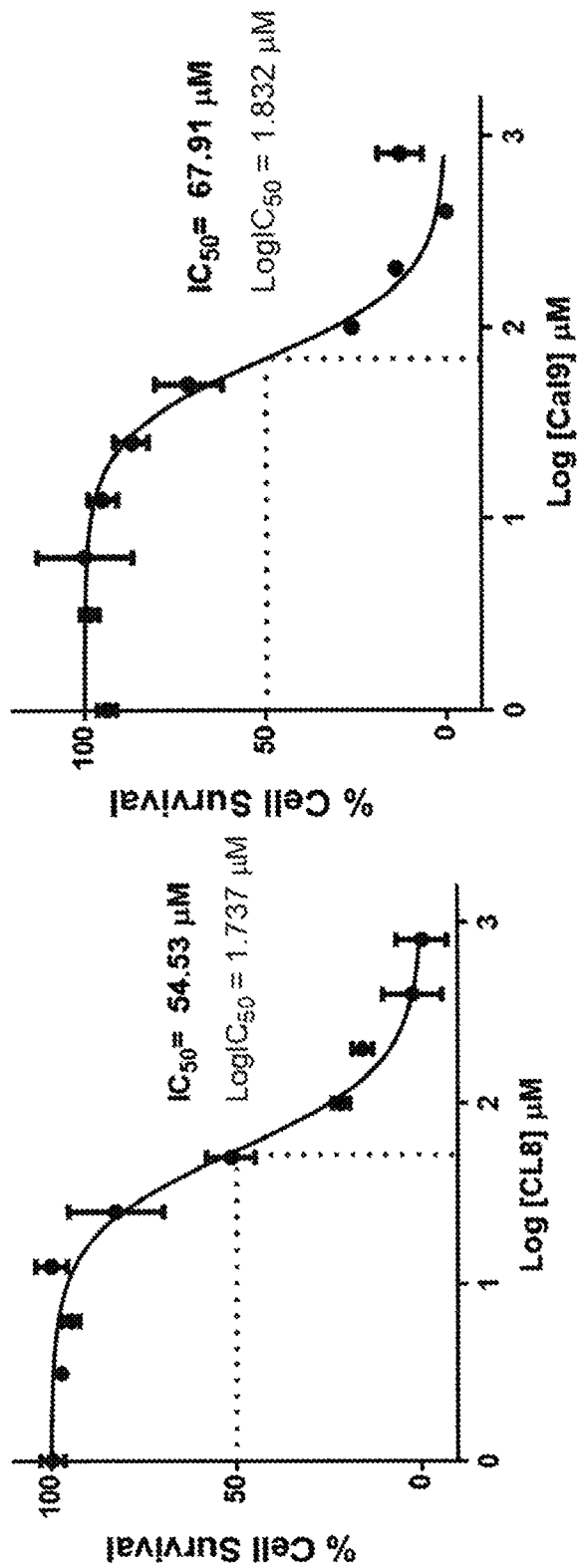
Figure 10C:
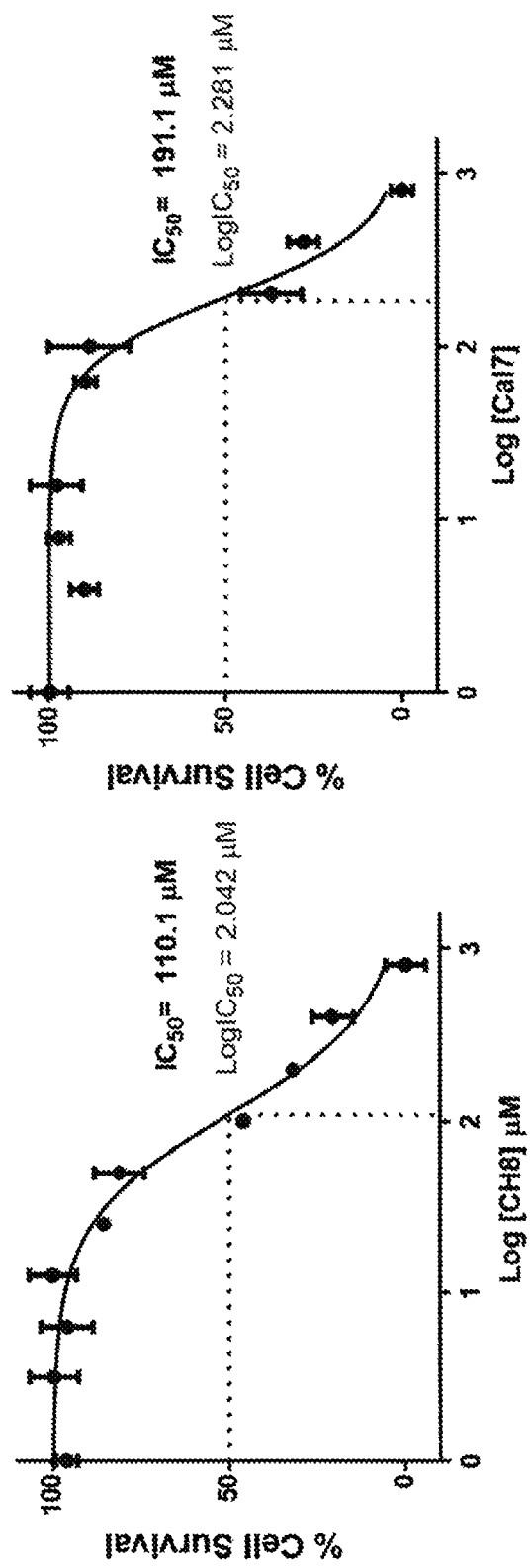

FIG. 10. Curcumin derivative effects on cell viability.

The cytotoxicity of curcumin derivatives on human neuroblastoma SH-SY5Y cell line was determined by MTT assay. MTT assay was used to determine the IC50 values for CL3, CL8, CH8, HemiC9, Cal7 and Cal9 compounds following treatment with increasing concentration of the compounds (0-800 µM) for 24 hours. Values are presented as the mean±SD (n=3).

FIGS. 11A-B. Curcumin derivative effects on primary cortical neurons cell viability.

(A) Viability percentage of neuronal culture exposed to 0.5 µM of tau oligomers, 0.5 µM of tau oligomers pre-incubated with 5 µM curcumin derivatives and controls for 2 hours. Cells exposed to TauO pre-treated with curcumin derivatives had significantly higher cells viability as compared to TauO alone. Data were compared by one-way analysis of variance (ANOVA) followed by Dunnett's multiple comparison test: Ctrl vs TauO §§§ p<0.001; TauO vs CL3, CL8, CH8, HemiC9, Cal7 and Cal9: *p<0.05; **p<0.01. Bars and errors represent the mean and standard deviation (n=3). (B) Viability percentage of neuronal culture exposed to 0.5 µM of Aβ oligomers (AβO), 0.5 µM of Aβ oligomers pre-incubated with 5 µM curcumin derivatives and controls. Cells exposed to AβO pre-treated with curcumin derivatives show no changes in cells viability as compared to AβO alone showing the selected curcumin derivatives were not able to rescue from AβO-induced toxicity. Data were compared by one-way analysis of variance (ANOVA) followed by Dunnett's multiple comparison test: Ctrl vs AβO, CL3, CL8, CH8, HemiC9, Cal7 and Cal9:

*p<0.05; p<0.01; *p<0.001. Bars and errors represent the mean and standard deviation (n=3).

Figure 12A:
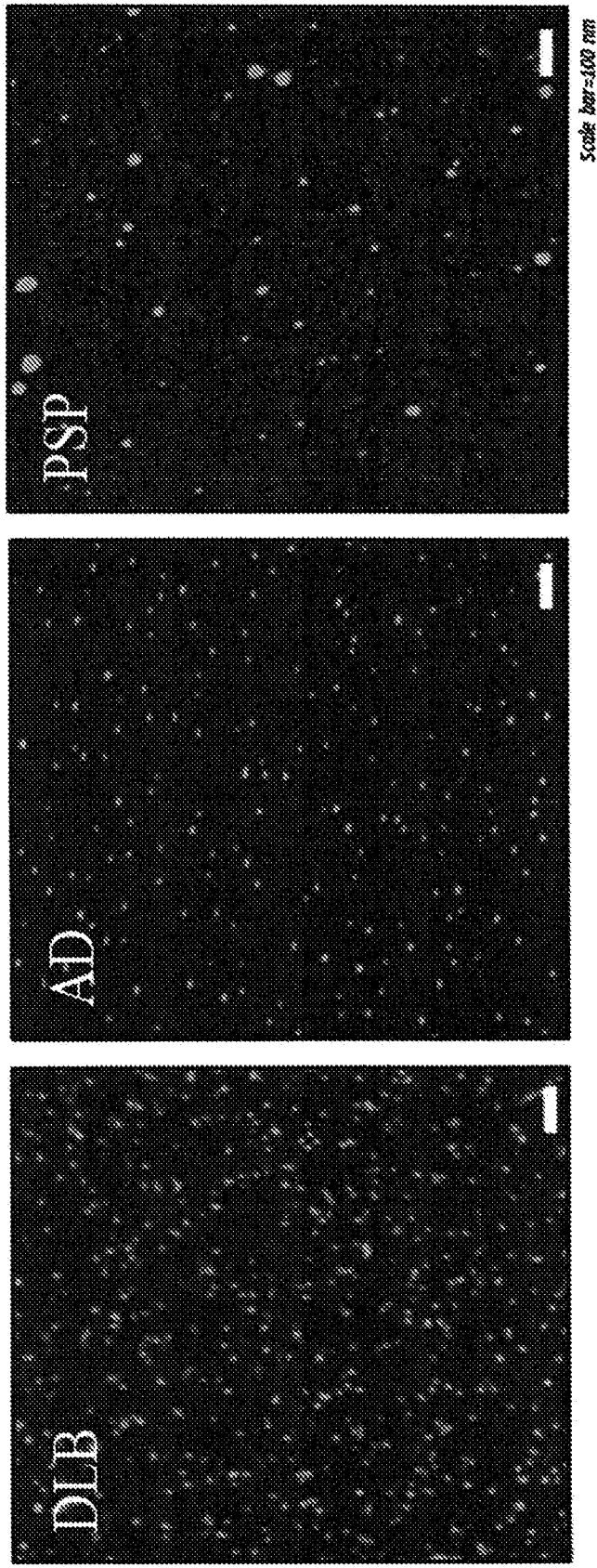

FIGS. 12A-C. Characterization of BDTOs (A) Brain-derived tau oligomers from different tauopathies were characterized by AFM showing different morphologies. Scale bars=100 nm. (B) BDTOs were evaluated by Western blot, probed with anti-tau antibody Tau5, before and after treatment with 1 μg/mL of PK. Western blot analysis revealed different patterns of fragmentation of each BDTO after exposure to PK digestion. (C) Viability percentage of cultured Htau primary neurons exposed to 0.5 μM of BDTOs. Primary neurons given BDTOs reduced significantly cells viability when compared to the untreated control. Data were compared by one-way analysis of variance (ANOVA) followed by Dunnett's multiple comparison test: (p<0.01; *p<0.001.) Bars and errors represent the mean and standard deviation.

FIGS. 13A-D. Biochemical analyses of PSP tau oligomers treated with Curcumin-like derivatives and untreated control.

(A) Western blots of BDTOs probed with total (Tau 5) and oligomeric (T22) tau antibodies showing decreased tau aggregates after treatment with CL analogs. (B) Western blot analysis, using T22, revealed a significant decrease in tau oligomer aggregates in the presence of the derived small molecules as compared to BDTOs alone. (C) BDTOs, alone and in the presence of CL small molecules, were exposed to PK digestion. Representative Western blot using anti-tau antibody Tau 5, revealed the ability of the analogs to affect the protein core stability as compared to BDTOs alone. (D) Direct ELISA analysis of BDTOs alone and in the presence of CL derivatives confirmed the CL's ability to modulate toxic BDTOs decreasing the oligomer levels. Data were compared by one-way analysis of variance (ANOVA) followed by Dunnett's multiple comparison test: (*p<0.05; p<0.01; *p<0.001; ****p<0.0001.) Bars and errors represent the mean and standard deviation.

Figure 1:
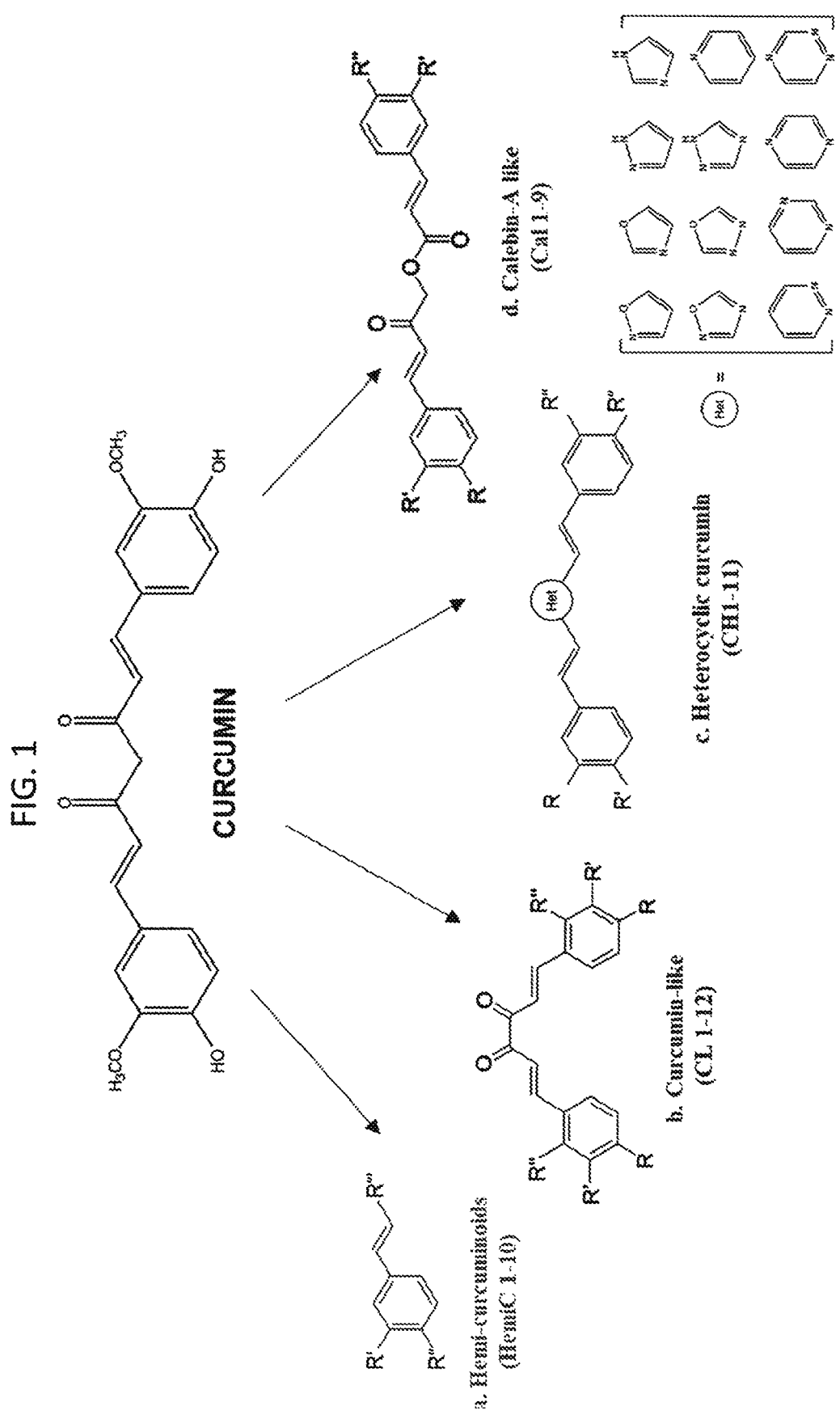
FIG. 1. Structure of curcumin and newly synthesized curcumin derivatives. The curcumin derivatives disclosed herein encompasses four different classes: Hemi-curcuminoids (a), Curcumin-like (b), Heterocyclic curcumin-like (c), and Calebin-A derivatives (d). The Heterocyclic curcumin-like can be synthesized by following Lipinski's rule of five to obtain active molecules able to easily across the brain blood barrier thus entering readily the brain.
Figures 1, 14A:
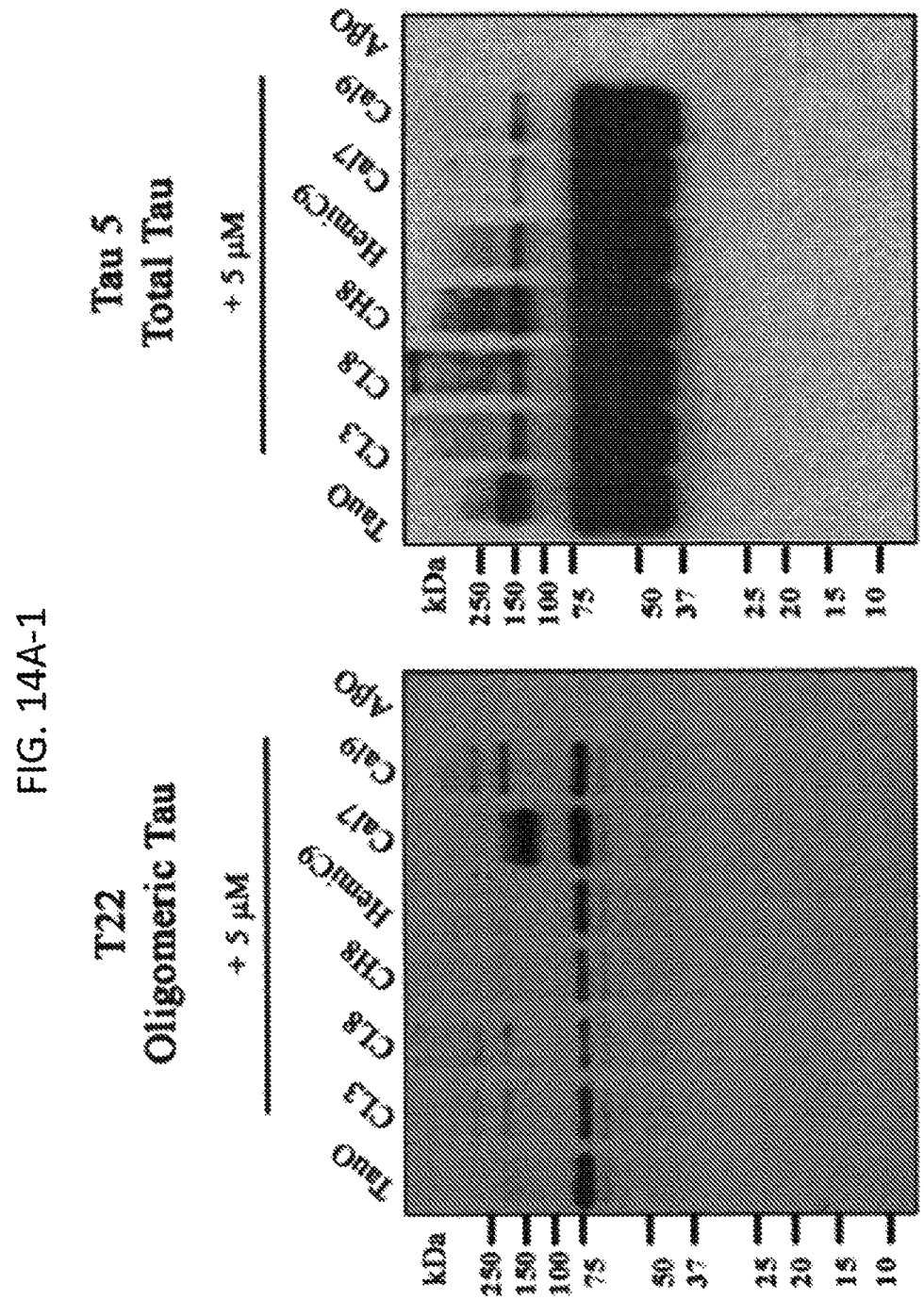
Figures 2, 14A:
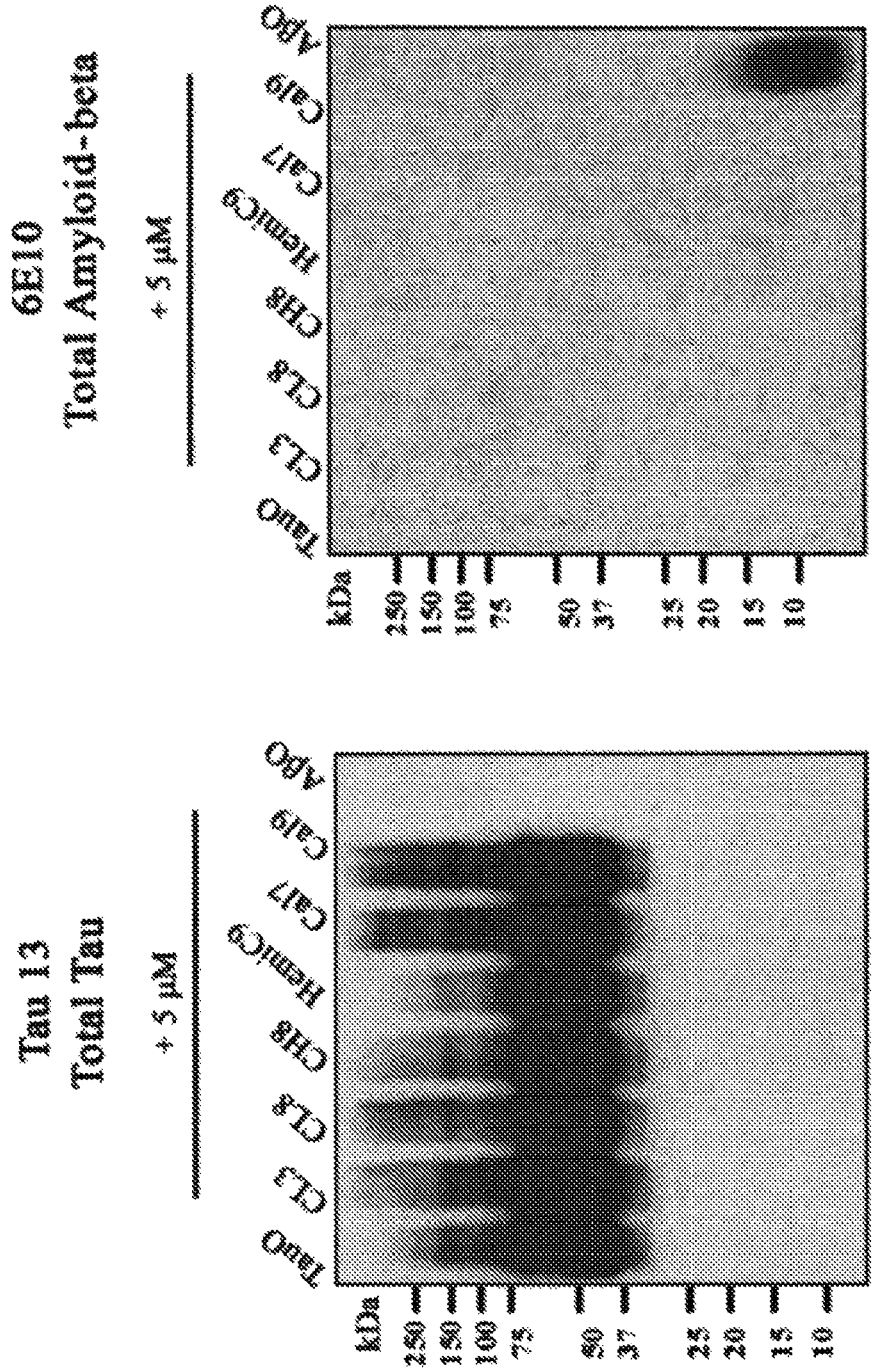
Figure 14E:
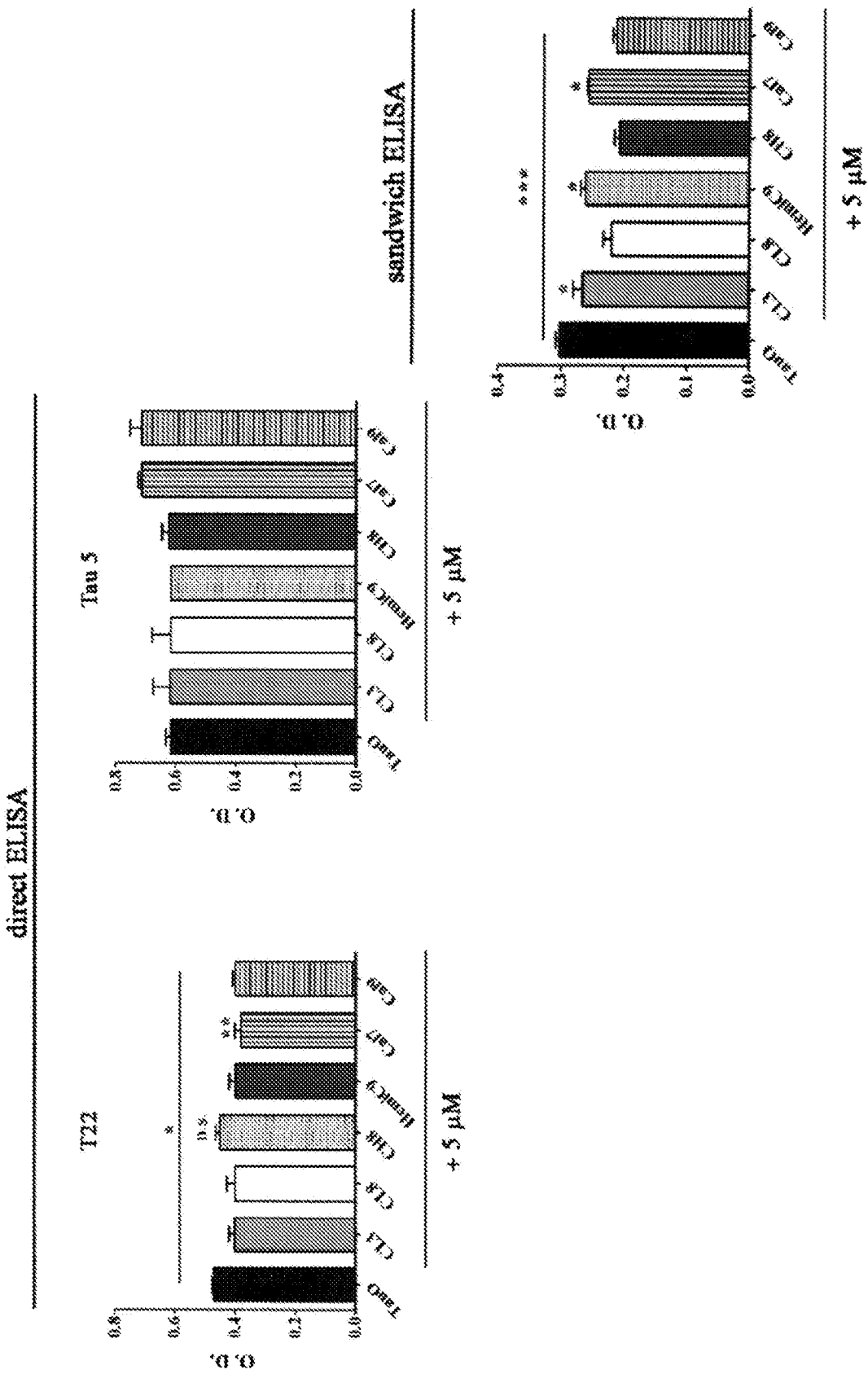

FIGS. 14A-1-2. Biochemical analyses of oligomeric tau with and without curcumin derivatives.

(A-1) Western blot of tau oligomers in the absence and presence of curcumin analogs (final concentration 5 μM) probed with the oligomeric tau antibody, T22 and total tau antibodies, Tau 5 and Tau 13 and the control anti-Aβ antibody, 6E10. (A-2) Western blot of tau oligomers in the absence and presence of curcumin analogs (final concentration 5 μM) probed with the oligomeric tau antibody, T22 and total tau antibodies, Tau 5 and Tau 13 and the control anti-Aβ antibody, 6E10.

FIGS. 14B-E. Biochemical analyses of oligomeric tau with and without curcumin derivatives.

(B) The incubation with the compounds modulates the aggregation states of preformed tau oligomers as seen by T22 quantification analysis. (C-D) Filter Trap assay of tau oligomers alone and pretreated with curcumin derivatives probed with T22 and Tau 5. Curcumin-derived small molecules alter the aggregation pathways of tau oligomers resulting in decreased T22 immunoreactivity as compared to the untreated TauO. (E) ELISA analyses shows that the selected compounds decrease tau oligomer levels as seen by the reduced T22 immunoreactivity and no significant changes in total tau protein as assessed by Tau 5 antibody. The reduction of tau oligomers was confirmed by sandwich ELISA, using T22 as capture antibody and Tau 5 as detection antibody. Data in B, D and E were compared by one-way analysis of variance (ANOVA) followed by Dunnett's multiple comparison test: *p<0.05; p<0.01; *p<0.001; ****p<0.0001. Bars and error bars represent the mean and standard deviation.

Figure 15B:
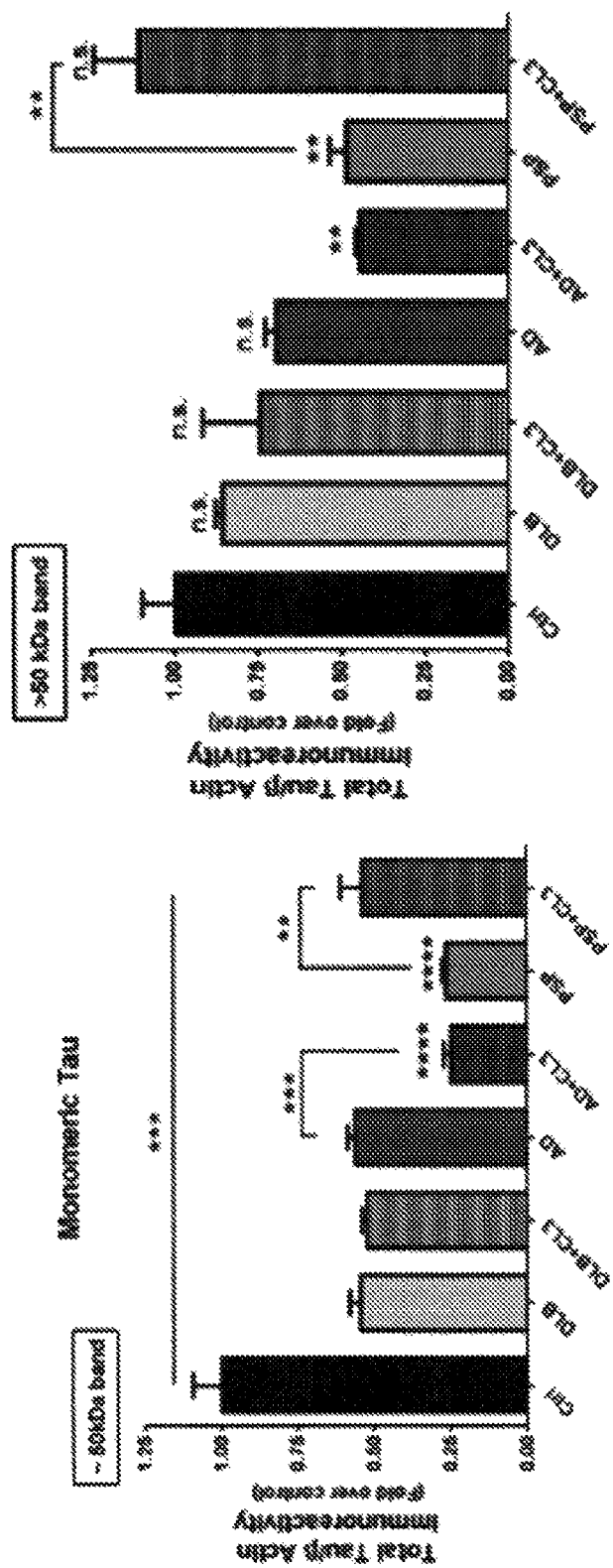

FIG. 15. Disease-relevant brain-derived tau oligomers with and without CL3 taken up by primary cortical neurons. Primary cortical neurons were exposed to 0.5 μM DLB, AD and PSP BDTOs in the presence and absence of 5 μM CL3 for 24 hrs. Tau levels are evaluated in the cytoplasmic fraction using the generic tau antibody, Total Tau. Western blot analyses showed that the exogenous addition of BDTOs to neurons seeds the recruitment of endogenous tau as shown by the significant decreased level of tau monomers upon treatment with BDTOs. The results suggest a strain-specific effect. PSP show to more efficiently decrease monomeric tau in the cytoplasmic fraction as compared to DLB and AD. The pretreatment of each BDTO with CL3 show to differently modulate their aggregation states as shown by their resulting effects on primary neurons. β-Actin is used as loading control. Data were compared by one-way analysis of variance (ANOVA) followed by Dunnett's multiple comparison test: Ctrl vs DLB, DLB+CL3, AD, AD+CL3, PSP, PSP+CL3: p<0.01; *p<0.001; ****p<0.0001. Bars and error bars represent the mean and standard deviation.

DESCRIPTION 1.0. Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977)), which is incorporated herein by reference in its entirety, for further examples of pharmaceutically acceptable salt).

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —(CH$_2$)$_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —NH$_2$ group.

An "amido" group refers to an —CONH$_2$ group. An alkylamido group refers to an —CONHR group wherein R is an alkyl group as defined above. A dialkylamido group refers to an —CONRR' group wherein R and R' are alkyl groups as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-CH$_2$— etc.

The term "phenyl vinyl double bond moiety" used in reference to Formulas I, II, III and IV (and pharmaceutical salts thereof) refers to double bond enclosed in area demarked by broken lines:

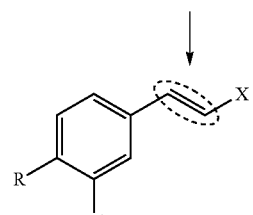

Formula I

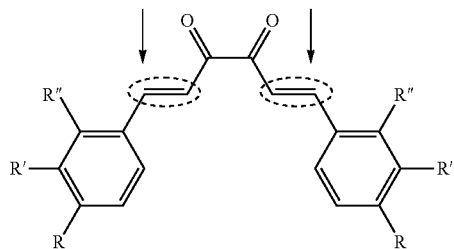

Formula II

9
-continued

Formula III

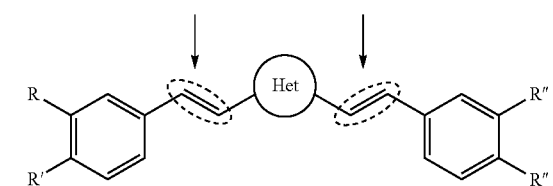

Formula IV

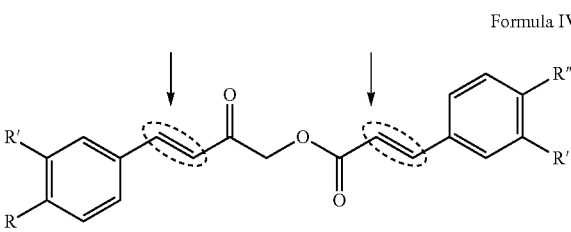

'Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)₂amino, alkylsulfinyl, alkyl sulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—C(O)NR₂), unsubstituted alkyl, unsubstituted heteroalkyl, alkoxy, alkylthio, alkylamino, (alkyl)₂amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —NH₂, —NH($C_{1-4}$alkyl), —N(C1-4alkyl)₂, —NO₂, —S($C_{1-4}$alkyl), —SO₂($C_{1-4}$alkyl), —CO₂($C_{1-4}$alkyl), and —O($C_{1-4}$alkyl).

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

It is to be understood that both the foregoing descriptions are exemplary, and thus do not restrict the scope of the invention.

10

2.0. Compounds

2.1 Hemi-Curcuminoids (HemiC 1-10)—Formula I

One aspect of the invention pertains to a compound of the Formula I and pharmaceutically acceptable salts thereof, wherein:

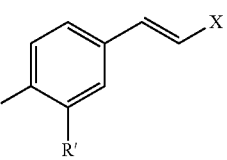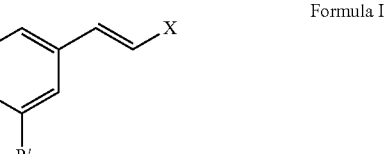

Formula I

R is OH, alkoxy, alkyl, dialkylamino, or —O-alcohol protecting group

R' is hydrogen, halogen, or alkoxy;

X is CO—R¹, CO₂R², COCH₂Y, CO₂H, or CN;

Y is chosen from halogen, OH, OR¹, NH₂, NHR₁, NR¹R², SH, and SR¹; and

Wherein R¹ and R² are independently $C_1$-$C_{10}$-alkyl.

In some embodiments, the phenyl vinyl double bond moiety of Formula I may have E or Z geometry.

In further embodiments, the invention encompasses compounds of the Formula I and pharmaceutically acceptable salts thereof, wherein the phenyl vinyl double bond moiety of Formula I has E geometry.

In further embodiments, the invention encompasses compounds of the Formula I and pharmaceutically acceptable salts thereof, wherein the phenyl vinyl double bond moiety of Formula I has Z geometry.

In some embodiments, the invention encompasses compounds of the Formula I and pharmaceutically acceptable salts thereof, wherein: R is OH, OMe, —NMe₂, —OMOM, or $C_1$-$C_{10}$-alkyl.

In further embodiments, the invention encompasses compounds of the Formula I and pharmaceutically acceptable salts thereof, wherein R' is H, Cl, or OMe.

In further embodiments, the invention encompasses compounds of the Formula I and pharmaceutically acceptable salts thereof, wherein X is COMe, CO₂Et, COCH₂I, COCH₂Br, COCH₂Cl, COCH₂F, CO₂H, or CN.

In further embodiments, the invention encompasses compounds of the Formula I and pharmaceutically acceptable salts thereof, X is COMe, CO₂Et, COCH₂I, COCH₂Br, COCH₂Cl, COCH₂F, CO₂H, or CN and wherein the phenyl vinyl double bond moiety of Formula I is in E configuration.

2.2 Curcumin-Like (CL 1-12)—Formula II

Another aspect of the invention pertains to compounds of Formula II and pharmaceutically acceptable salts thereof, wherein:

Formula II

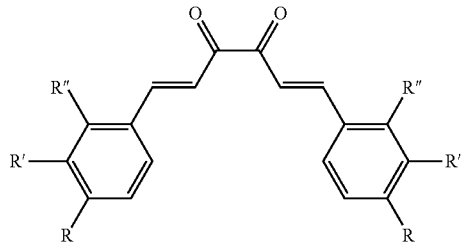

R is alkoxy, H, halogen, dialkyamino, —O-alcohol protecting group, or COOH;

R' is H, halogen, or alkoxy; and

R" is H or halogen.

In some embodiments, the phenyl vinyl double bond moieties of Formula II are independently E or Z geometry.

In further embodiments, the invention encompasses compounds of the Formula II and pharmaceutically acceptable salts thereof, wherein both the phenyl vinyl double bond moieties of Formula II have E geometry.

In further embodiments, the invention encompasses compounds of the Formula II and pharmaceutically acceptable salts thereof, wherein both the phenyl vinyl double bond moieties of Formula II have Z geometry.

In further embodiments, the invention encompasses compounds of the Formula II and pharmaceutically acceptable salts thereof, wherein one phenyl vinyl double bond moiety of Formula II has Z geometry and the other phenyl vinyl double bond moiety of Formula II has E geometry.

In some embodiments, the invention encompasses compounds of the Formula II and pharmaceutically acceptable salts thereof, wherein:

R is —OMe, H, F, NMe$_2$, Cl, OMOM, or COOH;

R' is H, F, or OMe; and

R" is H or Cl.

In some embodiments, the invention encompasses compounds of the Formula II and pharmaceutically acceptable salts thereof, wherein:

R is —OMe, H, F, NMe$_2$, Cl, OMOM, or COOH;

R' is H, F, or OMe;

R" is H or Cl and the phenyl vinyl double bond moieties of Formula II are both in E configuration In some embodiments, the invention encompasses compounds of the Formula II and pharmaceutically acceptable salts thereof, wherein R,R' is —OCH$_2$O—.

In some embodiments, the invention encompasses compounds of the Formula II and pharmaceutically acceptable salts thereof, wherein R and R' are independently C$_1$-C$_6$ alkoxy.

2.3 Heterocyclic Curcumin-Like (CH 1-11)—Formula III

Another aspect of the invention pertains to compounds of Formula III and pharmaceutically acceptable salts thereof, wherein:

Formula III

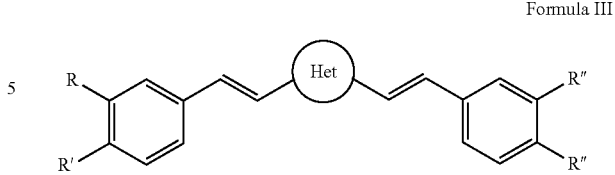

R is alkoxy, H, halogen, NMe$_2$ or —O-alcohol protecting group;

R' is alkoxy, H, or halogen;

R" is alkoxy, H, or halogen; and is chosen from:

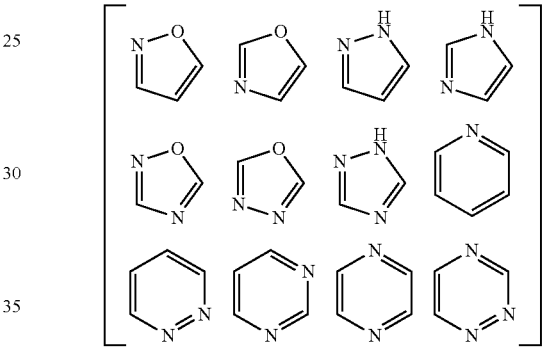

In some embodiments, the invention encompasses compounds of the Formula III and pharmaceutically acceptable salts thereof, wherein the "phenyl vinyl double bond moiety" is independently either E or Z independently.

In further embodiments, the invention encompasses compounds of the Formula III and pharmaceutically acceptable salts thereof, wherein both the phenyl vinyl double bond moieties of Formula III have E geometry.

In further embodiments, the invention encompasses compounds of the Formula III and pharmaceutically acceptable salts thereof, wherein both the phenyl vinyl double bond moieties of Formula III have Z geometry.

In further embodiments, the invention encompasses compounds of the Formula III and pharmaceutically acceptable salts thereof, wherein one phenyl vinyl double bond moiety of Formula III has Z geometry and the other phenyl vinyl double bond moiety of Formula III has E geometry.

In some embodiments, the invention encompasses compounds of the Formula III and pharmaceutically acceptable salts thereof, wherein R is OMe, H, F, Cl, NMe$_2$ or OMOM;

R' is OMe, H, F, or Cl; and

R" is OMe H, F, or Cl.

In some embodiments, the invention encompasses compounds of the Formula III and pharmaceutically acceptable salts thereof, wherein:

R is OMe, H, F, Cl, NMe$_2$ or OMOM;

R' is OMe, H, F, or Cl;

R" is OMe H, F, or Cl; and both "phenyl vinyl double bond" moieties are both in E configuration.

In some embodiments, the invention encompasses compounds of the Formula III and pharmaceutically acceptable salts thereof, wherein R,R' is —OCH₂O—.

In some embodiments, the invention encompasses compounds of the Formula III and pharmaceutically acceptable salts thereof, wherein:

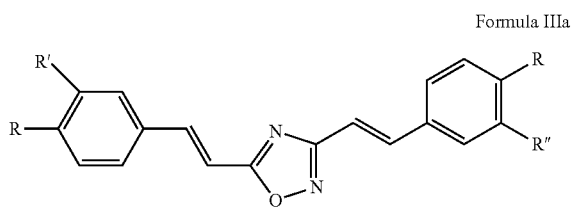

Formula IIIa

R is OMe, H, F, Cl, NMe₂ or OMOM;
R' is OMe, H, F, or Cl; and
R" is OMe or H.

In some embodiments, the invention encompasses compounds of the Formula III and pharmaceutically acceptable salts thereof, wherein:

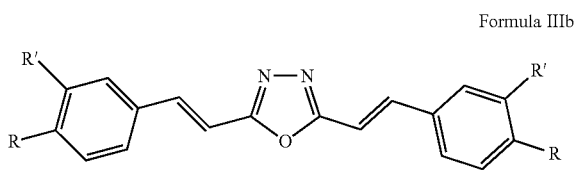

Formula IIIb

R is OMe, H, F, Cl, NMe₂ or OMOM; and
R' is OMe, H, F, or Cl.

2.4 Calebin-A Analogs (Cal 1-9)—Formula IV

Another aspect of the invention pertains to compounds of Formula IV and pharmaceutically acceptable salts thereof, wherein:

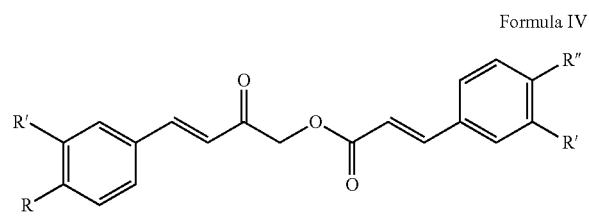

Formula IV

R is alkoxy, alkyl, halogen, OH, or —O-alcohol protecting group;
R' is alkoxy or H; and
R" is alkoxy, alkyl, OH, or halogen.

In some embodiments, the invention encompasses compounds of the Formula IV and pharmaceutically acceptable salts thereof, wherein the "phenyl vinyl double bond moiety" is independently either E or Z independently.

In further embodiments, the invention encompasses compounds of the Formula IV and pharmaceutically acceptable salts thereof, wherein both the phenyl vinyl double bond moieties of Formula IV have E geometry.

In further embodiments, the invention encompasses compounds of the Formula IV and pharmaceutically acceptable salts thereof, wherein both the phenyl vinyl double bond moieties of Formula IV have Z geometry.

In further embodiments, the invention encompasses compounds of the Formula IV and pharmaceutically acceptable salts thereof, wherein one phenyl vinyl double bond moiety of Formula IV has Z geometry and the other phenyl vinyl double bond moiety of Formula IV has E geometry.

In some embodiments, the invention encompasses compounds of the Formula IV and pharmaceutically acceptable salts thereof, wherein
R is OMe, Me, OH, F, Cl, or OMOM;
R' is OMe or H; and
R" is OMe, Me, OH, F, or Cl.

In some embodiments, the invention encompasses compounds of the Formula IV and pharmaceutically acceptable salts thereof, wherein:
R is OMe, Me, OH, F, Cl, or OMOM;
R' is OMe or H;
R" is OMe, Me, OH, F, or Cl and
wherein both "phenyl vinyl double bond" moieties are both in E configuration.

In some embodiments, the invention encompasses compounds of the Formula IV and pharmaceutically acceptable salts thereof, wherein R,R' is —OCH₂O—.

In some embodiments, the invention encompasses compounds of the Formula IV and pharmaceutically acceptable salts thereof, wherein R',R" is —OCH₂O.

3.0. Method of Use

Certain exemplary embodiments of the invention were synthesized and screened against preformed tau oligomers in order to test their ability in altering and modulating the aggregation state of toxic tau oligomers by further promoting their aggregation and formation of larger tau structures with decreased toxicity. Indeed, for a long time the research has been focusing on biologically active inhibitor small molecules that could either inhibit tau aggregates assembly or disassemble pre-existing tau aggregates, rather than small molecules that could promote the formation of non-toxic high molecular weight aggregates.

The inventors found that curcumin analogs may modulate the aggregation pathways of tau oligomers leading to the formation of larger non-toxic tau aggregates. Toxicity screens were assessed using cultured primary cortical neurons isolated from embryos of Htau mice, expressing non mutant human tau. Indeed, the treatment with the selected active curcumin derivatives shows to protect primary cortical neurons from tau oligomer-induced toxicity, while the same compounds were not able to rescue neurons from Aβ oligomers-induced toxicity. In addition, internalization screens using SH-SY5Y human neuroblastoma cell line showed that the compounds are able to affect the preformed tau oligomers internalization, mechanism that mediates their uptake by cells.

Another aspect of the invention pertains to a method of detecting tau oligomers, comprising:
introducing into a subject a detectable quantity of a compound of the invention or a pharmaceutically-acceptable salt thereof;
after introducing the compound, allowing sufficient time (e.g. about 16 hours) for tau oligomers present in the subject to form compound-tau aggregates having a molecular mass of at least 100000 daltons; and
detecting the compound-aggregates in the subject.

In some embodiments, after introducing the compound, the method encompasses allowing sufficient time (e.g. up to about 16 hours) for tau oligomers present in the subject to form compound-tau aggregates (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 34, 37, 38, 39, 40, 41, 42, 43, 44, 45, 46, 47, 48, 49, 50, 51, 52, 53, 54, 55, 56, 57, 58, 59, 60 minutes, or at least 12 hours, 16 hours, 24 hours, or 48 hours).

Another aspect of the invention pertains to a method of detecting tau oligomers, comprising:
introducing into a subject a detectable quantity of a compound of the invention or a pharmaceutically-acceptable salt thereof;
after introducing the compound, allowing sufficient time (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 34, 37, 38, 39, 40, 41, 42, 43, 44, 45, 46, 47, 48, 49, 50, 51, 52, 53, 54, 55, 56, 57, 58, 59, 60 minutes, or at least 12 hours, 16 hours, 24 hours, or 48 hours) for tau oligomers present in the subject to form compound-tau aggregates having a molecular mass between 100000 daltons to 500000 daltons; and detecting the compound-aggregates in the subject.

The present invention encompasses a method of detecting tau oligomers wherein detecting the compound-tau aggregates comprises generating at least one image of at least a portion of the subject.

The present invention encompasses a method of detecting tau oligomers wherein detecting the compound-tau aggregates comprises generating at least one image of at least a portion of the subject, and wherein said at least one image comprises a PET image or a MR image.

The present invention encompasses a method of detecting tau oligomers wherein detecting the compound-tau aggregates comprises generating at least one image of at least a portion of the subject, and
wherein the "at least a portion" comprises a portion of the brain of the subject.

Another aspect of the invention pertains to a method of detecting tau oligomers, comprising:
introducing into a subject a detectable quantity of a compound of the invention or a pharmaceutically-acceptable salt thereof;
after introducing the compound, allowing sufficient time (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 34, 37, 38, 39, 40, 41, 42, 43, 44, 45, 46, 47, 48, 49, 50, 51, 52, 53, 54, 55, 56, 57, 58, 59, 60 minutes, or at least 12 hours, 16 hours, 24 hours, or 48 hours) for tau oligomers present in the subject to form compound-tau aggregates having a molecular mass of at least 100000 daltons; and detecting the compound-aggregates in the subject,
wherein detecting the compound-tau aggregates comprises detecting a quantity of said aggregates.

Another aspect of the invention pertains to a method of detecting tau oligomers, comprising:
introducing into a subject a detectable quantity of a compound of the invention or a pharmaceutically-acceptable salt thereof;
after introducing the compound, allowing sufficient time (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 34, 37, 38, 39, 40, 41, 42, 43, 44, 45, 46, 47, 48, 49, 50, 51, 52, 53, 54, 55, 56, 57, 58, 59, 60 minutes, or at least 12 hours, 16 hours, 24 hours, or 48 hours) for tau oligomers present in the subject to form compound-tau aggregates having a molecular mass of at least 100000 daltons; and detecting the compound-aggregates in the subject,
wherein detecting the compound-tau aggregates comprises detecting a location of the compound-tau aggregates (e.g., within the brain tissue).

Another aspect of the invention pertains to a method of detecting tau oligomers, comprising:
introducing into a subject a detectable quantity of a compound of the invention or a pharmaceutically-acceptable salt thereof;
after introducing the compound, allowing sufficient time (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 34, 37, 38, 39, 40, 41, 42, 43, 44, 45, 46, 47, 48, 49, 50, 51, 52, 53, 54, 55, 56, 57, 58, 59, 60 minutes, or at least 12 hours, 16 hours, 24 hours, or 48 hours) for tau oligomers present in the subject to form compound-tau aggregates having a molecular mass of at least 100000 daltons; and detecting the compound-aggregates in the subject,
wherein detecting the compound-tau aggregates in the subject comprises detecting the aggregates in vivo.

A further aspect of the invention pertains to a tau PET tracer comprising one or more compounds of Formulas I, II, III, IIIa, IIIb, or IV, or pharmaceutical acceptable salts thereof.

A further aspect of the invention pertains to an imaging agent comprising a tau PET tracer comprising one or more compounds of Formulas I, II, III, IIIa, IIIb, or IV, or pharmaceutical acceptable salts thereof.

A further aspect of the invention pertains to a method of enhancing weak imaging signals of small oligomers comprising administering an imaging agent comprising a tau PET tracer comprising one or more compounds of Formulas I, II, III, IIIa, IIIb, or IV, or pharmaceutical acceptable salts thereof, to a subject.

Method for diagnosing, estimating the severity of, or monitoring the progression of dementia disease in a patient In some embodiments, the present invention encompasses a method for diagnosing, estimating the severity of, or monitoring the progression of dementia disease in a patient, comprising:
(a) administering to the patient a detectable amount of one or more compounds of Formulas I, II, III, IIIa, IIIb, IV, or a pharmaceutically acceptable salt thereof;
(b) imaging the brain of the patient to generate a brain image showing a distribution and relative amounts of said compound(s) in the brain; and
(c) relating the brain image of the patient to the presence or absence and/or degree of severity of progression of said dementia.

In some embodiments, said dementia is Alzheimer's disease. In further embodiments, the method for diagnosing, estimating the severity of, or monitoring the progression of dementia disease, encompasses administering said compound(s) used in said method intravenously.

The present invention encompasses a method for diagnosing, estimating the severity of, or monitoring the progression of dementia disease, wherein the imaging comprises performing PET or SPECT.

Furthermore, the present invention encompasses a method for diagnosing, estimating the severity of, or monitoring the progression of dementia disease, wherein said patient is a human dementia patient.

In some embodiments, the present invention encompasses a method of treating a tauopathy comprising administering one or more compounds of Formulas I, II, III, IIIa, IIIb, IV (or a pharmaceutical acceptable salt thereof) to a subject.

Furthermore, the present invention encompasses a method of treating a tauopathy, wherein said tauopathy is Alzheimer's disease, Progressive supranuclear palsy, or Lewy body with dementia.

The present invention encompasses a method of treating a tauopathy, wherein the tauopathy is treated by at least protecting the patient's primary cortical neurons from tau oligomer-induced toxicity.

4.0 Examples

Methods

All solvent and reagents were used as received, unless otherwise stated. Melting points were determined on a hot-stage apparatus. 1H-NMR and 13C-NMR spectra were recorded at indicated frequencies, residual solvent peak was used as reference. Chromatography was performed by using silica gel (0.040-0.063 mm) and mixtures of ethyl acetate and petroleum ether (fraction boiling in the range of 40-60° C.) in various ratios (v/v). All solvent and reagents were used as received. Compounds 2a, b, e, g (Wang, Yin et al. 2008), 3a, b, e, g (Wang, Yin et al. 2008), 2c [Vander Jagt, D. L.; Deck, L. M.; Abcouwer, S. F.; Bobrovnikova-Marjon, E.; Weber, W. M. US Patent 20060276536], 2d (Zhu, Mao et al. 2017), 4k (Battisti, Palumbo Piccionello et al. 2017), 5a (DiBiase, Lipisko et al. 1979) 5h (Khurana, Ali et al. 2014), CL1-3,5 (Sinu, Padmaja et al. 2013), 7 (List, Doehring et al. 2006, Battisti, Palumbo Piccionello et al. 2017), 8 (Rehse and Brehme 1998, Battisti, Palumbo Piccionello et al. 2017), $CH_4$ (Battisti, Palumbo Piccionello et al. 2017) were prepared as previously reported. Other already known compounds, prepared adapting previously reported methods as indicated below, present melting points and 1H-NMR spectra consistent with those reported in the cited literature.

Preparation of Tau Oligomers

Recombinant tau protein (tau-441 (2N4R) (MW 45.9 kDa) was expressed and purified as described (Margittai, M. 2004; Margittai, M. 2006). Tau pellet was treated with 8M urea followed by overnight dialysis against 1× phosphate-buffered saline (PBS) pH 7.4. Tau concentration was measured using bicinchoninic acid protein assay (Micro BCA kit, Pierce) and normalized to 1 mg/ml by adding 1× PBS. Aliquots of tau monomer in PBS were stored at −20° C. Each 300 µl of tau stock (0.3 mg) was added to 700 µl of 1× PBS, final concentration (0.3 mg/ml). 7 µL of Aβ42 oligomers (0.3 mg/ml) were added as seeds and the sample was mixed by pipetting for 1 minute. The sample was then incubated at room temperature on an orbital shaker. After shaking, the resulting tau oligomers were purified by fast protein liquid chromatography (FPLC).

Western Blotting

Pre-cast NuPAGE 4-12% Bis-Tris Gels for SDS-PAGE (Introvigen) were loaded with 3 µg of recombinant tau for each sample per well along with molecular weight marker. After being separated by electrophoresis, proteins were transferred to nitrocellulose membranes. Membranes were then blocked with 10% nonfat milk in Tris-buffered saline with very low tween 0.01% (TBS-T) overnight at 4° C. The next day membranes were probed with T22 (1:250) for tau oligomers and tau5 (1:10000) for total tau, diluted in 5% nonfat milk for 1 hour at RT. Membranes were then incubated with horseradish peroxidase-conjugated IgG anti-rabbit (1:10000) and anti-mouse (1:10000) secondary antibodies to detect, T22 and Tau5, respectively. ECL plus (GE Healthcare) was used for signal detection. Densitometric analysis of each band was quantified using Image J and analyzed by one-way ANOVA.

Dot Blot

The dot blot assay was performed as previously described (Lasagna-Reeves, Castillo-Carranza et al. 2010), to detect tau oligomers in the absence and presence of small molecules. Briefly, 1.5 µl of each end-product reaction was applied onto nitrocellulose membranes and then blocked with 10% nonfat milk in TBS-T overnight at 4° C. Next day, membranes were probed with T22 (1:250) for immunoreactivity with tau oligomers and Tau5 (1:10000) for total tau, diluted in 5% nonfat milk for 1 hour at RT. Membranes were then washed three time with TBS-T and incubated with horseradish peroxidase-conjugated IgG anti-rabbit (1:10000) and anti-mouse (1:10000) secondary antibodies to detect, T22 and Tau5, respectively. Blots were then washed three times in TBS-T and exposed to ECL plus (GE Healthcare) was used for signal detection. Densitometric analysis of each band was quantified using Image J.

Direct ELISA

ELISA assay was conducted as previously described (Lasagna-Reeves, Castillo-Carranza et al. 2010). Briefly, 96 well plates were (Nunc immobilizer, amino modules, Thermo Fisher Scientific Waltham, MA) previously coated with 1.5 µLof tau oligomers in the presence and absence of curcumin and curcumin derivatives using 50 µL of 1× PBS, pH 7, as coating buffer. After washing three times with TBS-T, plates were blocked for 1 hour at 37° C. with 120 µl of 10% non-fat milk in TBS-T. Plates were then washed three times with TBS-T, before probing with 100 µL of primary antibodies for 1 hour at 37° C., T22 (diluted 1:250 in 5% non-fat milk in TBS-T) and Tau 5 (diluted 1:10000 in 5% non-fat milk in TBS-T), respectively. Plates were then washed three times with TBS-T, and probed with 100 µL of horseradish peroxidase-conjugated anti-rabbit or anti-mouse IgG (Promega, Madison, WI) (diluted 1:10000 in 5% non-fat milk in TBS-T). After 1 hour of incubation at 37° C., plates were washed three times with TBS-T and developed with 3, 3, 5, 5-tetramethylbenzidine (TMB-1component substrate, KPL, Gaithersburg, MD). The reaction was stopped by using 100 µL 1M HCl and samples were read at 450 nm using POLARstar OMEGA plate reader. All measurements were performed in triplicate

Filter Trap Assay

Filter Trap assay was performed to detect tau oligomers in the absence and presence of small molecules. Briefly, 1 µg of each end-product reaction was applied onto nitrocellulose membranes, previously embedded with TBS-T, through the use of a vacuum based bio-slot apparatus. Membranes were then blocked with 10% nonfat milk in TBS-T overnight at 4° C. Next day, membranes were probed with the oligomer-specific tau antibody, T22 (1:250) and total tau antibody, Tau5 (1:10000) diluted in 5% nonfat milk for 1 hour at RT. Membranes were then washed three time with TBS-T and incubated with horseradish peroxidase-conjugated IgG anti-rabbit (1:10000) and anti-mouse (1:10000) secondary antibodies to detect, T22 and Tau5, respectively. Membranes were washed three time in TBS-T and ECL plus (GE Healthcare) was used for signal detection. Densitometric analysis of each band was quantified using Image J and analyzed by two-way ANOVA multiple comparisons, performed using GraphPad Prism 6.01.

MTT

Human neuroblastoma SH-SY5Y cells were maintained in Dulbecco's modified Eagle's medium (DMEM) and grown to confluence in 96-well plates. Cells ($\approx$10,000 cells/well) were treated both with 2.0 µM tau oligomers and 2.0 µM tau oligomers pre-incubated with 5 µM of curcumin and curcumin derivatives. Cells viability was corrected by the vehicle background. All measurements were performed in triplicate. The cytotoxic effect was determined using 3-(4,5-dimethylthiazol-2-yl)-2,5-diphenyltetrazolium bromide (MTT) assay for assessing cell viability following manufacturers' instructions. Optical density (OD) was measured at 490 nm with POLARstar OMEGA plate reader (BMG Labtechnologies). Cell viability was calculated as the percentage of the OD value of treated cells compared with untreated controls, according to the following equation: Viability=(OD SAMPLE/OD CONTROL)×100. Statistical analysis was based on one-way analysis of variance (ANOVA), performed using GraphPad Prism 6.01.

Atomic Force Microscopy

Tau oligomers were characterized by AFM as previously described (Lasagna-Reeves, (2010)0. Briefly, samples were prepared by adding 10 µl tau oligomers in the absence and presence of AC on freshly-cleaved mica and were allowed to adsorb to the surface. Mica were then washed three times with distilled water to remove unbound protein and impurities followed by air-drying. Samples were then imaged with Multimode 8 AFM machine (Veeco, CA) using a non-contact tapping method (ScanAsyst-Air).

Preparation of TauO

Recombinant tau protein (tau-441 (2N4R) MW 45.9 kDa) was expressed and purified as described (Margittai and Langen 2004, Margittai and Langen 2006). The tau pellet was treated with 8M urea followed by overnight dialysis against 1× phosphate-buffered saline (PBS) pH 7.4. Tau concentration was measured using bicinchoninic acid protein assay (Micro BCA kit, Pierce) and normalized to 1 mg/ml by adding 1× PBS. Aliquots of tau monomer in PBS were stored at −20° C. Each 300 µl of tau stock (0.3 mg) was added to 700 µl of 1× PBS and incubated for 1 hour on an orbital shaker at room temperature. After shaking, the resulting tau oligomers were purified by fast protein liquid chromatography (FPLC, Superdex 200HR 10/30 column, Amersham Biosciences).

Preparation of Tau Oligomers in Presence of Small Molecules

A volume of 100 µl of tau oligomers (1 µg/µl) was incubated with Curcumin (1:5; 1:10 molar ratio) and curcumin derivatives (1:5 molar ratio). Compounds were dissolved in ETOH 75%/DMSO (5:1) at a final concentration of 5 mM and diluted in 1× PBS or ddH$_2$O for incubation or toxicity assay (final concentration 5 µM). Tau oligomers in the presence of the small molecules and controls were incubated on an orbital shaker, without stirring, for 16 hours under oligomerization conditions as previously described (Lo Cascio and Kayed 2018).

Preparation of Aβ Oligomers

Aβ oligomers (AβO) were prepared as previously described (Lasagna-Reeves, Castillo-Carranza et al. 2010) by dissolving 0.3 mg of Aβ pellet in 200 µL of hexafluoroisopropanol (HFIP) and incubating for 10-20 min at room temperature. The resulting solution was added to 700 µL of ddH$_2$O in a siliconized Eppendorf tube with holes placed on top of the cap to allow the slow evaporation of HFIP. The samples were then stirred at 500 rpm using a Teflon-coated micro stir bar for 48 hours at room temperature in the fume hood.

Preparation of Aβ Oligomers in the Presence of Small Molecules

A volume of 100 µl of Aβ oligomers (0.5 µg/µl) was incubated with curcumin derivatives (final concentration 5 µM). Compounds were dissolved in ETOH 75%/DMSO (5:1) at a final concentration of 5 mM and diluted in 1× PBS or ddH$_2$O for incubation or toxicity assay (final concentration 5 µM). Aβ oligomers in the presence of the small molecules and controls were incubated on an orbital shaker, without stirring, for 16 hours under oligomerization conditions as previously described (Lo Cascio and Kayed 2018).

Western Blotting

An amount of 3 µg of each sample were resolved on a pre-cast NuPAGE 4-12% Bis-Tris Gels for SDS-PAGE (Invitrogen) and transferred to nitrocellulose membranes. Then membranes were blocked with 10% nonfat milk in Tris-buffered saline with very low tween 0.01% (TBS-T) overnight at 4° C. Next day, membranes were probed with T22 (1:250) for tau oligomers and Tau 5 (1:10000) and Tau 13 (1:50.000) for total tau, diluted in 5% nonfat milk for 1 hour at RT. Membranes were then incubated with horseradish peroxidase-conjugated IgG anti-rabbit (1:10000) to detect T22 and anti-mouse (1:10000) secondary antibody to detect Tau 5 and Tau 13. ECL plus (GE Healthcare) was used for signal detection.

Dot Blot

Dot blot assay to detect tau oligomers in the absence or presence of small molecules was performed as previously described (Lasagna-Reeves, Castillo-Carranza et al. 2010), to detect tau oligomers in the absence and presence of small molecules. Briefly, 1.5 µl of each end-product reaction was applied onto nitrocellulose membranes and then blocked with 10% nonfat milk in TBS-T overnight at 4° C. Next day, membranes were probed with the oligomer-specific tau antibodies, T22 (1:250) and TOMA1 (1:200), respectively polyclonal and monoclonal tau antibodies, and total tau antibody Tau 5 (1:10000), diluted in 5% nonfat milk for 1 hour at RT. Membranes were then incubated with horseradish peroxidase-conjugated IgG anti-rabbit (1:10000) to detect T22 and anti-mouse (1:10000) secondary antibody to detect Tau 5 and TOMA1. Blots were then washed three times in TB S-T and ECL plus (GE Healthcare) was used for signal detection.

Densitometric analysis of each band was quantified using Image J and analyzed by two-way ANOVA followed by Dunnett's multiple comparisons test, performed using GraphPad Prism 6.01.

Direct ELISA

ELISA assay was conducted as previously described (Lasagna-Reeves, Castillo-Carranza et al. 2010). Briefly, 96 well plates (Nunc immobilizer, amino modules, Thermo Fisher Scientific Waltham, MA) were previously coated with 1.5 µl of tau oligomers in the presence or absence of curcumin and curcumin derivatives using 50 µl of 1× PBS, pH 7.4, as coating buffer. After washing three times with TBS-T, plates were blocked for 1 hour at 37° C. with 120 µl of 10% non-fat milk in TBS-T. Plates were then washed three times with TBS-T, and probed with 100 µl of primary antibodies for 1 hour at 37° C., T22 (diluted 1:250 in 5% non-fat milk in TBS-T) and Tau 5 (diluted 1:10000 in 5% non-fat milk in TBS-T). Plates were then washed three times with TBS-T, and incubated with 100 µl of horseradish peroxidase-conjugated anti-rabbit or anti-mouse IgG (Promega, Madison, WI), diluted 1:10000 in 5% non-fat milk in TBS-T, for 1 hour at 37° C. Plates were washed three times with TBS-T and developed with 3, 3, 5, 5-tetramethylbenzidine (TMB-lcomponent substrate, KPL, Gaithersburg, MD). The reaction was stopped using 100 µl of 1M HCl and absorbance was read at 450 nm using POLARstar OMEGA plate reader. All experiments were performed in triplicate.

Sandwich ELISA

Sandwich ELISA assay was conducted as previously described (Castillo-Carranza, Sengupta et al. 2014). Briefly ELISA plates (Nunc Immobilizer Amino Plate, 442404, Thermo Fisher Scientific) were coated with the capture antibody, T22 (1:250) diluted in sodium bicarbonate buffer, pH 9.6. The plate was incubated at 4° C. overnight. The following day, after washing two times with TBS-T, plates were blocked for 2 hours at 37° C. with 120 µL of 10% nonfat milk in TBS-T. The plate was then loaded with 2 µg of recombinant tau oligomers in PBS and added to each well for 90 minutes at 37° C. Plates were then washed three times with TBS-T, and probed with 100 µL of anti-tau antibody, Tau 5 (diluted 1:10000 in 5% nonfat milk in TBS-T) for 1 hour at room temperature. After washing three times with TBS-T, plate were incubated with of 100 µL of HRP-conjugated anti-mouse IgG, diluted 1:10000 in 5% nonfat milk in TBS-T, for 1 hour at room temperature. Plates were washed three times with TBS-T and developed with 3,3,5, 5-tetramethylbenzidine (TMB+Substrate-Chromogen, S1599, Dako). The reaction was stopped using 100 µL of 1M HCl and absorbance was read at 450 nm using POLARstar OMEGA plate reader. All experiments were performed in triplicate.

Filter Trap Assay

Filter Trap assay was performed using Bio-Dot® SF Microfiltration Apparatus (Bio-Rad) as previously described (Lo Cascio and Kayed 2018). Briefly, 1 µg of each end-product reaction was applied onto nitrocellulose membranes, previously pre-wetted with TBS-T, through the use of a vacuum based bio-slot apparatus. Membranes were then blocked with 10% nonfat milk in TBS-T overnight at 4° C. Next day, membranes were probed with the oligomer-specific tau antibodies, T22 (1:250) and TOMA1 (1:200), respectively polyclonal and monoclonal tau antibodies, and total tau antibody Tau 5 (1:10000), diluted in 5% nonfat milk for 1 hour at RT. Membranes were then incubated with horseradish peroxidase-conjugated IgG anti-rabbit (1:10000) to detect T22 and anti-mouse (1:10000) secondary antibody to detect Tau 5 and TOMA1. Membranes were washed three time in TBS-T and ECL plus (GE Healthcare) was used for signal detection.

Densitometric analysis of each band was quantified using Image J and analyzed by two-way ANOVA followed by Dunnett's multiple comparisons test, performed using GraphPad Prism 6.01.

Cell Toxicity Assay—MTT

Human neuroblastoma SH-SY5Y cells were maintained in Dulbecco's modified Eagle's medium (DMEM) and grown to confluence in 96-well plates. Cells ($\approx$10,000 cells/well) were treated both with 2.0 µM tau oligomers and 2.0 µM tau oligomers pre-incubated with 5 µM of curcumin or curcumin derivatives. Cells viability was corrected by the vehicle background. All measurements were performed in triplicate. The cytotoxic effect was determined using 3-(4, 5-dimethylthiazol-2-yl)-2,5-diphenyltetrazolium bromide (MTT) assay for assessing cell viability following manufacturer's instructions. Optical density (OD) was measured at 490 nm with POLARstar OMEGA plate reader (BMG Labtechnologies). Cell viability was calculated as the percentage of the OD value of treated cells compared with untreated controls, according to the following equation: Viability=(OD SAMPLE/OD CONTROL)×100. Statistical analysis was based on one-way analysis of variance (ANOVA), performed using GraphPad Prism 6.01.

Morphological Analysis of TauO by AFM

Tau oligomers were characterized by AFM as previously described (Lasagna-Reeves, Castillo-Carranza et al. 2010). Briefly, samples were prepared by adding 10 µl tau oligomers in the absence or presence of AC on freshly-cleaved mica and were allowed to adsorb to the surface. Mica were then washed three times with distilled water to remove unbound protein and impurities followed by air-drying. Samples were then imaged with Multimode 8 AFM machine (Veeco, CA) using a non-contact tapping method (ScanAsyst-Air).

Isolation of Brain-Derived Tau Oligomers (BDTOs)

Oligomeric tau strains were isolated from brain extract by immunoprecipitation (Lasagna-Reeves 2012, Gerson, Castillo-Carranza et al. 2016). Tosyl-activated magnetic Dyna-beads (Dynal Biotech) were coated with 20 µg of anti-tau oligomer-specific polyclonal antibody T22, diluted in 0.1 M of borate, pH 9.5 overnight at 37° C. Next, the beads were washed in 0.1% Bovine serum albumin in 0.2 M Tris-HCl, pH 8.5 and then incubated with brain homogenates with rotation at room temperature for 1 hour. Then beads are washed three time in 1× PBS, pH 7.4 and eluted using 0.1 M glycine, pH 2.8. Next, pH was adjusted using 1 M Tris-HCl, pH 8.0 and fractions were then centrifuged in a microcon centrifugal filter device, 25 kDa molecular weight cut-off (Millipore) at 14,000×g for 25 min at 4° C. Tau concentration was measured using bicinchoninic acid protein assay (Micro BCA kit, Pierce).

Brain-Derived Tau Oligomers in Presence of Small Molecules

A volume of 100 µl of BDTOs (0.5 µg/µl) was incubated with curcumin derivatives (final concentation 5 µM). Compounds were dissolved in ETOH 75%/DMSO (5:1) at a final concentration of 5 mM and diluted in 1× PBS or ddH$_2$O for incubation or toxicity assay (final concentration 5 µM). Tau oligomers in the presence of the small molecules and controls were incubated on an orbital shaker, without stirring, for 16 hours under oligomerization conditions.

Characterization of Brain-Derived Tau Oligomers

Immunoprecipitated tau oligomers were characterized using various biochemical methods as previously described (Lasagna-Reeves 2012, Gerson, Castillo-Carranza et al. 2016). AFM was performed to visualize the morphologies of oligomeric assemblies of isolated proteins. Isolated oligomers (5 µL) were injected into an LC-6AD Shimadzu HPLC system fitted with a TSK-GEL G3000 SWXL (30 cm×7.8 mm) column, Supelco-808541 to determine the size of the isolated oligomers. PBS (pH 7.4) was used as the mobile phase with a flow rate of 0.5 mL/min. A gel filtration standard (Bio-Rad 51-1901) was used for calibrations. Samples (0.8-1 µg) were also tested for their comparative bis-ANS and ThT binding.

Proteinase K Digestion

In an Eppendorf tube, molecular grade water, Tris HCl and sodium chloride were added so that the final concentrations for these two buffers became 100 mM and 5 mM, respectively in the entire solution volume. Next tau oligomeric species were added and mixed. Lastly, the PK enzyme was added (final concentration 1 µg/ml). Then, the sample tubes were incubated at 37° C. for 1 h. The enzymatic reaction was stopped by adding 4× sample buffer. Samples were then ready to be loaded in the SDS-PAGE gel for electrophoresis or stored at −80° C.

Primary Cortical Neurons

Primary cortical neurons from transgenic mice expressing human full-length tau were prepared and maintained as described previously (Beaudoin, Lee et al. 2012). Briefly, cortical neurons were isolated from embryos at embryonic day 16-18 using Accutase solution (Sigma). Dissociated neurons were plated at a density of 30×10$^4$ cells/well in 96-well plates containing high glucose Dulbecco's Modified Eagle Medium (DMEM, Corning) supplemented with 2% B27 (Gibco), 10,000 units/mL penicillin, 10,000 µg/mL streptomycin , and 25 µg/mL Amphotericin B (Gibco). After 2 hours, plating medium was removed from cells and replaced with Neurobasal medium (Gibco) plus 2% B27, 0.5 mL L-glutamine (Hyclone), 10,000 units/mL, 10,000 µg/mL streptomycin, and 25 µg/mL Amphotericin B supplement. Cells were grown for 10-12 days in vitro before experiments and 50% of media changes were performed every 3 days. On day 10, neuronal cultures were treated with 0.5 µM BDTOs alone and in the presence of Curcumin derivative (at final concentration 5 µM) for two hours. The MTT viability assay was performed as previously described (Cell Toxicity Assay—MTT).

Immunofluorescence

SH-SY5Y cells were maintained in Dulbecco's modified Eagle's medium (DMEM) and grown to confluence using poly-L-lysine coated coverslip in 24-well plates as previously described (Castillo-Carranza, Guerrero-Munoz et al. 2018, Sengupta, Montalbano et al. 2018). Cells (≈20,000 cells /well) were treated for 1 hour with 0.5 µM TauO labeled with Alexa Fluor 568 or 0.5 µM TauO labeled with Alexa Fluor 568 pretreated with 5 µM of curcumin derivatives. After washing off unbound proteins, cells were stained with 5 µg/mL WGA (Wheat Germ Agglutinin) Alexa Fluor 488 for 10 min followed by fixation in chilled methanol. After washing three times with 1× PBS, cells were permeabilized with 0.25% Triton-X 100, diluted in 1× PBS for 10 min. After washing three times with PBS (10 min each), cells were then stained with DAPI (Vector Laboratories) and mounted using Prolong Gold Antifade mounting media. Slides were then dried in fume hood. Cells were imaged with Keyence BZ-800 Microscope using standard filters for DAPI, GFP and Texas Red channels and analyses have been conducted using BZ—X Analyzer software. Nikon 100× oil immersion objective was used for capture images that were analyzed by ImageJ and statistical analysis was performed by one-way ANOVA followed by Student's T test, using GraphPad Prism 6.01.

Results and Discussion

The effect of curcumin on toxic tau aggregates was evaluated using our in vitro preparation of tau oligomers. Therefore, highly purified oligomeric tau species were incubated with and without curcumin (5× and 10×) at RT on an orbital shaker, under oligomerization conditions. Tau oligomers in the absence and presence of curcumin were evaluated biochemically using the oligomer-specific antibody T22 and total tau antibodies, Tau 5 and Tau 13 (FIG. 2).

Figure 2A:
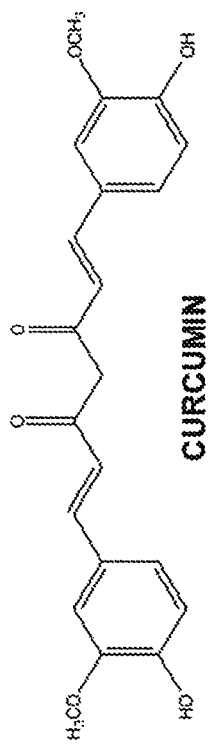
FIGS. 2A-D Biochemical and cytotoxicity analysis of oligomeric Tau treated with curcumin and untreated control.
Figure 2A:
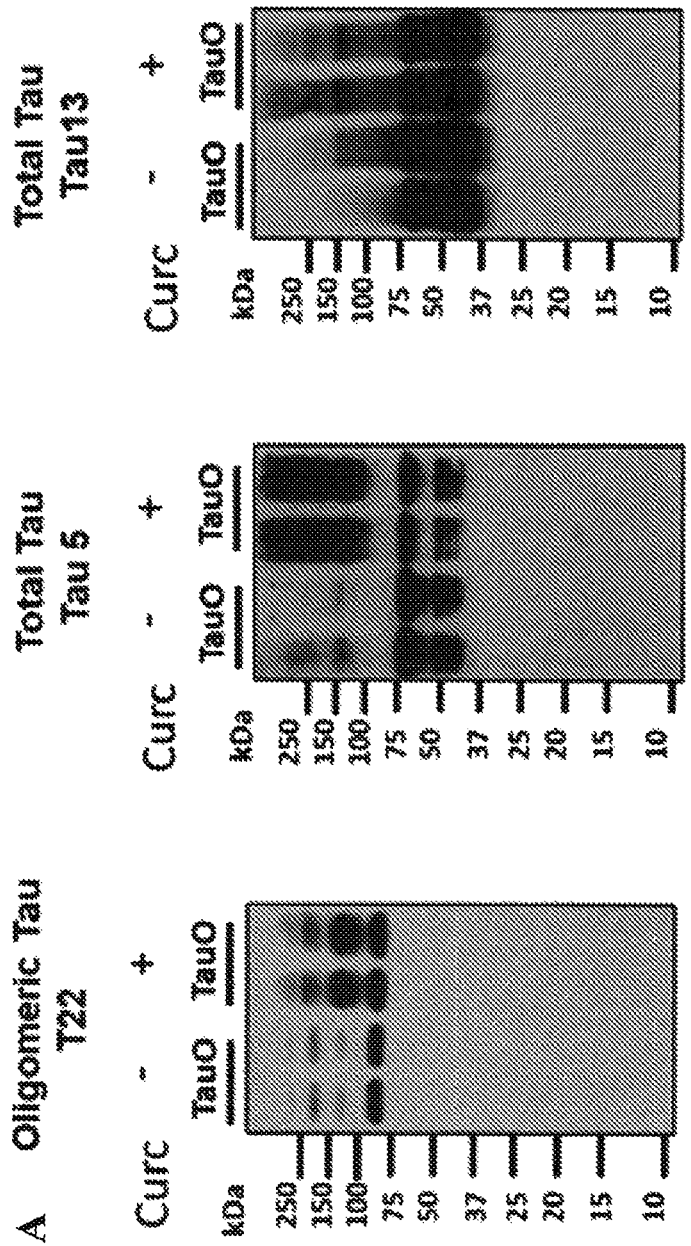
Figure 2D:
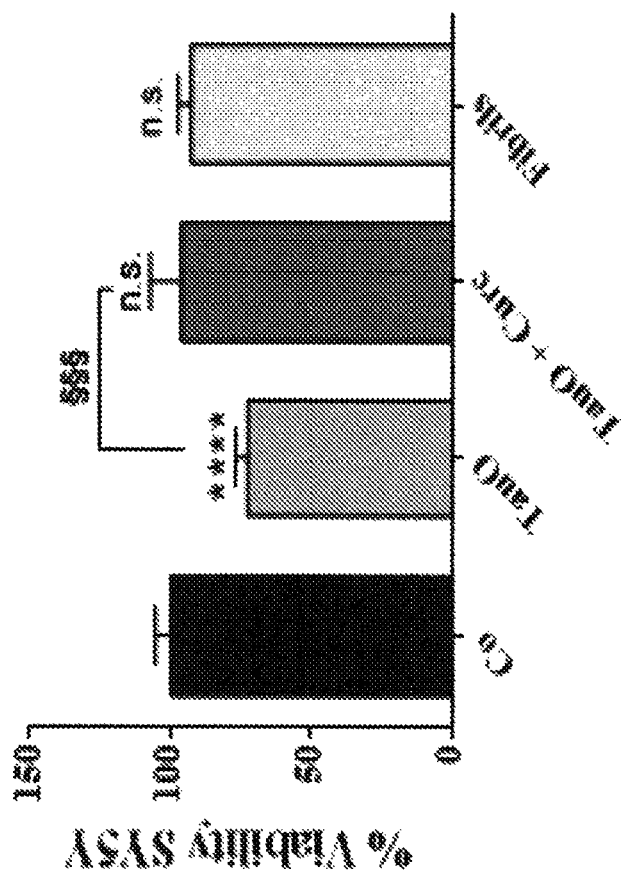

Western blot analysis showed that curcumin interacts with tau oligomers promoting the formation of larger tau aggregates (FIG. 2A). In addition, direct ELISA and dot blot analyses showed a significant decrease in oligomers, as seen by the decrease in T22 immunoreactivity (Figure B—C). Next, the toxicity of these aggregated tau species, resulting from the co-incubation of TauO with curcumin, was assessed by MTT using the human neuroblastoma cell line, SH-SY5Y. Cells were exposed to tau oligomers alone (2 µM) or in the presence of curcumin (final concentration 10 µM). SH-SY5Y viability decreased significantly after treatment with TauO, while the presence of curcumin rescued cells from TauO-induced toxicity as seen by the higher cell viability compared to the untreated control (Ctrl) (FIG. 2D).

These exciting results led to the synthesis of the novel curcumin derivatives of the invention in an effort to improve curcumin's poor solubility in aqueous buffers and low bioavailability (FIG. 1). The library of our newly synthesized curcumin-derived small molecules comprises four different groups of compounds with the potential to target and modulate tau oligomers aggregation state, thus neutralizing their toxicity and internalization potency in an effort to prevent or slow the spread of the pathology. Therefore, their efficacy was tested in vitro using recombinant tau oligomers and disease-relevant tau oligomeric strains were used to validate the effects of the most promising hit compounds, as shown in the following schematic (FIG. 3).

Synthesis

Hemi-curcuminoid analogs 2-5 were obtained by adapting previously reported condensation reactions (Scheme 4.1). Unsaturated ketones 2 were obtained through Claisen-Schmidt Aldol condensation (Agarwal, Srivastava et al. 2005), by treating commercial aldehydes 1 with acetone under basic conditions. In turn, reaction of compounds 2 with iodine, in the presence of CuO as catalyst, yields to iodo-derivatives 3 (Wang, Yin et al. 2008). E-Cinnamic acids 4 were obtained performing Doebner modification of Knoevenagel condensation (Mori, Wada et al. 2017), ethyl cinnamate 4k was similarly obtained (Battisti, Palumbo Piccionello et al. 2017). Cinnamonitriles 5a,h were obtained from benzaldehyde 1 condensation with acetonitrile, as previously reported (Khurana, Ali et al. 2014).

and therefore, of associated tautomeric equilibria of the -diketone moiety, partially responsible for curcumin metabolic instability and poor pharmacokinetic properties (Sardjiman, Reksohadiprodjo et al. 1997). The synthesis of $CL_{1-12}$, was performed through two aldol-condensation of

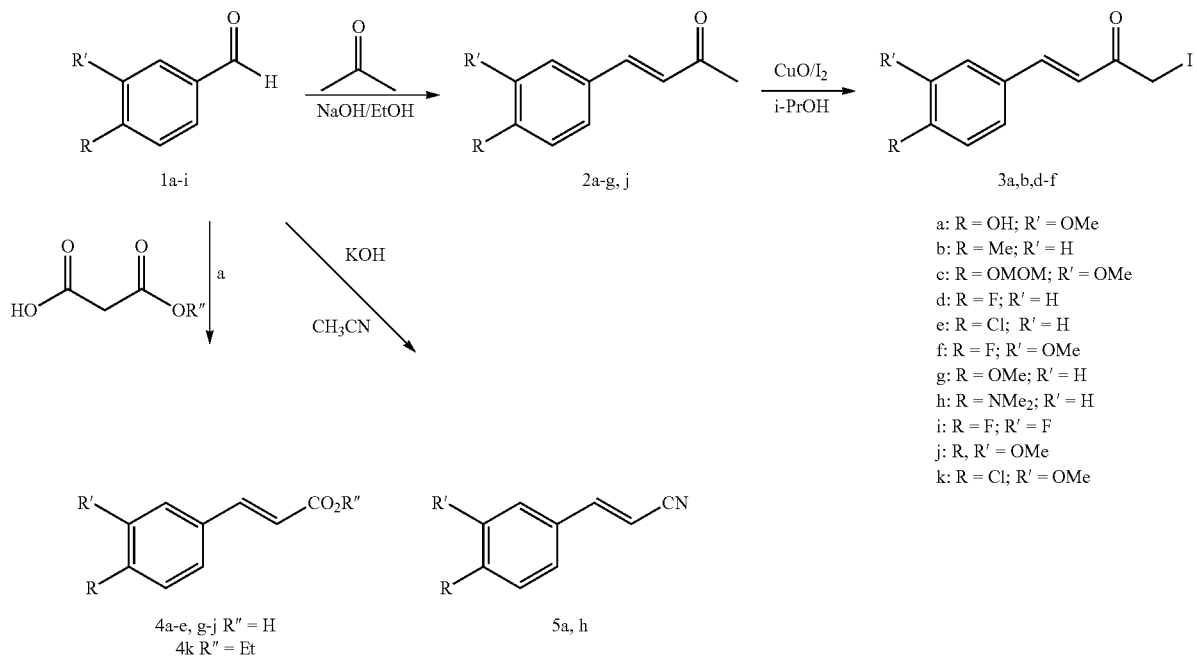

Scheme 4.1. Synthesis of Hemi-curcuminoid compounds.

(a) R″ = H: pyridine, aniline (cat), toluene, reflux; R″ = Et: pyridine, piperidine, reflux.

Among obtained compounds 2-5 were selected Hemi-curcuminoid compounds $HemiC_{1-10}$ (Table 4.1) which were tested as representative example of variously substituted derivatives. On the other hand, compounds 2-5 were used as building-block for the obtainment of other target compounds (see below).

TABLE 4.1

Structures of tested Hemi-curcuminoid compounds (HemiC).

| Entry ID | Compound | X | R | R' |
|---|---|---|---|---|
| $HemiC_1$ | 2a | COMe | OH | OMe |
| $HemiC_2$ | 5a | CN | OH | OMe |
| $HemiC_3$ | 3a | $COCH_2I$ | OH | OMe |
| $HemiC_4$ | 2g | COMe | OMe | H |
| $HemiC_5$ | 4a | $CO_2H$ | OH | OMe |
| $HemiC_6$ | 2j | COMe | OMe | OMe |
| $HemiC_7$ | 4k | $CO_2Et$ | OMe | Cl |
| $HemiC_8$ | 5h | CN | $NMe_2$ | H |
| $HemiC_9$ | 2b | COMe | Me | H |
| $HemiC_{10}$ | 2c | COMe | OMOM | OMe |

Cinnamils (1,6-diarylhexa-1,5-diene-3,4-diones) CL are Curcumin-like analogs lacking of active methylene group aromatic aldehydes 1 on diacetyl 6 with the formation of both double bonds with E geometry (Scheme 4.2) (Sinu, Padmaja et al. 2013).

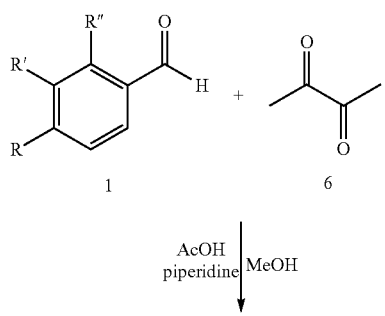

Schme 4.2. Synthesis of Cinnamils $CL_{1-12}$.

-continued

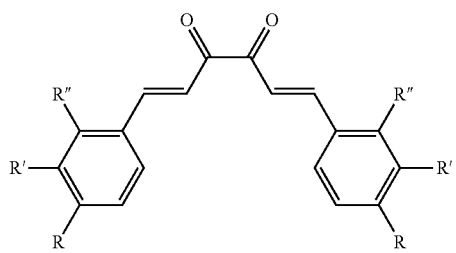

CL₁: R = OMe; R', R'' = H
CL₂: R, R', R'' = H
CL₃: R = F; R', R'' = H
CL₄: R = NMe₂; R' = H
CL₅: R = Cl; R', R'' = H
CL₆: R = F; R' = F
CL₇: R' = Cl; R, R'' = H
CL₈: R'' = Cl; R, R' = H
CL₉: R' = OMe; R, R'' = H
CL₁₀: R = OMOM; R' = OMe; R'' = H
CL₁₁: R, R' = OCH₂O; R'' = H
CL₁₂: R = CO₂H; R', R'' = H

Another possible strategy is the substitution of the curcumin central core with heterocyclic rings, as previously reported for the design novel scaffolds able to target A oligomers (Battisti, Palumbo Piccionello et al. 2017). In particular, we previously constructed a database of structures endowed with a more stable and planar heterocycle. The virtual screening was accomplished through the calculation of molecular descriptors able to highlight the drug-like profile based on Lipinski's rules (rule of five) and by taking into account the molecular descriptors such as log BB, which allows the evaluation of BBB permeation ability (Battisti, Palumbo Piccionello et al. 2017). From this screening, were selected two scaffolds, 1,2,4- and 1,3,4-oxadiazole regio-isomers, two heterocyclic nuclei widely studied for AD treatment (Mangione, Palumbo Piccionello et al. 2015, Martorana, Giacalone et al. 2016). In particular, following Scheme 4.3, the 1,2,4-oxadiazole derivatives CH₁₋₄, were obtained by adopting the conventional amidoxime route (Pace, Buscemi et al. 2015), starting from the esters 7 and amidoximes 8.

Scheme 4.3. Synthesis of Heterocyclic curcumin-like 1,2,4-oxadiazoles CH₁₋₄.

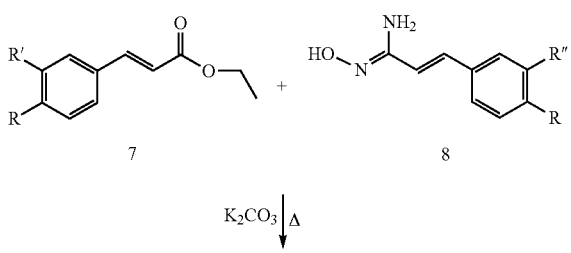

-continued

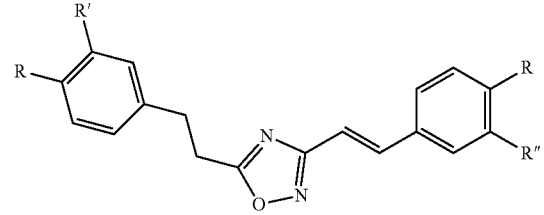

CH₁: R, R', R'' = OMe
CH₂: R = OMe; R', R'' = H
CH₃: R, R', R'' = H
CH₄: R, R'' = OMe; R' = Cl

The 1,3,4-oxadiazole regio-isomers CH₇₋₁₁, from Scheme 4.4, were obtained from the one-pot construction of a diacylhydrazine intermediate, followed by cyclization and starting from the cinnamic acid analogue 4 (Stabile, Lamonica et al. 2010). All compounds were region-selectively obtained in E geometry in good overall yields.

Scheme 4.4. Synthesis of Heterocyclic curcumin-like 1,3,4-oxadiazoles CH₇₋₁₁.

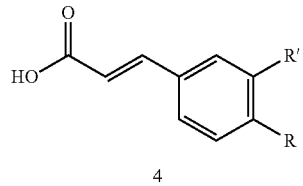

1) EDC/HOBt/NH₂NH₂
2) TsCl/DIPEA

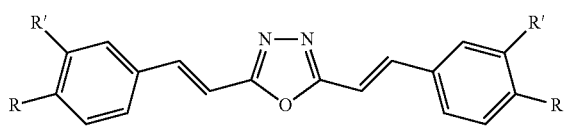

CH₅: R, R' = F
CH₆: R = Cl; R' = H
CH₇: R, R' = OCH₂O
CH₈: R = NMe₂; R' = H
CH₉: R, R' = OMe
CH₁₀: R = OMe; R' = H
CH₁₁: R = OMOM; R' = OMe

The last group of curcumin derivatives that were synthesized are the Calebin-A analogs. Calebin-A is a polyphenol compounds derived from turmeric of Curcuma Longa and was previously reported as neuroprotective compounds active toward A peptide (Park and Kim 2002). The synthesis of Calebin-A and its analogs Cal₁₋₉ was accomplished by coupling, through a nucleophilic substitution reaction, iodo-derivatives 3 and cinnamic acids 4 [Majeed, M.; Nagabhushanam, K.; Majeed, A.; Thomas, S. M. Eur. Pat. Appl. 2016, EP 2963007], avoiding the use of protective groups (Scheme 4.5).

Scheme 4.5. Synthesis of Calebin-A like compounds Cal$_{1-9}$.

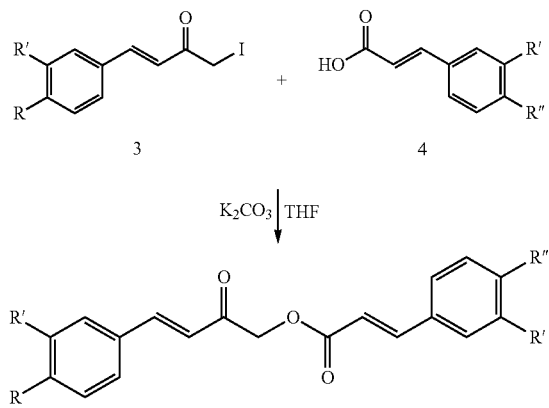

Cal$_1$: R, R', R'' = OMe
Cal$_2$: R, R'' = OMe; R' = H
Cal$_3$: R, R'' = Me; R' = H
Cal$_4$: R= OMOM; R', R'' = OMe
Cal$_5$: R, R' = CH$_2$OCH$_2$; R'', R' = CH$_2$OCH$_2$
Cal$_6$: R, R'' = F; R' = H
Cal$_7$: R, R'' = Cl; R' = H
Cal$_8$: R, R'' = OH; R' = OMe
Cal$_9$: R = F; R', R'' = OMe

All these newly synthesized compounds were screened and tested to evaluate and assess their efficacy in interacting and altering tau aggregation pathways using recombinant tau oligomers.

Hemi-Curcuminoids (HemiC1-10)

The first group of curcumin analogs are the Hemi-curcuminoids (HemiC1-10). These compounds were synthesized using ferulic acid as a reference, since it structurally correlates to a half portion of curcumin. Therefore, the Hemi-curcuminoids, that have been obtained, are variously substituted and functionalized styrene derivatives with a very low molecular weight (MW from 160 to 260 Da). Tau oligomers were incubated alone or in the presence of curcumin and Hemi-curcuminoids derivatives (5×) for 16 hours under oligomerization conditions and reactions were assessed using T22 antibody. Western blot analysis in FIG. 4A showed the altered aggregation of preformed tau oligomers after incubation with Hemi-curcuminoids. Co-incubation with these derivatives showed the capability of some Hemi-curcuminoids to reduce tau oligomer levels and others to induce the formation of higher molecular weight non-toxic aggregates.

Dot blots analysis of tau oligomers alone or in the presence of the HemiC compounds showed reduction in TauO after incubation with some Hemi-curcuminoids, as seen by the decreased TOMA1 and T22 immunoreactivities (FIG. 4B). TOMA1 is a conformational monoclonal antibody that recognizes conformational epitopes that do not depend on linear amino acid sequences and displays distinct preferences for different subsets of tau oligomer (Castillo-Carranza, Sengupta et al. 2014), suggesting that the treatment with the HemiC compounds led to a conformational changes in the preformed oligomeric tau species. The potency of these analogs was also confirmed by direct ELISA showing a significant decrease in oligomers detection by T22 antibody with no differences using total tau antibody, Tau 5 (FIG. 4C).

Taken together, our results suggest that Hemi-curcuminoids interact and modulate the aggregation of preformed oligomeric tau species promoting the formation of larger non-toxic tau aggregates or decreasing tau oligomers levels.

Curcumin-Like (CL1-12)

The second group of curcumin derivatives (CL1-12) displays the same structure of curcumin with different substitutions and functionalizations. Tau oligomers, incubated alone or in the presence of curcumin and Curcumin-like analogs (5×), were biochemically assessed by western blot using T22 as well as the total tau antibody, Tau 5. FIG. 5A shows the capability of each curcumin-like derivate to interact with preformed tau oligomers modulating their aggregation states, resulting in the formation of larger and higher molecular weight non-toxic aggregates. Dot blots assay showed reduction in TauO levels after incubation with Curcumin-like derivatives, as assessed by the decreased TOMA1 and T22 immunoreactivities and no changes were observed in total tau, once probed with Tau5. Direct ELISA confirmed the previous results; untreated tau oligomers showed strong immunoreactivity with T22 while, in the presence of the compounds, there was a reduced immunoreactivity suggesting their capability to modulate the aggregation pathway of preformed tau oligomers aggregation (FIG. 5).

Heterocyclic Curcumin Analogs (CH1-11)

The next group of newly synthesized derivatives are the Heterocyclic curcumin analogs that display the same structure of the lead compound curcumin with the introduction of a heterocyclic moiety e.g. imidazole, pyridine and pyrazole among others. These compounds have been synthesized following Lipinski's rule of five to obtain active molecules that can easily pass through the BBB. Heterocyclic curcumin derivatives' effects on recombinant tau oligomers were evaluated biochemically (FIG. 6). Western blot analysis showed that the treatment with Heterocyclic derivative induces the formation of larger tau species (FIG. 6A). Dot blot and filter trap analyses showed decreased T22 immunoreactivity after co-incubation with the compounds as compared to the untreated tau oligomers. Moreover, some derivatives were also able to reduce TOMA1 immunoreactivity, suggesting that conformational changes have occurred in the preformed oligomeric tau species after treatment with the Heterocyclic analogs (FIG. 6B).

Dot blot and filter trap assays probed with Tau5 as control, showed no changes in total tau protein. These results were also confirmed by direct ELISA (FIG. 6C).

Calebin-A Analogs (Cal1-9)

The last group of curcumin derivatives screened are the Calebin-A derivatives. Calebin-A is a natural occurring small molecule obtained from the rhizome of Curcuma Longa like curcumin. Calebin-A was previously reported as neuroprotective compounds active against Aβ insult (Park and Kim 2002). The structural difference with curcumin is the lacking of the 1,3 diketonic structure. However, Calebin-A as well as curcumin showed to have poor solubility in water and low bioavailabity, thus derivatives were synthesized to improve these shortcomings (Oliveira, Martinez et al. 2015).

Calebin-A derivatives were incubated with preformed tau oligomers and their effects were evaluated by western blot and dot blot analyses showing the potency of the compounds in altering the aggregation pathways of preformed tau oligomers (FIG. 7). Biochemical anylysis of tau oligomers after incubation with Calebin-A derivatives shows that the Calebin-A-derived small molecules are able to decrease the oligomer levels and promote the formation of higher molecular weight aggregates as seen by western blot as well as filter trap assay analyses. Furthermore, direct ELISA show significant decrease in tau oligomer levels after treatment with some of the Calebin-A derivatives as assessed by the reduced T22 immunoreactivity.

Based on the biochemical screens, we selected three compounds of each group showing higher activity with recombinant tau oligomers for additional in vitro testing, listed below (Table 4.2).

TABLE 4.2

Selected compounds for each group of curcumin derivatives.

| HemiCurcuminoids | Curcumin-like |
|---|---|
| 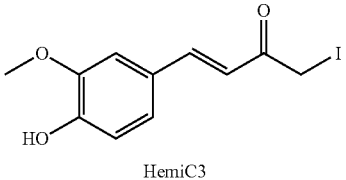 HemiC3 | 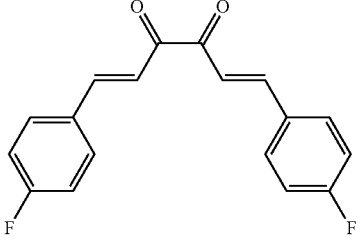 CL3 |
| 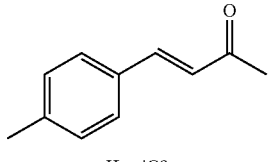 HemiC9 | 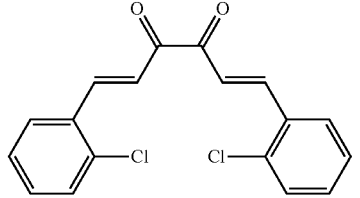 CL7 |
| 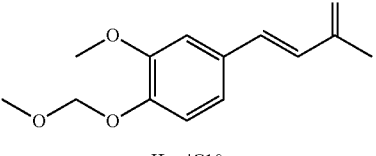 HemiC10 | 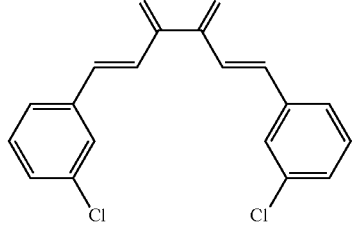 CL8 |

| Heterocyclic Curcumin | Calebin-A like |
|---|---|
| 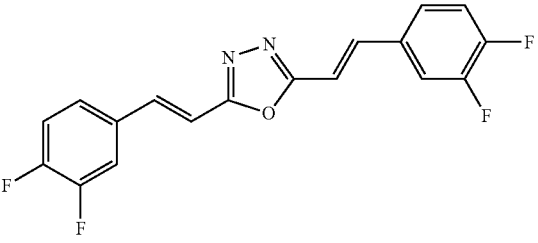 CH5 | 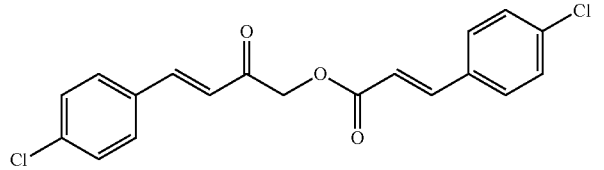 Cal7 |

TABLE 4.2-continued

Selected compounds for each group of curcumin derivatives.

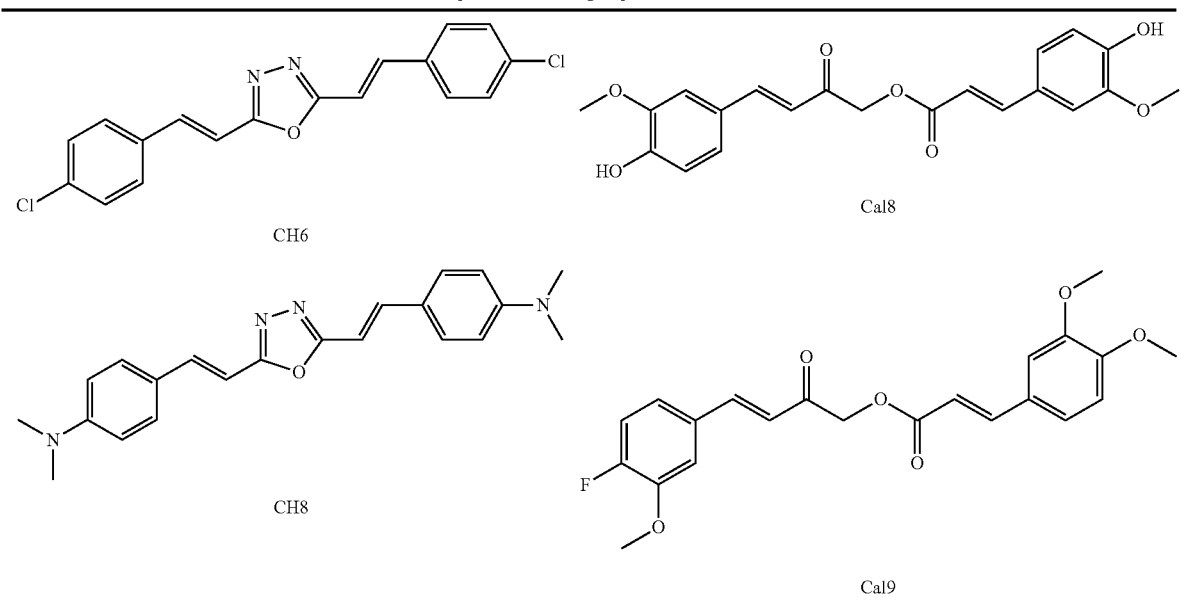

Therefore, the curcumin derivatives selected were further tested biochemically using preformed recombinant tau oligomers to evaluate their effects in parallel, side by side and under the same conditions. Indeed, oligomeric tau species were incubated with and without curcumin derivatives (final conc. 5 µM) and were evaluated biochemically using the oligomer-specific antibody T22 and generic tau antibody, Tau 5 (FIG. 8).

Western blot analysis showed that curcumin-derived small molecules interact with recombinant tau oligomers resulting in decreased oligomer levels or leading to tau structures with higher molecular weight. In addition, filter trap assay confirmed that some of the compounds modulate the aggregation pathway of preformed tau oligomers resulting in decreased T22 immunoreactivity as compared to the untreated oligomers. Moreover, direct ELISA showed that curcumin derivatives interactions with tau oligomers resulted in decreased oligomer level as detected by T22 oligomeric-specific tau antibody. As a result from these additional screenings, we selected six promising compounds, showing to affect the aggregation state of toxic tau oligomers. These hit compounds were further tested biophysically as well as cytotoxicity screens were performed to evaluate their ability to modulate tau oligomers associated neurotoxicity.

Therefore, tau oligomers with and without the selected active compounds were also characterized biophysically (FIG. 9). Fast protein liquid chromatography (FPLC) was used to purified tau oligomers detecting a main peak at ~120-150 kDa (tau dimer/trimer). Atomic force microscopy was performed to assess the morphology of purified tau oligomers before and after treatment with the curcumin derivatives. AFM images of tau oligomers alone displayed their clasically homogeneous spherical morphology, with the majority of the oligomers with a diameter of 14-16 nm as shown by the size distribution histogram (FIG. 9B); The presence of the curcumin-derived small molecules converted the smaller and spherical tau oligomers into larger tau aggregates as seen in FIG. 9C.

In addition, the cytotoxicity of each selected compound was evaluated using MTT assays in cultured human SH-SY5Y neuroblastoma cell line by exposing cells for 24 hours with increasing concentrations of the hit compounds within the range 0-800 µM. Our results showed that the curcumin derivatives have a very low toxic profile as shown by the dose-response curves in FIG. 10.

Figure 11:
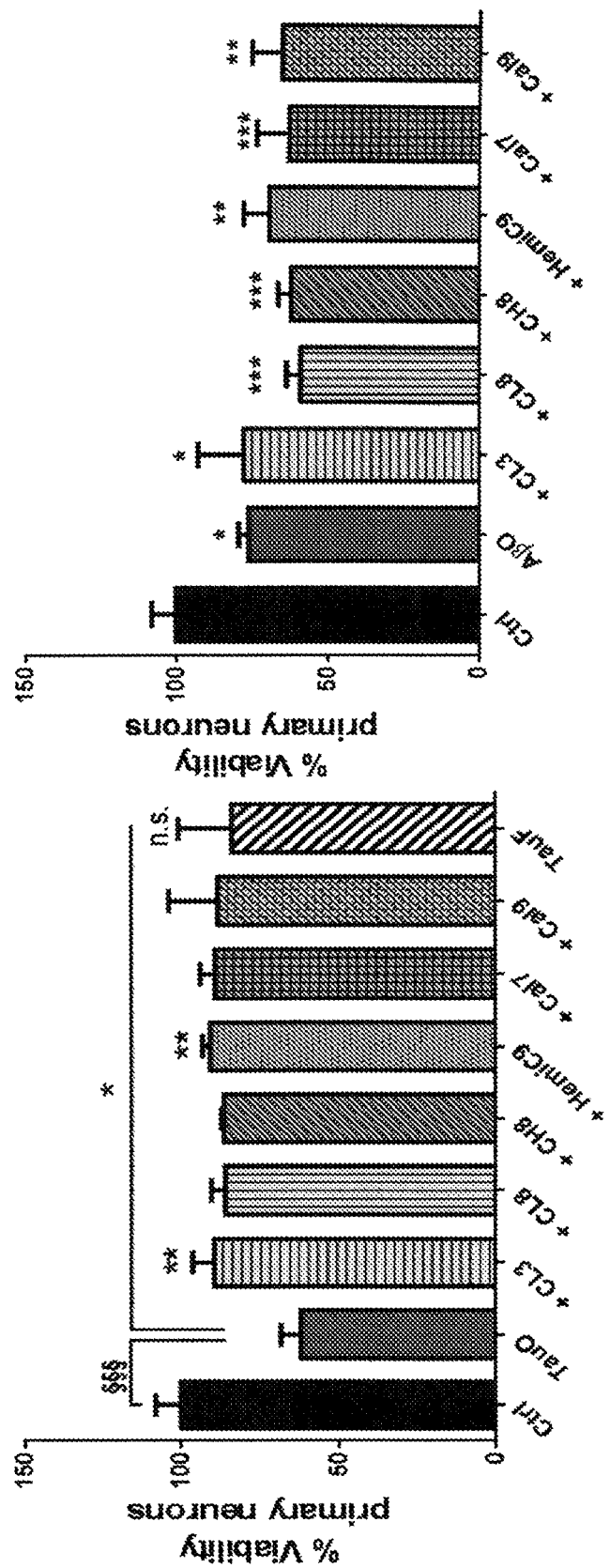

Next, the toxicity of the curcumin derivative-induced aggregates was evaluated by using primary cortical neurons isolated from embryos of Htau mice, expressing non-mutant human tau. Cells were exposed to tau oligomers alone or in the presence of curcumin derivatives and Aβ oligomers (AβO) were used as a control (FIG. 11). Cell viability significantly decreased after treatment with untreated TauO, while treatment with curcumin derivatives (final concentration 5 µM) reduced their toxicity significantly as seen by the higher level of cell viability using MTT assay.

Interestingly, curcumin derivatives were also incubated with Aβ oligomers and toxicity screens in primary neurons showed that the compounds were not able to rescue neurons from Aβ oligomers-induced toxicity (FIG. 11B).

Furthermore, to further confirm our findings and gain a better understanding of the protective role of curcumin derivatives, SH-SY5Y human neuroblastoma cells were treated with sub-lethal concentration of TauO or TauO after treatment with the curcumin compounds and imaged by fluorescence microscopy.

Tau oligomers were observed in the plasma membranes as well as in the nuclei, as shown by PCC graph, indicating extensive cellular internalization of TauO.

Furthermore, cells exposed to untreated TauO, exhibit extensive loss of plasma membrane integrity, reflecting the toxic effect of tau oligomers. Interestingly, SH-SY5Y cells that were treated with TauO, co-incubated with curcumin derivatives, show a significant reduction in the percentage of area positive of TauO staining. Immunofluorescence analysis shows that the tau species, resulting from the incubation of curcumin derivatives, mostly co-localize with the plasma membrane.

Altogether, these data suggest that curcumin derivatives-induced aggregates are less prone to be internalized by the cells, elucidating their reduced cytotoxicity.

In addition, curcumin derivatives, showing high activity with recombinant tau oligomers, were tested using disease-relevant brain-derived tau oligomers (BDTOs) from different tauopathies.

The isolation of BDTOs (Lasagna-Reeves 2012, Gerson, Sengupta et al. 2014) to directly test whether tau oligomers form conformationally distinct strains that depend upon individual and/or disease difference is known. One of the most common determinants of strain differences in the prion field is the stability of the protein core following exposure to Proteinase K (PK) (Legname, Nguyen et al. 2005, Ghaemmaghami, Watts et al. 2011). Recent studies demonstrated that also aggregated tau exhibits variable protease stability similar to prions (Sanders, Kaufman et al. 2014).

To characterize disease-relevant tau oligomeric strains, BDTOs were isolated by immunoprecipitation with the oligomeric tau antibody, T22, using brain homogenates from different neurodegenerative tauopathies. BDTOs were then purified by FPLC and characterized, alone and in the presence of small molecules, biophysically and biochemically to evaluate the ability of each compound to affect BDTOs strains aggregation state and toxicity.

Brain homogenates from DLB, AD and PSP were isolated and characterized by AFM. Images from each BDTO displayed a different morphology (FIG. 12A). One of the most common determinants of strain differences in the prion field is the stability of the protein core following exposure to PK. Therefore, BDTOs were exposed at 1 µg/ml of PK and evaluated by western blot using the sequence specific anti-tau antibody, Tau 5 Western blot analysis revealed that each BDTO strain has different patterns of fragmentation (FIG. 12B).

In addition, Tau strains toxicity was evaluated using primary cortical neurons, isolated from Htau mice, which better mimic the physiology of cells in vivo. Indeed, gene as well protein expression profiles in primary neurons better resemble those of the differentiated cell in vivo and are also more appropriate for drug targeting validation. Hence, primary neurons, exposed to 0.5 µM BDTOs for 2 hours, showed a significant decrease in cell viability as compared to untreated cells, Ctrl (FIG. 12C).

Therefore, using methods from the prion field, we found that tau oligomers purified from different tauopathies exhibit different aggregate compositions under atomic force microscopy (AFM) and specific PK digestion profile, indicating that brain-derived tau oligomers from different disorders form structurally distinct strains.

After characterizing biochemically and biophysically BDTOs, tau oligomeric strains isolated from PSP brain homogenates, were treated with three of the derived small molecules, CL1-3, showing high activity with recombinant tau oligomers.

Figure 13:
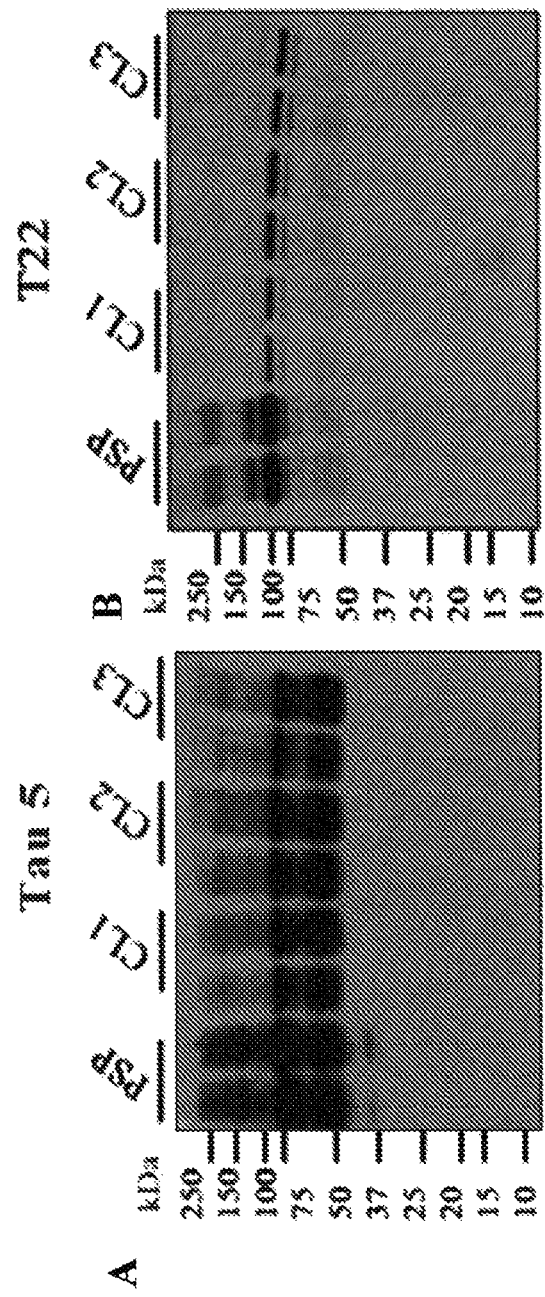
Figure 13:
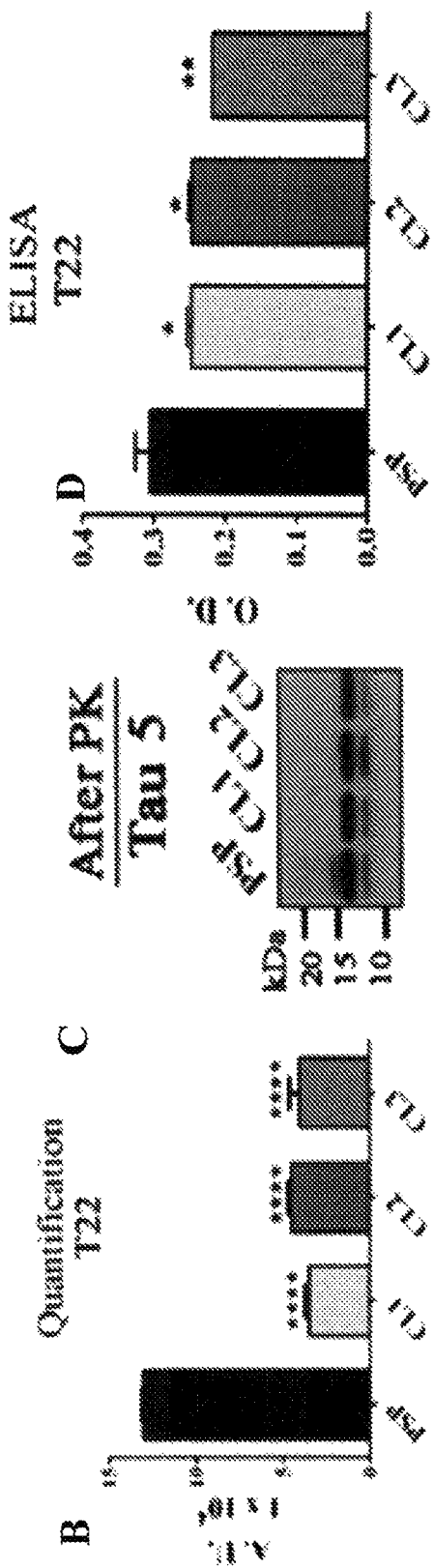

Therefore, BDTOs were incubated alone or in the presence of curcumin analogs (final conc. 5 µM) for 16 hours, under oligomerization conditions. PSP-derived oligomers were evaluated by western blot using T22 and Tau 5 antibodies (FIG. 13A), revealing that the aggregation state of BDTOs was modulated by incubation with the CL derivatives. Western blot analysis showed a significant decrease in T22 immunoreactivity when PSP derived oligomers were incubated with CL1-3 as compared to the untreated BDTOs (FIG. 13B).

Furthermore, PSP Tau strains, alone or in the presence of the Curcumin-like derivatives, were also exposed to PK digestion and evaluated by Western blot using the generic tau antibody, Tau 5. Western blot analysis showed that Curcumin-like derived small molecules affect the protein core stability (FIG. 13C). In addition, direct ELISA analysis confirmed the previous results, revealing a decreased T22 immunoreactivity when BDTOs were incubated with CL1-3 as compared to the untreated control (FIG. 13D).

Next, the toxicity of these tau aggregated species, resulting from the co-incubation of BDTOs with CL3, was investigated to assess the ability of the newly synthesized small molecules to prevent and reduce brain-derived tau oligomer-induced toxicity in primary cortical neurons, isolated from Htau mice.

Therefore, primary neurons were exposed to 0.5 µM of untreated BDTOs from PSP and AD and incubated with CL3 (final concentration 5 µM) and controls. Viability significantly decreased when cells were treated with BDTOs alone, while the treatment with CL3 reduced PSP-derived tau oligomers toxicity as seen by the higher cell viability.

Interestingly, CL3 showed to be able to rescue primary neurons from PSP BDTOs-induced toxicity and were not be able to modulate and neutralize AD BDTOs-induced toxicity, suggesting that this promising compound may specifically bind to PSP tau strain.

Furthermore, PSP and AD BDTOs alone and in the presence of CL3 were evaluated by AFM to assess their morphology and aggregation state (FIG. 4.17B).

Excitingly, AFM images confirmed the capability of CL3 to modulate the aggregation state of PSP BDTOs leading to the formation of larger tau aggregates while no morphological changes were observed in AFM images of AD BDTOs with and without treatment with the Curcumin-like derivate CL3.

Altogether, these results show the efficacy of Curcumin-like compounds to interact with BDTOs isolated from PSP homogenates, and modulate their aggregation states by promoting the formation of non-toxic larger tau aggregates. In addition, CL3 modulates PSP BDTOs associated neurotoxicity and has no effect in preventing AD BDTOs-induced toxicity, suggesting that this promising compound may specifically bind to PSP tau strains.

Spectra Extracted with LSM 880 Zeiss of Recombinant (rTauO) and Brain-Derived Tau Oligomers (BDTOs)

Fluorescent properties of curcumin derivatives as imaging probe using:
recombinant Tau oligomer (Flames)
Brain-derived Tau oligomers (Flames)
Human and mice brain slice sections (Immunofluorescence)

Confocal-Based Spectral Profiling of Fluorescent Amyloid-Binding Dyes in Gel-Embedded Recombinant (rTauO) and Brain-Derived tau Oligomers (BDTO)s ThT-, Curcumin-, FSB—, CL3-, CL8-, CH8-, HemiC9, Cal7-labeled recombinant and disease-relevant oligomeric tau deposits were imaged in the spectral (Lambda) scan mode of a Zeiss LSM880 confocal microscope using a 40× water immersion lens (1.1 NA), a 405-nm laser for fluorescent amyloid-dye excitation, and a HyD detector at 512-× 512-pixel resolution. Fluorescence emission was acquired from a series of 40-image steps spanning from 410- to 710-nm wavelengths using a 10-nm-wide detection window at each interval. For each field-of-view in the gel-embedded synthetic amyloid-beta fibril and Tau oligomers, confocal z-stack at multiple random positions in a well was acquired with identical spectral parameters as described above (XYλZ mode) using a 40× water immersion lens (1.2 NA) with optical zoom 5×. The size of the z-stack ranged from 50- to 100-μm thick depending on the density of aggregates in a given well. Raw spectral data were analyzed with Zeiss LITE Blue and NIH ImageJ-FIJI software.

Protocol for IF in Frozen Human and Mice Brain Sections Using Curcumin and Curcumin Derivatives 1. Fix brain sections in 4% paraformaldehyde at room temperature (RT).
2. Wash two times for 10 min in PBS 1×.
3. Circle section with marker pen.
4. Wash in 70% ETOH for 5 min.
5. Apply Autofluorescence eliminator reagent (Millipore) or other autofluorescence inhibitor.
6. Wash three times for 1 min in 70% ETOH, until ETOH runs clear.
7. Wash in PBS 1× for 10 min.
8. 60 min block non-specific sites in PBS 5% Goat serum in 1× PBS in the humidifier chamber.
9. Incubate with Curcumin or Curcumin derivatives (0.5-1 mM at 4° C.) for 20 min.
10. Wash three times for 10 min in PBS 1×.
11. Incubate with primary antibody (e.g. Oligomeric specific anti-tau antibody, T22 (1:250)), diluted in 5% Goat serum in 1× PBS, overnight at 4° C. in humidity chamber.
12. Wash three times for 10 min in PBS 1×.
13. Incubate with secondary antibody (e.g. goat anti-rabbit Alexa Fluor-568 (1:500)) for 1 hr at RT in humidity chamber.
14. Wash three times for 10 min in PBS 1×.
15. Apply Prolong Gold Antifade mounting media with DAPI and cover with coverslip.
16. Image with a Keyence BZ-800 Microscope using standard filters for DAPI, GFP and Texas Red.

It is to be understood that both the foregoing general description of the invention do not restrict the scope of the invention.

All publications mentioned herein are incorporated by reference to the extent they support the present invention.

Agarwal, A., K. Srivastava, S. K. Puri and P. M. Chauhan (2005). "Syntheses of 2,4,6-trisubstituted triazines as antimalarial agents." Bioorg Med Chem Lett 15(3): 531-533.

Battisti, A., A. Palumbo Piccionello, A. Sgarbossa, S. Vilasi, C. Ricci, F. Ghetti, F. Spinozzi, A. Marino Gammazza, V. Giacalone, A. Martorana, A. Lauria, C. Ferrero, D. Bulone, M. R. Mangione, P. L. San Biagio and M. G. Ortore (2017). "Curcumin-like compounds designed to modify amyloid beta peptide aggregation patterns." RSC Advances 7(50): 31714-31724.

Beaudoin, G. M., 3rd, S. H. Lee, D. Singh, Y. Yuan, Y. G. Ng, L. F. Reichardt and J. Arikkath (2012). "Culturing pyramidal neurons from the early postnatal mouse hippocampus and cortex." Nat Protoc 7(9): 1741-1754.

Castillo-Carranza, D. L., M. J. Guerrero-Munoz, U. Sengupta, J. E. Gerson and R. Kayed (2018). "alpha-Synuclein Oligomers Induce a Unique Toxic Tau Strain." Biol Psychiatry.

Castillo-Carranza, D. L., U. Sengupta, M. J. Guerrero-Munoz, C. A. Lasagna-Reeves, J. E. Gerson, G. Singh, D. M. Estes, A. D. Barrett, K. T. Dineley, G. R. Jackson and R. Kayed (2014). "Passive immunization with Tau oligomer monoclonal antibody reverses tauopathy phenotypes without affecting hyperphosphorylated neurofibrillary tangles." J Neurosci 34(12): 4260-4272.

Gerson, J., D. L. Castillo-Carranza, U. Sengupta, R. Bodani, D. S. Prough, D. S. DeWitt, B. E. Hawkins and R. Kayed (2016). "Tau Oligomers Derived from Traumatic Brain Injury Cause Cognitive Impairment and Accelerate Onset of Pathology in Htau Mice." J Neurotrauma 33(22): 2034-2043.

Gerson, J., U. Sengupta, C. Lasagna-Reeves, M. Guerrero-Munoz, J. Troncoso and R. Kayed (2014). "Characterization of tau oligomeric seeds in progressive supranuclear palsy." Acta Neuropathologica Communications 2(1): 73.

Ghaemmaghami, S., J. C. Watts, H.-O. Nguyen, S. Hayashi, S. J. DeArmond and S. Prusiner (2011). "Conformational Transformation and Selection of Synthetic Prion Strains." Journal of Molecular Biology 413(3): 527-542.

Khurana, L., H. I. Ali, T. Olszewska, K. H. Ahn, A. Damaraju, D. A. Kendall and D. Lu (2014). "Optimization of Chemical Functionalities of Indole-2-carboxamides To Improve Allosteric Parameters for the Cannabinoid Receptor 1 (CB1)." Journal of Medicinal Chemistry 57(7): 3040-3052.

Lasagna-Reeves, C., D. L. Castillo-Carranza, M. J. Guerrero-Muñoz, G. R. Jackson and R. Kayed (2010). "Preparation and Characterization of Neurotoxic Tau Oligomers." Biochemistry 49(47): 10039-10041.

Lasagna-Reeves, C., Castillo-Carranza, D. L., Sengupta, U., Guerrero-Munoz, M. J., Kiritoshi, T., Neugebauer, V., Jackson, G. R., Kayed, R. (2012). "Alzheimer brain-derived tau oligomers propagate pathology from endogenous tau." Sci. Rep. 2: 1-7.

Cristian A. Lasagna-Reeves, Diana L. Castillo-Carranza, Urmi Sengupta, Jose Sarmiento, 1 Juan Troncoso, George R. Jackson, and Rakez Kayed, FASEB J. (2012)s May; 26(5): 1946-1959.

Legname, G., H.-O. B. Nguyen, I. V. Baskakov, F. E. Cohen, S. J. DeArmond and S. B. Prusiner (2005). "Strain-specified characteristics of mouse synthetic prions." Proceedings of the National Academy of Sciences of the United States of America 102(6): 2168-2173.

List, B., A. Doehring, M. T. Hechavarria Fonseca, A. Job and R. Rios Torres (2006). "A Practical, efficient, and atom economic alternative to the Wittig and Horner-Wadsworth-Emmons reactions for the synthesis of (E)-α,β-unsaturated esters from aldehydes." Tetrahedron 62(2): 476-482.

Lo Cascio, F. and R. Kayed (2018). "Azure C Targets and Modulates Toxic Tau Oligomers." 9(6): 1317-1326.

Mangione, M. R., A. Palumbo Piccionello, C. Marino, M. G. Ortore, P. Picone, S. Vilasi, M. Di Carlo, S. Buscemi, D. Bulone and P. L. San Biagio (2015). "Photo-inhibition of Aβ fibrillation mediated by a newly designed fluorinated oxadiazole." RSC Advances 5(21): 16540-16548.

Margittai, M. and R. Langen (2004). "Template-assisted filament growth by parallel stacking of tau." Proc Natl Acad Sci U S A 101(28): 10278-10283.

Margittai, M. and R. Langen (2006). "Side chain-dependent stacking modulates tau filament structure." J Biol Chem 281(49): 37820-37827.

Martorana, A., V. Giacalone, R. Bonsignore, A. Pace, C. Gentile, I. Pibiri, S. Buscemi, A. Lauria and A. P. Piccionello (2016). "Heterocyclic Scaffolds for the Treatment of Alzheimer's Disease." Curr Pharm Des 22(26): 3971-3995.

Mori, H., R. Wada, S. Takahara, Y. Horino, H. Izumi, T. Ishimoto, T. Yoshida, M. Mizuguchi, T. Obita, H. Gouda, S. Hirono and N. Toyooka (2017). "A novel serine racemase inhibitor suppresses neuronal over-activation in vivo." Bioorg Med Chem 25(14): 3736-3745.

Oliveira, A. L., S. E. Martinez, K. Nagabushnam, M. Majeed, S. Alrushaid, C. L. Sayre and N. M. Davies (2015). "Calebin A: Analytical Development for Pharmacokinetics Study, Elucidation of Pharmacological Activities and Content Analysis of Natural Health Products." J Pharm Pharm Sci 18(4): 494-514.

Pace, A., S. Buscemi, A. P. Piccionello and I. Pibiri (2015). Chapter Three—Recent Advances in the Chemistry of 1,2,4-OxadiazolesaaDedicated to Professor Nicole) Vivona on the occasion of his 75th birthday. Advances in Heterocyclic Chemistry. E. F. V. Scriven and C. A. Ramsden, Academic Press. 116: 85-136.

Park, S. Y. and D. S. Kim (2002). "Discovery of natural products from Curcuma longa that protect cells from beta-amyloid insult: a drug discovery effort against Alzheimer's disease." J Nat Prod 65(9): 1227-1231.

Rehse, K. and F. Brehme (1998). "New NO donors with antithrombotic and vasodilating activities, Part 26. Amidoximes and their prodrugs." Arch Pharm (Weinheim) 331(12): 375-379.

Sanders, D. W., S. K. Kaufman, S. L. DeVos, A. M. Sharma, H. Mirbaha, A. Li, S. J. Barker, A. Foley, J. R. Thorpe, L. C. Serpell, T. M. Miller, L. T. Grinberg, W. W. Seeley and M. I. Diamond (2014). "Distinct tau prion strains propagate in cells and mice and define different tauopathies." Neuron 82(6): 1271-1288.

Sardjiman, S. S., M. S. Reksohadiprodjo, L. Hakim, H. van der Goot and H. Timmerman (1997). "1,5-Diphenyl-1, 4-pentadiene-3-ones and cyclic analogues as antioxidative agents. Synthesis and structure-activity relationship." European Journal of Medicinal Chemistry 32(7): 625-630.

Sengupta, U., M. Montalbano, S. McAllen, G. Minuesa, M. Kharas and R. Kayed (2018). "Formation of Toxic Oligomeric Assemblies of RNA-binding Protein: Musashi in Alzheimer's disease." Acta Neuropathol Commun 6(1): 113.

Sinu, C. R., D. V. M. Padmaja, U. P. Ranjini, K. C. Seetha Lakshmi, E. Suresh and V. Nair (2013). "A Cascade Reaction Actuated by Nucleophilic Heterocyclic Carbene Catalyzed Intramolecular Addition of Enals via Homoenolate to α,β-Unsaturated Esters: Efficient Synthesis of Coumarin Derivatives." Organic Letters 15(1): 68-71.

Stabile, P., A. Lamonica, A. Ribecai, D. Castoldi, G. Guercio and O. Curcuruto (2010). "Mild and convenient one-pot synthesis of 1,3,4-oxadiazoles." Tetrahedron Letters 51(37): 4801-4805.

Wang, Z., G. Yin, J. Qin, M. Gao, L. Cao and A. Wu (2008). An Efficient Method for the Selective Iodination of α,β-Unsaturated Ketones.

Zhu, J., M. Mao, H.-J. Ji, J.-Y. Xu and L. Wu (2017). "Palladium-Catalyzed Cleavage of α-Allenylic Aryl Ether toward Pyrazolemethylene-Substituted Phosphinyl Allenes and Their Transformations via Alkenyl C—P(O) Cleavage." Organic Letters 19(8): 1946-1949.

We claim:

1. A compound of Formula I or a pharmaceutically acceptable salt thereof, wherein:

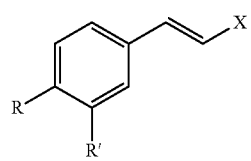

Formula I

R is OH, alkoxy, alkyl, dialkylamino, or —O-alcohol protecting group selected from OMOM or OBn;
R' is hydrogen, halogen, or alkoxy; and
X is CO—$R^1$ or COCH$_2$Y;
wherein Y is chosen from halogen, OH, OR$^1$, NH$_2$, NHR$_1$, NR$^1$R$^2$, SH, and SR$^1$;
R$^1$ and R$^2$ are independently C$_1$-C$_{10}$-alkyl; and
wherein each phenyl vinyl double bond moiety bond geometry is independently E or Z configuration.

2. The compound of claim 1, wherein: R is OH, OMe, —NMe$_2$,-OMOM, or C$_1$-C$_{10}$-alkyl.

3. The compound of claim 1, wherein: R' is H, Cl, or OMe.

4. The compound of claim 1, wherein: X is COMe, COCH$_2$I, COCH$_2$Br, COCH$_2$Cl, or COCH$_2$F and wherein the phenyl vinyl double bond geometry is in E configuration.

* * * * *